United States Patent
Pedersen et al.

(10) Patent No.: US 10,604,738 B2
(45) Date of Patent: Mar. 31, 2020

(54) TRANSCRIPTION FACTOR MEDIATED PROGRAMMING TOWARDS MEGAKARYOCYTES

(71) Applicant: Cambridge Enterprise Limited, Cambridge (GB)

(72) Inventors: Roger Pedersen, Cambridge (GB); Willem Ouwehand, Cambridge (GB); Thomas Moreau, Cambridge (GB); Cedric Ghevaert, Cambridge (GB); Matthew Trotter, Seville (ES)

(73) Assignee: Cambridge Enterprise Limited, Cambridge (GB)

( * ) Notice: Subject to any disclaimer, the term of this patent is extended or adjusted under 35 U.S.C. 154(b) by 28 days.

(21) Appl. No.: 14/407,044

(22) PCT Filed: Jun. 19, 2013

(86) PCT No.: PCT/GB2013/051600
§ 371 (c)(1),
(2) Date: Dec. 10, 2014

(87) PCT Pub. No.: WO2013/190296
PCT Pub. Date: Dec. 27, 2013

(65) Prior Publication Data
US 2015/0111296 A1  Apr. 23, 2015

(30) Foreign Application Priority Data
Jun. 19, 2012 (GB) .................................. 1210857.7

(51) Int. Cl.
*A61K 35/19* (2015.01)
*C12N 5/078* (2010.01)

(52) U.S. Cl.
CPC ........ *C12N 5/0644* (2013.01); *C12N 2501/60* (2013.01); *C12N 2506/03* (2013.01)

(58) Field of Classification Search
CPC .................................................. C12N 5/0644
See application file for complete search history.

(56) References Cited

U.S. PATENT DOCUMENTS

| | | |
|---|---|---|
| 7,282,201 B2 | 10/2007 | Miura et al. |
| 7,476,326 B2 | 1/2009 | Ahn et al. |
| 7,718,420 B2 | 5/2010 | Kim et al. |
| 7,790,458 B2 | 9/2010 | Xu et al. |
| 7,893,315 B2 | 2/2011 | Chung et al. |
| 8,252,587 B2 | 8/2012 | Fong et al. |
| 8,263,403 B2 | 9/2012 | Perry et al. |
| 8,372,642 B2 | 2/2013 | Rajesh et al. |
| 8,525,943 B2 | 9/2013 | Nakano et al. |
| 8,546,141 B2 | 10/2013 | Nakauchi et al. |
| 8,933,071 B2 | 1/2015 | Crispino et al. |
| 9,012,221 B2 | 4/2015 | Baruch et al. |
| 9,074,186 B2 | 7/2015 | Murphy et al. |
| 9,200,254 B2 | 12/2015 | Eto et al. |
| 2003/0153082 A1 | 8/2003 | Bhatia |
| 2004/0136973 A1 | 7/2004 | Humerman et al. |
| 2007/0243608 A1 | 10/2007 | Kyba et al. |
| 2010/0248361 A1 | 9/2010 | Lasky et al. |
| 2010/0316613 A1 | 12/2010 | Upton et al. |
| 2011/0086424 A1 | 4/2011 | Lanza et al. |
| 2011/0280861 A1 | 11/2011 | Scadden et al. |
| 2012/0238020 A1 | 9/2012 | Mitchell et al. |
| 2012/0282228 A1 | 11/2012 | Bhasin |
| 2012/0315338 A1 | 12/2012 | Li et al. |
| 2013/0210141 A1 | 8/2013 | Rajesh et al. |
| 2014/0037600 A1* | 2/2014 | Yu .......................... A61K 35/28 424/93.21 |
| 2014/0086883 A1 | 3/2014 | Poncz et al. |
| 2014/0127815 A1 | 5/2014 | Eto et al. |
| 2014/0205582 A1 | 7/2014 | Karzunky et al. |
| 2014/0227780 A1 | 8/2014 | Nishino et al. |
| 2014/0315760 A1 | 10/2014 | Ratner et al. |
| 2015/0004694 A1 | 1/2015 | Mayaudon et al. |
| 2015/0079030 A1 | 3/2015 | Moore |
| 2015/0087065 A1 | 3/2015 | Haecker |
| 2015/0111296 A1 | 4/2015 | Pedersen et al. |
| 2015/0203819 A1 | 7/2015 | Murphy et al. |
| 2015/0275176 A1 | 10/2015 | Kobayashi et al. |
| 2015/0335682 A1 | 11/2015 | Murphy et al. |
| 2015/0361398 A1 | 12/2015 | Sandler et al. |
| 2016/0002586 A1 | 1/2016 | Mitchell |
| 2016/0002599 A1 | 1/2016 | Eto |
| 2016/0139124 A1 | 5/2016 | Newman et al. |
| 2016/0145573 A1 | 5/2016 | Liu et al. |
| 2016/0168540 A1 | 6/2016 | Hirata et al. |
| 2016/0177265 A1 | 6/2016 | Matsubara et al. |
| 2016/0206783 A1 | 7/2016 | Dietz et al. |
| 2016/0235889 A1 | 8/2016 | Pallotta et al. |
| 2016/0272941 A1 | 9/2016 | Baruch et al. |

FOREIGN PATENT DOCUMENTS

| | | | |
|---|---|---|---|
| WO | 2006/001954 | 1/2006 | |
| WO | 2008/151386 | 12/2008 | |
| WO | 2008/151390 | 12/2008 | |
| WO | WO 2010/099539 | 9/2010 | |
| WO | WO 2012/061146 | 5/2012 | |
| WO | WO-2012061146 A1 * | 5/2012 | ........... C12N 5/0644 |
| WO | 2014/138485 | 9/2014 | |
| WO | 2015/179301 | 11/2015 | |
| WO | 2015/191632 | 12/2015 | |
| WO | 2016/160860 | 10/2016 | |

OTHER PUBLICATIONS

Drayer et al (British Journal of Immunology, 109: 776-784, 2000).*

(Continued)

*Primary Examiner* — Anoop K Singh
*Assistant Examiner* — Magdalene K Sgagias
(74) *Attorney, Agent, or Firm* — Greenberg Traurig, LLP; Roman Fayerberg; Natalie Salem

(57) ABSTRACT

This invention relates to the forward programming of pluripotent stem cells (PSCs) into megakaryocyte (MK) progenitor cells using the transcription factors GATA1, FLI1 and TAL1. Methods of producing megakaryocyte (MK) progenitor cells and subsequently differentiating them into mature megakaryocytes are provided.

15 Claims, 17 Drawing Sheets
Specification includes a Sequence Listing.

(56) References Cited

OTHER PUBLICATIONS

Takayama et al (Blood 2008 111:5298-5306, 2008.*
Takayama et al (Cell. Mol. Life Sci. (2012) 69:3419-3428).*
Guo et al (Blood., 114:2097-2106, 2009).*
Takayama and Eto (Cell. Mol. Life Sci, 69: 3419-3428, published on line Apr. 24, 2012) (Year: 2012).*
Lu et al (Cell Research, 21: 530-545, 2011) (Year: 2011).*
Chang et al (Journal of Thrombosis and Haemostasis, 5 (Suppl. 1): 318-327, 2007). (Year: 2007).*
Dore et al (Blood, 118(2): 231-239, 2011). (Year: 2011).*
Elagib et al ((Blood. 2003; 101:4333-4341). (Year: 2003).*
Takayama, Naoya et al: "In vitro generation of megakaryocytes and platelets from human embryonic stem cells and induced pluripotent stem cells", Microbial Metabolic Engineering : Methods and Protocols; [Methods in Molecular Biology ; 834], Humana Press, US, vol. 788, Jan. 1, 2012 (Jan. 1, 2012), pp. 205-217.
Pimanda John et al: "Gata2, Fli1, and Scl form a recursively wired gene-regulatory circuit during early hematopoietic development", Proceedings of The National Academy of Sciences—PNAS, National Academy of Sciences, US, vol. 104, No. 45, Nov. 1, 2007 (Nov. 1, 2007), pp. 17692-17697.
Tijssen, Marloes et al: "Genome-wide Analysis of Simultaneous GATA 1/2, RUNX1, FLI1, and SCL Binding in Megakaryocytes Identifies Hematopoietic Regulators", Developmental Cell, vol. 20, No. 5, May 2011, pp. 597-609.
Athanasiou, M. et al. "Increased Expression of the ETS-related Transcription Factor FLI-1/ERGB Correlates with and Can Induce the Megakaryocytic Phernotype", Cell Growth and Differentiation, vol. 7, 1525-1534, Nov. 1996.
Feng, R. et al. "PU. 1 and C/EBP α/β convert fibroblasts into macrophage-like cells" PNAS, vol. 105, No. 16, 6057-6062, Apr. 22, 2008.
Gou, Y. et al., "c-Myc-mediated control of cell fate in megakaryocyte-erythrocyte progenitors", Blood, vol. 114, No. 10, Sep. 3, 2009, pp. 2097-2106.
Iwasaki, H. et al. "GATA-1 Converts Lymphoid and Myelomonocytic Progenitors into the Megakaryocyte/Erythrocyte Lineages", Immunity , vol. 19, 451-462, Sep. 2003.
Lu, S. et al., "Platelets generated from human embryonic stem cells are functional in vitro and in the microcirculation of living mice", Cell Research (2011) 21:530-545.
Moreau, T. et al., "Large-scale production of megakaryocytes from human pluripotent sten cells by chemically defined forward programming", Nature Comminications, 7:11201, pp. 1-15, Apr. 7, 2016.
Pang, Z. et al. "Induction of human neuronal cells by defined transcription factors", Nature, 2011; 476:220-223.
Szabo, E. et al., "Direct conversion of human fibroblasts to multilineage blood progenitors", Nature, vol. 468, pp. 521-528, Nov. 25, 2010.
Takayama, N. et al., "Pluripotent stem cells reveal the developmental biology of human megakaryocytes and provide a source of platelets for clinical application", Cellular and Molecular Life Sciences, vol. 69, pp. 3419-3428, 2012.
Takeuchi, J. et al., "Directed transdifferentiation of mouse mesoderm to heart tissue by defined factors", Nature, 459(7247): 708-711, Jun. 4, 2009.
Valtieri, M. et al., "Enforced TAL-1 Expression Stimulates Primitive, Erythroid, and Megakaryocytic Progenitors byut Blocks the Granulopoietic Differentiation Program", Cancer Research 1998; 58: 562-569.
Altschul, S. et al., "Basic Local Alignment Search Tool," Journal of Molecular Biology, vol. 215, Issue 3, pp. 403-410, Oct. 5, 1990.
Barbaric, I., et al., "High-Content Screening of Small Compounds on Human Embryonic Stem Cells," Biochemical Society Transactions, vol. 38, Part 4, pp. 1046-1050, Aug. 2010.
Bernardo, A. et al., "BRACHYURY and CDX2 Mediate BMP-Induced Differentiation of Huyman and Mouse Pluripotent Stem Cells into Embryonic and Extraembryonic Lineages," Cell Stem Cell, vol. 9, pp. 144-155, Aug. 5, 2011.

Carpenter, M. et al., "Characterization and Differentiation of Human Embryonic Stem Cells," Cloning and Stem Cells, vol. 5, No. 1, pp. 79-88, Mar. 2003.
Chang, Y., et al., "From Hematopoietic Stem Cells to Platelets," Journal of Thrombosis and Haemostasis, vol. 5, Supplement 1, pp. 318-327, Feb. 2007.
Chou, b., et al., "Efficient Human iPS Cell Derivation by a Non-Integrating Plasmid from Blood Cells with Unique Epigenetic and Gene Expression Signatures," Cell Research, vol. 21, No. 3, pp. 518-529, Mar. 2011.
Chung, Y., et al., "Human Embryonic Stem Cell Lines Generated without Embryo Destruction," Cell Stem Cell 2, pp. 113-117, Feb. 2008.
Cowan, C. et al., "Derivation of Embryonic Stem-Cell Lines from Human Blastocysts," New England Journal of Medicine, vol. 350, Issue 13, pp. 1353-1356, Mar. 25, 2004.
Loh, y. et al., "Reprogramming of T Cells from Human Peripheral Blood," Cell Stem Cell, vol. 7, pp. 15-19, Jul. 2, 2010.
Gage, F., "Isolation, Characterization, and Use of Stem Cells from the CNS," Annual Review of Neuroscience, vol. 18, pp. 159-192, Jan. 1, 1995.
Gaur, M., "Megakaryocytes Derived from Human Embryonic Stem Cells: a Genetically Tractable System to Study Megakaryocytopoiesis and Integrin Function," Journal of Thrombosis and Haemostasis, vol. 4, Issue 2, pp. 436-442, Jan. 13, 2006.
Gottlieb, D., "Large-Scale Sources of Neural Stem Cells," Annual Review of Neuroscience, vol. 25, pp. 381-407, Mar. 2002.
Gray, K. et al., "Genenames.org: The HGNC Resources in 2013," Nucleic Acids Research, vol. 41, Database Issue, pp. D545-D552, 2013.
Han, D. et al., "Direct Reprogramming of Fibroblasts into Epiblast Stem Cells," Nature Cell Biology, vol. 13, No. 1, pp. 66-71, Jan. 2011.
Hanna, J. et al., "Human Embryonic Stem Cells with Biological and Epigenetic Characteristics Similar to Those of Mouse ESCs" Proceedings of the National Academy of Sciences, vol. 107, No. 20, pp. 9222-9227, May 18, 2010.
Helgason, C., "Basic Cell Culture Protocols," Third Edition, vol. 290, pp. 1-365.
Ho, W., et al., "In Vitro Methods for Generating CD8+ T-Cell Clones for Immunotherapy from the Naïve Repertoire," Journal of Immunological Methods, vol. 310, pp. 40-52, Jan. 2006.
Hu, Z. et al., "VisANT: Data-Integrating Visual Framework for Biological Networks and Modules," Nucleic Acids Research, vol. 33, Web Server Issue, pp. W352-W357.
Joannides, A., et al., "Automated Mechanical Passaging: A Novel and Efficient Method for Human Embryonic Stem Cell Expansion," Stem Cells, vol. 24, Issue 2, pp. 230-235, Feb. 2006.
Johansson, B. et al., "Evidence for Involvement of Activin A and Bone Morphogenetic Protein 4 in Mammalian Mesoderm and Hematopoietic Development," Molecular and Cellular Biology, vol. 15, No. 1, pp. 141-151, Jan. 1995.
Kaushansky, K., "Historical Review: Megakaryopoiesis and Thrombopoiesis", Blood Journal, vol. 111, No. 3, pp. 981-986, Feb. 1, 2008.
Keller, G., "Embryonic Stem Cell Differentiation: Emergence of a New Era in Biology and Medicine", Genes & Development, vol. 19, pp. 1129-1155, May 15, 2005.
Kim, D., et al., "Generation of Human Induced Pluripotent Stem Cells by Direct Delivery of Reprogramming Proteins," Cell Stem Cell, vol. 4, Issue 6, pp. 472-476, Jun. 5, 2009.
Kim, D., et al., "Pluripotent stem cells induced from adult neural stem cells by reprogramming with two factors," Nature, vol. 454, pp. 646-650, Jul. 31, 2008.
Klimanskaya, I. et al., "Human Embryonic Stem Cells Derived From Single Blastomeres," Nature vol. 444, pp. 481-485, Nov. 23, 2006.
Klimanskaya, I. et al., "Human Embryonic Stem Cells Derived Without Feeder Cells," Lancet, vol. 365, pp. 1636-1641, May 7, 2005.
Klimanskaya, I. et al., "Embryonic Stem Cells from Blastomeres Maintaining Embryo Viability," Chapter 8 of Embryonic Stem Cells from Blastomeres Maintaining Embryo Viability, pp. 84-92.

(56) References Cited

OTHER PUBLICATIONS

Ludwig, T., et al., "Derivation of Human Embryonic Stem Cells in Defined Conditions," Nature Biotechnology, vol. 24, No. 2, pp. 185-187, Feb. 2006.
Murry, C., et al., "Differentiation of Embryonic Stem Cells to Clinically Relevant Populations: Lessons from Embryonic Development," Cell, vol. 132, pp. 661-680, Feb. 22, 2008.
Needleman, S. et al., "A General Method Applicable to the Search for Similarities in the Amino Acid Sequence of Two Proteins," Journal of Molecular Biology, vol. 48, Issue 3, pp. 443-453, Mar. 28, 1970.
Nichols, J. et al., "Naïve and Primed Pluripotent States," Cell Stem Cell, vol. 4, pp. 487-492, Jun. 5, 2009.
Okita, K. et al., "Generation of Germline-Competent Induced Pluripotent Stem Cells," Nature, vol. 448, pp. 313-317, Jul. 19, 2007.
Staerk, J. et al., "Reprogramming of Human Peripheral Blood Cells to Induced Pluripotent Stem Cells," Cell Stem Cell, vol. 7, pp. 20-24, Jul. 2, 2010.
Park, I., "Reprogramming of Human Somatic Cells to Pluripotency with Defined Factors," Nature, vol. 451, pp. 141-146, Jan. 10, 2008.
Pearson, W. et al., "Improved Tools for Biological Sequence Comparison," Proceedings of the National Academy of Sciences, vol. 85, pp. 2444-2448, Apr. 1988.
Pick, M., et al., "Generation of Megakaryocytic Progenitors from Human Embryonic Stem Cells in a Feeder and Serum-Free Medium," Public Library of Science ONE, vol. 8, Issue 2, pp. 1-11, Feb. 2013.
Reubinoff, B. et al., "Embryonic Stem Cell Lines from Human Blastocysts: Somatic Differentiation in Vitro," Nature Biotechnology, vol. 18, pp. 399-404, Apr. 18, 2000.
Sidhu, K., "New Approaches for the Generation of Induced Pluripotent Stem Cells," Expert Opinion on Biological Therapy, vol. 11, Issue 5, May 2011.
Silva, J. et al., "Nanog is the Gateway to the Pluripotent Ground State," Cell, vol. 138, No. 4, pp. 722-737, Aug. 21, 2009.
Smith, T. et al., "Identification of Common Molecular Subsequences," Journal of Molecular Biology, vol. 147, Issue 1, pp. 195-197, Mar. 25, 1981.
Takahashi, K., et al., Induction of Pluripotent Stem Cells from Adult Human Fibroblasts by Defined Factors, Cell, vol. 131, pp. 861-872, Nov. 30, 2007.
Taylor, C., "Banking on human embryonic stem cells: estimating the number of donor cell lines needed for HLA matching", The Lancet, vol. 366, Issue 9502, pp. 2019-2025, Dec. 10, 2005.
Tesar, P. et al., "New Cell Lines from Mouse Epiblast Share Defining Features with Human Embryonic Stem Cells," Nature, vol. 448, pp. 196-199, Jul. 12, 2007.
Thomson, J. et al., "Embryonic Stem Cell Lines Derived from Human Blastocysts," Science, vol. 282, pp. 1145-1147, 1998.
Vallier, I., et al., "Nodal Inhibits Differentiation of Human Embryonic Stem Cells Along the Neuroectodermal Default Pathway," Developmental Biology, vol. 275, pp. 402-421, Aug. 2004.
Vallier, I., et al., "Signaling Pathways Controlling Pluripotency and Early Cell Fate Decisions of Human Induced Pluripotent Stem Cells," Stem Cells, vol. 27, Issue 11, pp. 2655-2666, Nov. 2009.
Warren, L., et al., "Highly Efficient Reprogramming to Pluripotency and Directed Differentiation of Human Cells with Synthetic Modified mRNA," Cell Stem Cell, vol. 7, No. 5, pp. 618-630, Nov. 5, 2010.
Watkins, N. "A HaemAtlas: Characterizing Gene Expression in Differentiated Human Blood Cells," Blood, vol. 113, No. 13, e1-e9, May 7, 2009.
Woltjen, K., et al., "PiggyBac Transposition Reprograms Fibroblasts to Induced Pluripotent Stem Cells," Nature, vol. 458, (7239), pp. 766-770, Apr. 9, 2009.
Yamanaka, S., "Strategies and New Developments in the Generation of Patient-Specific Pluripotent Stem Cells", Cell Stem Cell, vol. 1, Issue 1, pp. 39-49, Jun. 7, 2007.
Takayama, N. et al., "Generation of functional platelets from human embryonic stem cells in vitro cia ES-sacs, VEGF-promoted structures that concentrate hematopoietic progenitors", Blood, vol. 111, No. 11, Jun. 1, 2008, pp. 5298-5306.
Takayama, N. et al., "Transient Activation of c-MYC Expression is Critical for Efficient Platelet Generation from Human Induced Pluripotent Stem Cells," Journal of Experimental Medicine, vol. 207, No. 13, pp. 2817-2830, Nov. 2010.
Takayama, N. et al., "Pluripotent stem cells reveal the developmental biology of human megakaryocytes and provide a source of platelets for clinical application", Cellular and Molecular Life Sciences, vol. 69, pp. 3419-3428, Apr. 2012.
Tijssen, M. et al., "Genome-wide Analysis of Simultaneous GATA1/2, RUNX1, FLI1, and SCL Binding in Megakaryocytes Identifies Hematopoietic Regulators", Developmental Cell, vol. 20, No. 2, pp. 597-609, May 17, 2011.
Wain, H., et al., "Guidelines for Human Gene Nomenclature," Genomics, vol. 79, No. 4, pp. 464-470, Apr. 2002.
Yamanaka, S., "Patient-Specific Pluripotent Stem Cells Become Even More Accessible", Cell Stem Cell, vol. 7, Issue 1, pp. 1-2, Jul. 2, 2010.
Ying, Q. et al., "The Ground State of Embryonic Stem Cell Self-Renewal," Nature, vol. 453, pp. 519-523, May 22, 2008.
Yu, J. et al., "Induced Pluripotent Stem Cell Lines Derived from Human Somatic Cells," Science, vol. 318, pp. 1917-1920, Dec. 21, 2007.
Zhang, P., et al., "Engineered Zinc-Finger Proteins Can Compensate Genetic Haploinsufficiency by Transcriptional Activation of the Wild-Type Allele: Application to Willams-Beuren Syndrome and Supravalvular Aortic Stenosis," Human Gene Therapy, vol. 23, pp. 1186-1199, Nov. 2012.
Zhou, H. et al., "Generation of Induced Pluripotent Stem Cells Using Recombinant Proteins," Cell Stem Cell, vol. No. 5, pp. 381-384, May 8, 2009.

\* cited by examiner

CD41a+

CD41a-
no colonies

| Candidate Rank | Symbol |
|---|---|
| 1 | GATA1 |
| 2 | IKZF1 |
| 3 | SPI1 |
| 4 | HOXA5 |
| 5 | MEIS1 |
| 6 | FLI1 |
| 7 | PBX1 |
| 8 | ZBTB16 |
| 9 | ZNFN1A3 |
| 10 | TAL1 |
| 11 | NFATC1 |
| 12 | TSC22D3 |
| 13 | KLF1 |
| 14 | ZFPM2 |
| 15 | STAT4 |
| 16 | NFE2 |
| 17 | ZNF467 |
| 18 | ZFPM1 |
| 19 | RELA |
| 20 | MEF2C |
| 21 | RUNX3 |
| 22 | RUNX1 |
| 23 | ZBTB7A |
| 24 | HSF1 |
| 25 | MECOM |
| 26 | SATB1 |
| 27 | PLAGL1 |
| 28 | MAX |
| 29 | HOXB2 |
| 30 | CLOCK |
| 31 | ZNF385 |
| 32 | XPA |
| 33 | NFIC |
| 34 | MAFG |
| 35 | WT1 |
| 36 | GFI1B |
| 37 | CNOT7 |
| 38 | BATF |
| 39 | ZNF280D |
| 40 | TBXA2R |
| 41 | PRDM8 |
| 42 | ZNF557 |
| 43 | TSH21 |
| 44 | ZNF580 |
| 45 | ZNF439 |
| 46 | RBM38 |

Table 1

Figure 17

SEQUENCE LISTING

<160> NUMBER OF SEQ ID NOS: 16

<210> SEQ ID NO 1
<211> LENGTH: 413
<212> TYPE: PRT
<213> ORGANISM: Homo sapiens

<400> SEQUENCE: 1

Met Glu Phe Pro Gly Leu Gly Ser Leu Gly Thr Ser Glu Pro Leu Pro
1               5                   10                  15

Gln Phe Val Asp Pro Ala Leu Val Ser Ser Thr Pro Glu Ser Gly Val
            20                  25                  30

Phe Phe Pro Ser Gly Pro Glu Gly Leu Asp Ala Ala Ser Ser Thr
             35                  40                  45

Ala Pro Ser Thr Ala Thr Ala Ala Ala Ala Leu Ala Tyr Tyr Arg
 50                  55                  60

Asp Ala Glu Ala Tyr Arg His Ser Pro Val Phe Gln Val Tyr Pro Leu
 65                  70                  75                  80

Leu Asn Cys Met Glu Gly Ile Pro Gly Gly Ser Pro Tyr Ala Gly Trp
                 85                  90                  95

Ala Tyr Gly Lys Thr Gly Leu Tyr Pro Ala Ser Thr Val Cys Pro Thr
                100                 105                 110

Arg Glu Asp Ser Pro Pro Gln Ala Val Glu Asp Leu Asp Gly Lys Gly
                115                 120                 125

Ser Thr Ser Phe Leu Glu Thr Leu Lys Thr Glu Arg Leu Ser Pro Asp
 130                 135                 140

Leu Leu Thr Leu Gly Pro Ala Leu Pro Ser Ser Leu Pro Val Pro Asn
 145                 150                 155                 160

Ser Ala Tyr Gly Gly Pro Asp Phe Ser Ser Thr Phe Phe Ser Pro Thr
                 165                 170                 175

Gly Ser Pro Leu Asn Ser Ala Ala Tyr Ser Ser Pro Lys Leu Arg Gly
                180                 185                 190

Thr Leu Pro Leu Pro Pro Cys Glu Ala Arg Glu Cys Val Asn Cys Gly
                195                 200                 205

Ala Thr Ala Thr Pro Leu Trp Arg Arg Asp Arg Thr Gly His Tyr Leu
                210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
                260                 265                 270

Ala Ser Gly Asp Pro Val Cys Asn Ala Cys Gly Leu Tyr Tyr Lys Leu
                275                 280                 285

His Gln Val Asn Arg Pro Leu Thr Met Arg Lys Asp Gly Ile Gln Thr
                290                 295                 300

Arg Asn Arg Lys Ala Ser Gly Lys Gly Lys Lys Lys Arg Gly Ser Ser
305                 310                 315                 320

Leu Gly Gly Thr Gly Ala Ala Glu Gly Pro Ala Gly Gly Phe Met Val
                325                 330                 335

Val Ala Gly Gly Ser Gly Ser Gly Asn Cys Gly Glu Val Ala Ser Gly
                340                 345                 350

Leu Thr Leu Gly Pro Pro Gly Thr Ala His Leu Tyr Gln Gly Leu Gly
                355                 360                 365

Pro Val Val Leu Ser Gly Pro Val Ser His Leu Met Pro Phe Pro Gly
                370                 375                 380

Pro Leu Leu Gly Ser Pro Thr Gly Ser Phe Pro Thr Gly Pro Met Pro
385                 390                 395                 400

Pro Thr Thr Ser Thr Thr Val Val Ala Pro Leu Ser Ser
                405                 410

<210> SEQ ID NO 2
<211> LENGTH: 452
<212> TYPE: PRT
<213> ORGANISM: Homo sapiens

<400> SEQUENCE: 2

```
Met Asp Gly Thr Ile Lys Glu Ala Leu Ser Val Val Ser Asp Gln
1               5                   10                  15

Ser Leu Phe Asp Ser Ala Tyr Gly Ala Ala His Leu Pro Lys Ala
            20                  25                  30

Asp Met Thr Ala Ser Gly Ser Pro Asp Tyr Gly Gln Pro His Lys Ile
        35                  40                  45

Asn Pro Leu Pro Pro Gln Gln Glu Trp Ile Asn Gln Pro Val Arg Val
50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
                85                  90                  95

Ser Asn Pro Met Asn Tyr Asn Ser Tyr Met Asp Glu Lys Asn Gly Pro
                100                 105                 110

Pro Pro Pro Asn Met Thr Thr Asn Glu Arg Arg Val Ile Val Pro Ala
            115                 120                 125

Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415
```

```
Gly Ala Ala Ser Gln Tyr Trp Thr Ser Pro Thr Gly Gly Ile Tyr Pro
                420                 425                 430

Asn Pro Asn Val Pro Arg His Pro Asn Thr His Val Pro Ser His Leu
                435                 440                 445

Gly Ser Tyr Tyr
        450

<210> SEQ ID NO 3
<211> LENGTH: 331
<212> TYPE: PRT
<213> ORGANISM: Homo sapiens

<400> SEQUENCE: 3

Met Thr Glu Arg Pro Ser Glu Ala Ala Arg Ser Asp Pro Gln Leu
1               5                   10                  15

Glu Gly Arg Asp Ala Ala Glu Ala Ser Met Ala Pro Pro His Leu Val
                20                  25                  30

Leu Leu Asn Gly Val Ala Lys Glu Thr Ser Arg Ala Ala Ala Ala Glu
                35                  40                  45

Pro Pro Val Ile Glu Leu Gly Ala Arg Gly Gly Pro Gly Gly Gly Pro
50                  55                  60

Ala Gly Gly Gly Gly Ala Ala Arg Asp Leu Lys Gly Arg Asp Ala Ala
65                  70                  75                  80

Thr Ala Glu Ala Arg His Arg Val Pro Thr Thr Glu Leu Cys Arg Pro
                85                  90                  95

Pro Gly Pro Ala Pro Ala Pro Ala Pro Ala Ser Val Thr Ala Glu Leu
                100                 105                 110

Pro Gly Asp Gly Arg Met Val Gln Leu Ser Pro Pro Ala Leu Ala Ala
                115                 120                 125

Pro Ala Ala Pro Gly Arg Ala Leu Leu Tyr Ser Leu Ser Gln Pro Leu
                130                 135                 140

Ala Ser Leu Gly Ser Gly Phe Phe Gly Glu Pro Asp Ala Phe Pro Met
145                 150                 155                 160

Phe Thr Thr Asn Asn Arg Val Lys Arg Arg Pro Ser Pro Tyr Glu Met
                165                 170                 175

Glu Ile Thr Asp Gly Pro His Thr Lys Val Val Arg Arg Ile Phe Thr
                180                 185                 190

Asn Ser Arg Glu Arg Trp Arg Gln Gln Asn Val Asn Gly Ala Phe Ala
                195                 200                 205

Glu Leu Arg Lys Leu Ile Pro Thr His Pro Pro Asp Lys Lys Leu Ser
                210                 215                 220

Lys Asn Glu Ile Leu Arg Leu Ala Met Lys Tyr Ile Asn Phe Leu Ala
225                 230                 235                 240

Lys Leu Leu Asn Asp Gln Glu Glu Glu Gly Thr Gln Arg Ala Lys Thr
                245                 250                 255

Gly Lys Asp Pro Val Val Gly Ala Gly Gly Gly Gly Gly Gly Gly Gly
                260                 265                 270

Gly Gly Ala Pro Pro Asp Asp Leu Leu Gln Asp Val Leu Ser Pro Asn
                275                 280                 285

Ser Ser Cys Gly Ser Ser Leu Asp Gly Ala Ala Ser Pro Asp Ser Tyr
                290                 295                 300

Thr Glu Glu Pro Ala Pro Lys His Thr Ala Arg Ser Leu His Pro Ala
305                 310                 315                 320

Met Leu Pro Ala Ala Asp Gly Ala Gly Pro Arg
                325                 330
```

-continued

```
<210> SEQ ID NO 4
<211> LENGTH: 718
<212> TYPE: PRT
<213> ORGANISM: Homo sapiens

<400> SEQUENCE: 4

Met Leu Met Thr Leu Glu Met Thr Glu Leu Thr Asp Pro His His Thr
1               5                   10                  15

Met Gly Asp Tyr Lys Val Ala His Pro Gln Asp Pro His His Pro Ser
            20                  25                  30

Glu Lys Pro Val Ile His Cys His Lys Cys Gly Glu Pro Cys Lys Gly
        35                  40                  45

Glu Val Leu Arg Val Gln Thr Lys His Phe His Ile Lys Cys Phe Thr
    50                  55                  60

Cys Lys Val Cys Gly Cys Asp Leu Ala Gln Gly Gly Phe Phe Ile Lys
65                  70                  75                  80

Asn Gly Glu Tyr Leu Cys Thr Leu Asp Tyr Gln Arg Met Tyr Gly Thr
                85                  90                  95

Arg Cys His Gly Cys Gly Glu Phe Val Glu Gly Glu Val Val Thr Ala
            100                 105                 110

Leu Gly Lys Thr Tyr His Pro Asn Cys Phe Ala Cys Thr Ile Cys Lys
        115                 120                 125

Arg Pro Phe Pro Pro Gly Asp Arg Val Thr Phe Asn Gly Arg Asp Cys
    130                 135                 140

Leu Cys Gln Leu Cys Ala Gln Pro Met Ser Ser Pro Lys Glu Thr
145                 150                 155                 160

Thr Phe Ser Ser Asn Cys Ala Gly Cys Gly Arg Asp Ile Lys Asn Gly
                165                 170                 175

Gln Ala Leu Leu Ala Leu Asp Lys Gln Trp His Leu Gly Cys Phe Lys
            180                 185                 190

Cys Lys Ser Cys Gly Lys Val Leu Thr Gly Glu Tyr Ile Ser Lys Asp
        195                 200                 205

Gly Ala Pro Tyr Cys Glu Lys Asp Tyr Gln Gly Leu Phe Gly Val Lys
    210                 215                 220

Cys Glu Ala Cys His Gln Phe Ile Thr Gly Lys Val Leu Glu Ala Gly
225                 230                 235                 240

Asp Lys His Tyr His Pro Ser Cys Ala Arg Cys Ser Arg Cys Asn Gln
                245                 250                 255

Met Phe Thr Glu Gly Glu Glu Met Tyr Leu Gln Gly Ser Thr Val Trp
            260                 265                 270

His Pro Asp Cys Lys Gln Ser Thr Lys Thr Glu Glu Lys Leu Arg Pro
        275                 280                 285

Thr Arg Thr Ser Ser Glu Ser Ile Tyr Ser Arg Pro Gly Ser Ser Ile
    290                 295                 300

Pro Gly Ser Pro Gly His Thr Ile Tyr Ala Lys Val Asp Asn Glu Ile
305                 310                 315                 320

Leu Asp Tyr Lys Asp Leu Ala Ala Ile Pro Lys Val Lys Ala Ile Tyr
                325                 330                 335

Asp Ile Glu Arg Pro Asp Leu Ile Thr Tyr Gly Pro Phe Tyr Thr Ser
            340                 345                 350

Gly Tyr Asp Asp Lys Gln Glu Arg Gln Ser Leu Gly Glu Ser Pro Arg
        355                 360                 365

Thr Leu Ser Pro Thr Pro Ser Ala Glu Gly Tyr Gln Asp Val Arg Asp
    370                 375                 380
```

```
Arg Met Ile His Arg Ser Thr Ser Gln Gly Ser Ile Asn Ser Pro Val
385                 390                 395                 400

Tyr Ser Arg His Ser Tyr Thr Pro Thr Thr Ser Arg Ser Pro Gln His
            405                 410                 415

Phe His Arg Pro Gly Asn Glu Pro Ser Ser Gly Arg Asn Ser Pro Leu
            420                 425                 430

Pro Tyr Arg Pro Asp Ser Arg Pro Leu Thr Pro Thr Tyr Ala Gln Ala
            435                 440                 445

Pro Lys His Phe His Val Pro Asp Gln Gly Ile Asn Ile Tyr Arg Lys
            450                 455                 460

Pro Pro Ile Tyr Lys Gln His Ala Ala Leu Ala Ala Gln Ser Lys Ser
465                 470                 475                 480

Ser Glu Asp Ile Ile Lys Phe Ser Lys Phe Pro Ala Ala Gln Ala Pro
                485                 490                 495

Asp Pro Ser Glu Thr Pro Lys Ile Glu Thr Asp His Trp Pro Gly Pro
            500                 505                 510

Pro Ser Phe Ala Val Val Gly Pro Asp Met Lys Arg Arg Ser Ser Gly
            515                 520                 525

Arg Glu Glu Asp Asp Glu Glu Leu Leu Arg Arg Gln Leu Gln Glu
            530                 535                 540

Glu Gln Leu Met Lys Leu Asn Ser Gly Leu Gly Gln Leu Ile Leu Lys
545                 550                 555                 560

Glu Glu Met Glu Lys Glu Ser Arg Glu Arg Ser Ser Leu Leu Ala Ser
                565                 570                 575

Arg Tyr Asp Ser Pro Ile Asn Ser Ala Ser His Ile Pro Ser Ser Lys
            580                 585                 590

Thr Ala Ser Leu Pro Gly Tyr Gly Arg Asn Gly Leu His Arg Pro Val
            595                 600                 605

Ser Thr Asp Phe Ala Gln Tyr Asn Ser Tyr Gly Asp Val Ser Gly Gly
            610                 615                 620

Val Arg Asp Tyr Gln Thr Leu Pro Asp Gly His Met Pro Ala Met Arg
625                 630                 635                 640

Met Asp Arg Gly Val Ser Met Pro Asn Met Leu Glu Pro Lys Ile Phe
                645                 650                 655

Pro Tyr Glu Met Leu Met Val Thr Asn Arg Gly Arg Asn Lys Ile Leu
            660                 665                 670

Arg Glu Val Asp Arg Thr Arg Leu Glu Arg His Leu Ala Pro Glu Val
            675                 680                 685

Phe Arg Glu Ile Phe Gly Met Ser Ile Gln Glu Phe Asp Arg Leu Pro
            690                 695                 700

Leu Trp Arg Arg Asn Asp Met Lys Lys Lys Ala Lys Leu Phe
705                 710                 715

<210> SEQ ID NO 5
<211> LENGTH: 323
<212> TYPE: PRT
<213> ORGANISM: Homo sapiens

<400> SEQUENCE: 5

Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
                20                  25                  30

Asp Lys Phe Cys Ala Asn Thr Cys Val Glu Cys Arg Lys Pro Ile Gly
            35                  40                  45
```

```
Ala Asp Ser Lys Glu Val His Tyr Lys Asn Arg Phe Trp His Asp Thr
 50                  55                  60

Cys Phe Arg Cys Ala Lys Cys Leu His Pro Leu Ala Asn Glu Thr Phe
 65                  70                  75                  80

Val Ala Lys Asp Asn Lys Ile Leu Cys Asn Lys Cys Thr Thr Arg Glu
                 85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
            115                 120                 125

Cys Ser Asn Cys Lys Gln Val Ile Gly Thr Gly Ser Phe Phe Pro Lys
130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Asp Cys Phe Val Cys Val Thr Cys Ser
            180                 185                 190

Lys Lys Leu Ala Gly Gln Arg Phe Thr Ala Val Glu Asp Gln Tyr Tyr
            195                 200                 205

Cys Val Asp Cys Tyr Lys Asn Phe Val Ala Lys Cys Ala Gly Cys
210                 215                 220

Lys Asn Pro Ile Thr Gly Lys Arg Thr Val Ser Arg Val Ser His Pro
225                 230                 235                 240

Val Ser Lys Ala Arg Lys Pro Pro Val Cys His Gly Lys Arg Leu Pro
                245                 250                 255

Leu Thr Leu Phe Pro Ser Ala Asn Leu Arg Gly Arg His Pro Gly Gly
            260                 265                 270

Glu Arg Thr Cys Pro Ser Trp Val Val Leu Tyr Arg Lys Asn Arg
            275                 280                 285

Ser Leu Ala Ala Pro Arg Gly Pro Gly Leu Val Lys Ala Pro Val Trp
            290                 295                 300

Trp Pro Met Lys Asp Asn Pro Gly Thr Thr Thr Ala Ser Thr Ala Lys
305                 310                 315                 320

Asn Ala Pro

<210> SEQ ID NO 6
<211> LENGTH: 429
<212> TYPE: PRT
<213> ORGANISM: Homo sapiens

<400> SEQUENCE: 6

Met Ala Ser Asn Ser Ile Phe Asp Ser Phe Pro Thr Tyr Ser Pro Thr
  1               5                  10                  15

Phe Ile Arg Asp Pro Ser Thr Ser Arg Arg Phe Thr Pro Pro Ser Pro
                 20                  25                  30

Ala Phe Pro Cys Gly Gly Gly Gly Lys Met Gly Glu Asn Ser Gly
             35                  40                  45

Ala Leu Ser Ala Gln Ala Ala Val Gly Pro Gly Gly Arg Ala Arg Pro
         50                  55                  60

Glu Val Arg Ser Met Val Asp Val Leu Ala Asp His Ala Gly Glu Leu
 65                  70                  75                  80

Val Arg Thr Asp Ser Pro Asn Phe Leu Cys Ser Val Leu Pro Ser His
                 85                  90                  95
```

```
Trp Arg Cys Asn Lys Thr Leu Pro Val Ala Phe Lys Val Val Ala Leu
                100                 105                 110

Gly Asp Val Pro Asp Gly Thr Val Val Thr Val Met Ala Gly Asn Asp
            115                 120                 125

Glu Asn Tyr Ser Ala Glu Leu Arg Asn Ala Ser Ala Val Met Lys Asn
        130                 135                 140

Gln Val Ala Arg Phe Asn Asp Leu Arg Phe Val Gly Arg Ser Gly Arg
145                 150                 155                 160

Gly Lys Ser Phe Thr Leu Thr Ile Thr Val Phe Thr Asn Pro Thr Gln
                165                 170                 175

Val Ala Thr Tyr His Arg Ala Ile Lys Val Thr Val Asp Gly Pro Arg
            180                 185                 190

Glu Pro Arg Arg His Arg Gln Lys Leu Glu Asp Gln Thr Lys Pro Phe
        195                 200                 205

Pro Asp Arg Phe Gly Asp Leu Glu Arg Leu Arg Met Arg Val Thr Pro
210                 215                 220

Ser Thr Pro Ser Pro Arg Gly Ser Leu Ser Thr Thr Ser His Phe Ser
225                 230                 235                 240

Ser Gln Pro Gln Thr Pro Ile Gln Gly Thr Ser Glu Leu Asn Pro Phe
                245                 250                 255

Ser Asp Pro Arg Gln Phe Asp Arg Ser Phe Pro Thr Leu Pro Thr Leu
            260                 265                 270

Thr Glu Ser Arg Phe Pro Asp Pro Arg Met His Tyr Pro Gly Ala Met
        275                 280                 285

Ser Ala Ala Phe Pro Tyr Ser Ala Thr Pro Ser Gly Thr Ser Ile Ser
290                 295                 300

Ser Leu Ser Val Ala Gly Met Pro Ala Thr Ser Arg Phe His His Thr
305                 310                 315                 320

Tyr Leu Pro Pro Pro Tyr Pro Gly Ala Pro Gln Asn Gln Ser Gly Pro
                325                 330                 335

Phe Gln Ala Asn Pro Ser Pro Tyr His Leu Tyr Gly Thr Ser Ser
            340                 345                 350

Gly Ser Tyr Gln Phe Ser Met Val Ala Gly Ser Ser Ser Gly Gly Asp
        355                 360                 365

Arg Ser Pro Thr Arg Met Leu Ala Ser Cys Thr Ser Ser Ala Ala Ser
370                 375                 380

Val Ala Ala Gly Asn Leu Met Asn Pro Ser Leu Gly Gly Gln Ser Asp
385                 390                 395                 400

Gly Val Glu Ala Asp Gly Ser His Ser Asn Ser Pro Thr Ala Leu Ser
                405                 410                 415

Thr Pro Gly Arg Met Asp Glu Ala Val Trp Arg Pro Tyr
            420                 425

<210> SEQ ID NO 7
<211> LENGTH: 508
<212> TYPE: PRT
<213> ORGANISM: Homo sapiens

<400> SEQUENCE: 7

Met Tyr Ser Ser Pro Leu Cys Leu Thr Gln Asp Glu Phe His Pro Phe
1               5                   10                  15

Ile Glu Ala Leu Leu Pro His Val Arg Ala Phe Ala Tyr Thr Trp Phe
            20                  25                  30

Asn Leu Gln Ala Arg Lys Arg Lys Tyr Phe Lys Lys His Glu Lys Arg
        35                  40                  45
```

Met Ser Lys Asp Glu Glu Arg Ala Val Lys Asp Glu Leu Leu Gly Glu
 50                  55                  60

Lys Pro Glu Val Lys Gln Lys Trp Ala Ser Arg Leu Leu Ala Lys Leu
 65                  70                  75                  80

Arg Lys Asp Ile Arg Pro Glu Cys Arg Glu Asp Phe Val Leu Ser Ile
                 85                  90                  95

Thr Gly Lys Lys Ala Pro Gly Cys Val Leu Ser Asn Pro Asp Gln Lys
            100                 105                 110

Gly Lys Met Arg Arg Ile Asp Cys Leu Arg Gln Ala Asp Lys Val Trp
            115                 120                 125

Arg Leu Asp Leu Val Met Val Ile Leu Phe Lys Gly Ile Pro Leu Glu
130                 135                 140

Ser Thr Asp Gly Glu Arg Leu Val Lys Ala Ala Gln Cys Gly His Pro
145                 150                 155                 160

Val Leu Cys Val Gln Pro His His Ile Gly Val Ala Val Lys Glu Leu
                165                 170                 175

Asp Leu Tyr Leu Ala Tyr Phe Val Arg Glu Arg Asp Ala Glu Gln Ser
            180                 185                 190

Gly Ser Pro Arg Thr Gly Met Gly Ser Asp Gln Glu Asp Ser Lys Pro
            195                 200                 205

Ile Thr Leu Asp Thr Thr Asp Phe Gln Glu Ser Phe Val Thr Ser Gly
210                 215                 220

Val Phe Ser Val Thr Glu Leu Ile Gln Val Ser Arg Thr Pro Val Val
225                 230                 235                 240

Thr Gly Thr Gly Pro Asn Phe Ser Leu Gly Glu Leu Gln Gly His Leu
                245                 250                 255

Ala Tyr Asp Leu Asn Pro Ala Ser Thr Gly Leu Arg Arg Thr Leu Pro
            260                 265                 270

Ser Thr Ser Ser Ser Gly Ser Lys Arg His Lys Ser Gly Ser Met Glu
            275                 280                 285

Glu Asp Val Asp Thr Ser Pro Gly Gly Asp Tyr Tyr Thr Ser Pro Ser
290                 295                 300

Ser Pro Thr Ser Ser Ser Arg Asn Trp Thr Glu Asp Met Glu Gly Gly
305                 310                 315                 320

Ile Ser Ser Pro Val Lys Lys Thr Glu Met Asp Lys Ser Pro Phe Asn
                325                 330                 335

Ser Pro Ser Pro Gln Asp Ser Pro Arg Leu Ser Ser Phe Thr Gln His
            340                 345                 350

His Arg Pro Val Ile Ala Val His Ser Gly Ile Ala Arg Ser Pro His
            355                 360                 365

Pro Ser Ser Ala Leu His Phe Pro Thr Thr Ser Ile Leu Pro Gln Thr
370                 375                 380

Ala Ser Thr Tyr Phe Pro His Thr Ala Ile Arg Tyr Pro Pro His Leu
385                 390                 395                 400

Asn Pro Gln Asp Pro Leu Lys Asp Leu Val Ser Leu Ala Cys Asp Pro
                405                 410                 415

Ala Ser Gln Gln Pro Gly Pro Leu Asn Gly Ser Gly Leu Lys Met
            420                 425                 430

Pro Ser His Cys Leu Ser Ala Gln Met Leu Ala Pro Pro Pro Gly
            435                 440                 445

Leu Pro Arg Leu Ala Leu Pro Pro Ala Thr Lys Pro Ala Thr Thr Ser
450                 455                 460

```
Glu Gly Gly Ala Thr Ser Pro Thr Ser Pro Ser Tyr Ser Pro Pro Asp
465                 470                 475                 480

Thr Ser Pro Ala Asn Arg Ser Phe Val Gly Leu Gly Pro Arg Asp Pro
                485                 490                 495

Ala Gly Ile Tyr Gln Ala Gln Ser Trp Tyr Leu Gly
            500                 505

<210> SEQ ID NO 8
<211> LENGTH: 462
<212> TYPE: PRT
<213> ORGANISM: Homo sapiens

<400> SEQUENCE: 8

Met Gln Leu Arg Lys Met Gln Thr Val Lys Lys Glu Gln Ala Ser Leu
1               5                   10                  15

Asp Ala Ser Ser Asn Val Asp Lys Met Met Val Leu Asn Ser Ala Leu
            20                  25                  30

Thr Glu Val Ser Glu Asp Ser Thr Thr Gly Glu Glu Leu Leu Leu Ser
        35                  40                  45

Glu Gly Ser Val Gly Lys Asn Lys Ser Ser Ala Cys Arg Arg Lys Arg
50                  55                  60

Glu Phe Ile Pro Asp Glu Lys Lys Asp Ala Met Tyr Trp Glu Lys Arg
65                  70                  75                  80

Arg Lys Asn Asn Glu Ala Ala Lys Arg Ser Arg Glu Lys Arg Arg Leu
                85                  90                  95

Asn Asp Leu Val Leu Glu Asn Lys Leu Ile Ala Leu Gly Glu Glu Asn
            100                 105                 110

Ala Thr Leu Lys Ala Glu Leu Leu Ser Leu Lys Leu Lys Phe Gly Leu
        115                 120                 125

Ile Ser Ser Thr Ala Tyr Ala Gln Glu Ile Gln Lys Leu Ser Asn Ser
130                 135                 140

Thr Ala Val Tyr Phe Gln Asp Tyr Gln Thr Ser Lys Ser Asn Val Ser
145                 150                 155                 160

Ser Phe Val Asp Glu His Glu Pro Ser Met Val Ser Ser Ser Cys Ile
                165                 170                 175

Ser Val Ile Lys His Ser Pro Gln Ser Ser Leu Ser Asp Val Ser Glu
            180                 185                 190

Val Ser Ser Val Glu His Thr Gln Glu Ser Ser Val Gln Gly Ser Cys
        195                 200                 205

Arg Ser Pro Glu Asn Lys Phe Gln Ile Ile Lys Gln Glu Pro Met Glu
210                 215                 220

Leu Glu Ser Tyr Thr Arg Glu Pro Arg Asp Asp Arg Gly Ser Tyr Thr
225                 230                 235                 240

Ala Ser Ile Tyr Gln Asn Tyr Met Gly Asn Ser Phe Ser Gly Tyr Ser
                245                 250                 255

His Ser Pro Pro Leu Leu Gln Val Asn Arg Ser Ser Asn Ser Pro
            260                 265                 270

Arg Thr Ser Glu Thr Asp Asp Gly Val Val Gly Lys Ser Ser Asp Gly
        275                 280                 285

Glu Asp Glu Gln Gln Val Pro Lys Gly Pro Ile His Ser Pro Val Glu
290                 295                 300

Leu Lys His Val His Ala Thr Val Val Lys Val Pro Glu Val Asn Ser
305                 310                 315                 320

Ser Ala Leu Pro His Lys Leu Arg Ile Lys Ala Lys Ala Met Gln Ile
                325                 330                 335
```

```
Lys Val Glu Ala Phe Asp Asn Glu Phe Ala Thr Gln Lys Leu Ser
            340                 345                 350

Ser Pro Ile Asp Met Thr Ser Lys Arg His Phe Glu Leu Glu Lys His
        355                 360                 365

Ser Ala Pro Ser Met Val His Ser Ser Leu Thr Pro Phe Ser Val Gln
        370                 375                 380

Val Thr Asn Ile Gln Asp Trp Ser Leu Lys Ser Glu His Trp His Gln
385                 390                 395                 400

Lys Glu Leu Ser Gly Lys Thr Gln Asn Ser Phe Lys Thr Gly Val Val
            405                 410                 415

Glu Met Lys Asp Ser Gly Tyr Lys Val Ser Asp Pro Glu Asn Leu Tyr
        420                 425                 430

Leu Lys Gln Gly Ile Ala Asn Leu Ser Ala Glu Val Val Ser Leu Lys
        435                 440                 445

Arg Leu Ile Ala Thr Gln Pro Ile Ser Ala Ser Asp Ser Gly
450                 455                 460

<210> SEQ ID NO 9
<211> LENGTH: 427
<212> TYPE: PRT
<213> ORGANISM: Homo sapiens

<400> SEQUENCE: 9

Met Glu Ala Met Ala Ala Ser Thr Ser Leu Pro Asp Pro Gly Asp Phe
1               5                   10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
            85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
            165                 170                 175

Ser Phe Ser Gly Asp Ser Ser Ser Ser Cys Ser Asp His Cys Ile Thr
        180                 185                 190

Ser Ser Asp Met Met Asp Ser Ser Ser Phe Ser Asn Leu Asp Leu Ser
    195                 200                 205

Glu Glu Asp Ser Asp Asp Pro Ser Val Thr Leu Glu Leu Ser Gln Leu
210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
            245                 250                 255
```

```
Glu Asp Gln Ile Val Leu Leu Lys Ser Ser Ala Ile Glu Val Ile Met
                260                 265                 270

Leu Arg Ser Asn Glu Ser Phe Thr Met Asp Asp Met Ser Trp Thr Cys
            275                 280                 285

Gly Asn Gln Asp Tyr Lys Tyr Arg Val Ser Asp Val Thr Lys Ala Gly
        290                 295                 300

His Ser Leu Glu Leu Ile Glu Pro Leu Ile Lys Phe Gln Val Gly Leu
305                 310                 315                 320

Lys Lys Leu Asn Leu His Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Gly Ser His Leu Leu Tyr Ala Lys Met Ile
370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
            405                 410                 415

Leu Val Leu Glu Val Phe Gly Asn Glu Ile Ser
                420                 425

<210> SEQ ID NO 10
<211> LENGTH: 268
<212> TYPE: PRT
<213> ORGANISM: Homo sapiens

<400> SEQUENCE: 10

Met Ala Gln Pro Leu Cys Pro Pro Leu Ser Glu Ser Trp Met Leu Ser
1               5                   10                  15

Ala Ala Trp Gly Pro Thr Arg Arg Pro Pro Ser Asp Lys Asp Cys
            20                  25                  30

Gly Arg Ser Leu Val Ser Ser Pro Asp Ser Trp Gly Ser Thr Pro Ala
        35                  40                  45

Asp Ser Pro Val Ala Ser Pro Ala Arg Pro Gly Thr Leu Arg Asp Pro
50                  55                  60

Arg Ala Pro Ser Val Gly Arg Gly Ala Arg Ser Ser Arg Leu Gly
65                  70                  75                  80

Ser Gly Gln Arg Gln Ser Ala Ser Glu Arg Glu Lys Leu Arg Met Arg
                85                  90                  95

Thr Leu Ala Arg Ala Leu His Glu Leu Arg Arg Phe Leu Pro Pro Ser
            100                 105                 110

Val Ala Pro Ala Gly Gln Ser Leu Thr Lys Ile Glu Thr Leu Arg Leu
        115                 120                 125

Ala Ile Arg Tyr Ile Gly His Leu Ser Ala Val Leu Gly Leu Ser Glu
130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
            165                 170                 175

Arg Thr Gln Ala Glu Gly Gln Gly Gln Gly Arg Gly Leu Gly Leu Val
        180                 185                 190

Ser Ala Val Arg Ala Gly Ala Ser Trp Gly Ser Pro Pro Ala Cys Pro
            195                 200                 205
```

```
Gly Ala Arg Ala Ala Pro Glu Pro Arg Asp Pro Pro Ala Leu Phe Ala
210                 215                 220

Glu Ala Ala Cys Pro Glu Gly Gln Ala Met Glu Pro Ser Pro Pro Ser
225                 230                 235                 240

Pro Leu Leu Pro Gly Asp Val Leu Ala Leu Leu Glu Thr Trp Met Pro
                245                 250                 255

Leu Ser Pro Leu Glu Trp Leu Pro Glu Glu Pro Lys
            260                 265

<210> SEQ ID NO 11
<211> LENGTH: 1104
<212> TYPE: PRT
<213> ORGANISM: Homo sapiens

<400> SEQUENCE: 11

Met Ala Arg Arg Gly Lys Lys Pro Val Val Arg Thr Leu Glu Asp Leu
1               5                   10                  15

Thr Leu Asp Ser Gly Tyr Gly Gly Ala Ala Asp Ser Val Arg Ser Ser
                20                  25                  30

Asn Leu Ser Leu Cys Cys Ser Asp Ser His Pro Ala Ser Pro Tyr Gly
            35                  40                  45

Gly Ser Cys Trp Pro Pro Leu Ala Asp Ser Met His Ser Arg His Asn
        50                  55                  60

Ser Phe Asp Thr Val Asn Thr Ala Leu Val Glu Asp Ser Glu Gly Leu
65                  70                  75                  80

Asp Cys Ala Gly Gln His Cys Ser Arg Leu Leu Pro Asp Leu Asp Glu
                85                  90                  95

Val Pro Trp Thr Leu Gln Glu Leu Glu Ala Leu Leu Leu Arg Ser Arg
            100                 105                 110

Asp Pro Arg Ala Gly Pro Ala Val Pro Gly Gly Leu Pro Lys Asp Ala
        115                 120                 125

Leu Ala Lys Leu Ser Thr Leu Val Ser Arg Ala Leu Val Arg Ile Ala
130                 135                 140

Lys Glu Ala Gln Arg Leu Ser Leu Arg Phe Ala Lys Cys Thr Lys Tyr
145                 150                 155                 160

Glu Ile Gln Ser Ala Met Glu Ile Val Leu Ser Trp Gly Leu Ala Ala
                165                 170                 175

His Cys Thr Ala Ala Ala Leu Ala Ala Leu Ser Leu Tyr Asn Met Ser
            180                 185                 190

Ser Ala Gly Gly Asp Arg Leu Gly Arg Gly Lys Ser Ala Arg Cys Gly
        195                 200                 205

Leu Thr Phe Ser Val Gly Arg Val Tyr Arg Trp Met Val Asp Ser Arg
210                 215                 220

Val Ala Leu Arg Ile His Glu His Ala Ala Ile Tyr Leu Thr Ala Cys
225                 230                 235                 240

Met Glu Ser Leu Phe Arg Asp Ile Tyr Ser Arg Val Val Ala Ser Gly
                245                 250                 255

Val Pro Arg Ser Cys Ser Gly Pro Gly Ser Gly Ser Gly Ser Gly Pro
            260                 265                 270

Gly Pro Ser Ser Gly Pro Gly Ala Ala Pro Ala Ala Asp Lys Glu Arg
        275                 280                 285

Glu Ala Pro Gly Gly Gly Ala Ala Ser Gly Gly Ala Cys Ser Ala Ala
    290                 295                 300

Ser Ser Ala Ser Gly Gly Ser Ser Cys Cys Ala Pro Pro Ala Ala Ala
305                 310                 315                 320
```

-continued

```
Ala Ala Ala Val Pro Pro Ala Ala Ala Asn His His His His
            325             330                 335
His His Ala Leu His Glu Ala Pro Lys Phe Thr Val Glu Thr Leu Glu
        340             345                 350
His Thr Val Asn Asn Asp Ser Glu Ile Trp Gly Leu Leu Gln Pro Tyr
        355                 360                 365
Gln His Leu Ile Cys Gly Lys Asn Ala Ser Gly Val Leu Cys Leu Pro
    370                 375                 380
Asp Ser Leu Asn Leu His Arg Asp Pro Gln Arg Ser Asn Lys Pro Gly
385                 390                 395                 400
Glu Leu Pro Met Phe Ser Gln Ser Glu Leu Arg Thr Ile Glu Gln Ser
                405                 410                 415
Leu Leu Ala Thr Arg Val Gly Ser Ile Ala Glu Leu Ser Asp Leu Val
            420                 425                 430
Ser Arg Ala Met His His Leu Gln Pro Leu Asn Ala Lys His His Gly
        435                 440                 445
Asn Gly Thr Pro Leu His His Lys Gln Gly Ala Leu Tyr Trp Glu Pro
        450                 455                 460
Glu Ala Leu Tyr Thr Leu Cys Tyr Phe Met His Cys Pro Gln Met Glu
465                 470                 475                 480
Trp Glu Asn Pro Asn Val Glu Pro Ser Lys Val Asn Leu Gln Val Glu
                485                 490                 495
Arg Pro Phe Leu Val Leu Pro Pro Leu Met Glu Trp Ile Arg Val Ala
            500                 505                 510
Val Ala His Ala Gly His Arg Arg Ser Phe Ser Met Asp Ser Asp Asp
        515                 520                 525
Val Arg Gln Ala Ala Arg Leu Leu Leu Pro Gly Val Asp Cys Glu Pro
        530                 535                 540
Arg Gln Leu Arg Ala Asp Asp Cys Phe Cys Ala Ser Arg Lys Leu Asp
545                 550                 555                 560
Ala Val Ala Ile Glu Ala Lys Phe Lys Gln Asp Leu Gly Phe Arg Met
                565                 570                 575
Leu Asn Cys Gly Arg Thr Asp Leu Val Lys Gln Ala Val Ser Leu Leu
            580                 585                 590
Gly Pro Asp Gly Ile Asn Thr Met Ser Glu Gln Gly Met Thr Pro Leu
        595                 600                 605
Met Tyr Ala Cys Val Arg Gly Asp Glu Ala Met Val Gln Met Leu Leu
        610                 615                 620
Asp Ala Gly Ala Asp Leu Asn Val Glu Val Ser Thr Pro His Lys
625                 630                 635                 640
Tyr Pro Ser Val His Pro Glu Thr Arg His Trp Thr Ala Leu Thr Phe
                645                 650                 655
Ala Val Leu His Gly His Ile Pro Val Val Gln Leu Leu Leu Asp Ala
            660                 665                 670
Gly Ala Lys Val Glu Gly Ser Val Glu His Gly Glu Glu Asn Tyr Ser
        675                 680                 685
Glu Thr Pro Leu Gln Leu Ala Ala Ala Val Gly Asn Phe Glu Leu Val
        690                 695                 700
Ser Leu Leu Leu Glu Arg Gly Ala Asp Pro Leu Ile Gly Thr Met Tyr
705                 710                 715                 720
Arg Asn Gly Ile Ser Thr Thr Pro Gln Gly Asp Met Asn Ser Phe Ser
                725                 730                 735
```

```
Gln Ala Ala Ala His Gly His Arg Asn Val Phe Arg Lys Leu Leu Ala
                740                 745                 750
Gln Pro Glu Lys Glu Lys Ser Asp Ile Leu Ser Leu Glu Glu Ile Leu
            755                 760                 765
Ala Glu Gly Thr Asp Leu Ala Glu Thr Ala Pro Pro Leu Cys Ala
        770                 775                 780
Ser Arg Asn Ser Lys Ala Lys Leu Arg Ala Leu Arg Glu Ala Met Tyr
785                 790                 795                 800
His Ser Ala Glu His Gly Tyr Val Asp Val Thr Ile Asp Ile Arg Ser
                805                 810                 815
Ile Gly Val Pro Trp Thr Leu His Thr Trp Leu Glu Ser Leu Arg Ile
                820                 825                 830
Ala Phe Gln Gln His Arg Arg Pro Leu Ile Gln Cys Leu Leu Lys Glu
                835                 840                 845
Phe Lys Thr Ile Gln Glu Glu Tyr Thr Glu Glu Leu Val Thr Gln
        850                 855                 860
Gly Leu Pro Leu Met Phe Glu Ile Leu Lys Ala Ser Lys Asn Glu Val
865                 870                 875                 880
Ile Ser Gln Gln Leu Cys Val Ile Phe Thr His Cys Tyr Gly Pro Tyr
                885                 890                 895
Pro Ile Pro Lys Leu Thr Glu Ile Lys Arg Lys Gln Thr Ser Arg Leu
                900                 905                 910
Asp Pro His Phe Leu Asn Asn Lys Glu Met Ser Asp Val Thr Phe Leu
                915                 920                 925
Val Glu Gly Arg Pro Phe Tyr Ala His Lys Val Leu Leu Phe Thr Ala
        930                 935                 940
Ser Pro Arg Phe Lys Ala Leu Leu Ser Ser Lys Pro Thr Asn Asp Gly
945                 950                 955                 960
Thr Cys Ile Glu Ile Gly Tyr Val Lys Tyr Ser Ile Phe Gln Leu Val
                965                 970                 975
Met Gln Tyr Leu Tyr Tyr Gly Gly Pro Glu Ser Leu Leu Ile Lys Asn
                980                 985                 990
Asn Glu Ile Met Glu Leu Leu Ser Ala Ala Lys Phe Phe Gln Leu Glu
                995                 1000                1005
Ala Leu Gln Arg His Cys Glu Ile Ile Cys Ala Lys Ser Ile Asn
        1010                1015                1020
Thr Asp Asn Cys Val Asp Ile Tyr Asn His Ala Lys Phe Leu Gly
        1025                1030                1035
Val Thr Glu Leu Ser Ala Tyr Cys Glu Gly Tyr Phe Leu Lys Asn
        1040                1045                1050
Met Met Val Leu Ile Glu Asn Glu Ala Phe Lys Gln Leu Leu Tyr
        1055                1060                1065
Asp Lys Asn Gly Glu Gly Thr Gly Gln Asp Val Leu Gln Asp Leu
        1070                1075                1080
Gln Arg Thr Leu Ala Ile Arg Ile Gln Ser Ile His Leu Ser Ser
        1085                1090                1095
Ser Lys Gly Ser Val Val
        1100

<210> SEQ ID NO 12
<211> LENGTH: 664
<212> TYPE: PRT
<213> ORGANISM: Homo sapiens
```

<400> SEQUENCE: 12

```
Met Pro Ala Val Asp Lys Leu Leu Glu Glu Ala Leu Gln Asp Ser
1               5                   10                  15

Pro Gln Thr Arg Ser Leu Leu Ser Val Phe Glu Glu Asp Ala Gly Thr
                20                  25                  30

Leu Thr Asp Tyr Thr Asn Gln Leu Leu Gln Ala Met Gln Arg Val Tyr
            35                  40                  45

Gly Ala Gln Asn Glu Met Cys Leu Ala Thr Gln Leu Ser Lys Gln
50                  55                  60

Leu Leu Ala Tyr Glu Lys Gln Asn Phe Ala Leu Gly Lys Gly Asp Glu
65                  70                  75                  80

Glu Val Ile Ser Thr Leu His Tyr Phe Ser Lys Val Val Asp Glu Leu
                85                  90                  95

Asn Leu Leu His Thr Glu Leu Ala Lys Gln Leu Ala Asp Thr Met Val
            100                 105                 110

Leu Pro Ile Ile Gln Phe Arg Glu Lys Asp Leu Thr Glu Val Ser Thr
            115                 120                 125

Leu Lys Asp Leu Phe Gly Leu Ala Ser Asn Glu His Asp Leu Ser Met
130                 135                 140

Ala Lys Tyr Ser Arg Leu Pro Lys Lys Lys Glu Asn Glu Lys Val Lys
145                 150                 155                 160

Thr Glu Val Gly Lys Glu Val Ala Ala Ala Arg Arg Lys Gln His Leu
                165                 170                 175

Ser Ser Leu Gln Tyr Tyr Cys Ala Leu Asn Ala Leu Gln Tyr Arg Lys
            180                 185                 190

Gln Met Ala Met Met Glu Pro Met Ile Gly Phe Ala His Gly Gln Ile
            195                 200                 205

Asn Phe Phe Lys Lys Gly Ala Glu Met Phe Ser Lys Arg Met Asp Ser
210                 215                 220

Phe Leu Ser Ser Val Ala Asp Met Val Gln Ser Ile Gln Val Glu Leu
225                 230                 235                 240

Glu Ala Glu Ala Glu Lys Met Arg Val Ser Gln Gln Glu Leu Leu Ser
                245                 250                 255

Val Asp Glu Ser Val Tyr Thr Pro Asp Ser Asp Val Ala Ala Pro Gln
            260                 265                 270

Ile Asn Arg Asn Leu Ile Gln Lys Ala Gly Tyr Leu Asn Leu Arg Asn
            275                 280                 285

Lys Thr Gly Leu Val Thr Thr Thr Trp Glu Arg Leu Tyr Phe Phe Thr
290                 295                 300

Gln Gly Gly Asn Leu Met Cys Gln Pro Arg Gly Ala Val Ala Gly Gly
305                 310                 315                 320

Leu Ile Gln Asp Leu Asp Asn Cys Ser Val Met Ala Val Asp Cys Glu
                325                 330                 335

Asp Arg Arg Tyr Cys Phe Gln Ile Thr Thr Pro Asn Gly Lys Ser Gly
            340                 345                 350

Ile Ile Leu Gln Ala Glu Ser Arg Lys Glu Asn Glu Glu Trp Ile Cys
            355                 360                 365

Ala Ile Asn Asn Ile Ser Arg Gln Ile Tyr Leu Thr Asp Asn Pro Glu
370                 375                 380

Ala Val Ala Ile Lys Leu Asn Gln Thr Ala Leu Gln Ala Val Thr Pro
385                 390                 395                 400

Ile Thr Ser Phe Gly Lys Lys Gln Glu Ser Ser Cys Pro Ser Gln Asn
                405                 410                 415
```

```
Leu Lys Asn Ser Glu Met Glu Asn Glu Asn Asp Lys Ile Val Pro Lys
                420                 425                 430

Ala Thr Ala Ser Leu Pro Glu Ala Glu Leu Ile Ala Pro Gly Thr
            435                 440                 445

Pro Ile Gln Phe Asp Ile Val Leu Pro Ala Thr Glu Phe Leu Asp Gln
450                 455                 460

Asn Arg Gly Ser Arg Arg Thr Asn Pro Phe Gly Glu Thr Glu Asp Glu
465                 470                 475                 480

Ser Phe Pro Glu Ala Glu Asp Ser Leu Leu Gln Gln Met Phe Ile Val
                485                 490                 495

Arg Phe Leu Gly Ser Met Ala Val Lys Thr Asp Ser Thr Thr Glu Val
            500                 505                 510

Ile Tyr Glu Ala Met Arg Gln Val Leu Ala Ala Arg Ala Ile His Asn
        515                 520                 525

Ile Phe Arg Met Thr Glu Ser His Leu Met Val Thr Ser Gln Ser Leu
    530                 535                 540

Arg Leu Ile Asp Pro Gln Thr Gln Val Ser Arg Ala Asn Phe Glu Leu
545                 550                 555                 560

Thr Ser Val Thr Gln Phe Ala Ala His Gln Glu Asn Lys Arg Leu Val
                565                 570                 575

Gly Phe Val Ile Arg Val Pro Glu Ser Thr Gly Glu Glu Ser Leu Ser
            580                 585                 590

Thr Tyr Ile Phe Glu Ser Asn Ser Glu Gly Glu Lys Ile Cys Tyr Ala
        595                 600                 605

Ile Asn Leu Gly Lys Glu Ile Ile Glu Val Gln Lys Asp Pro Glu Ala
    610                 615                 620

Leu Ala Gln Leu Met Leu Ser Ile Pro Leu Thr Asn Asp Gly Lys Tyr
625                 630                 635                 640

Val Leu Leu Asn Asp Gln Pro Asp Asp Asp Gly Asn Pro Asn Glu
                645                 650                 655

His Arg Gly Ala Glu Ser Glu Ala
            660

<210> SEQ ID NO 13
<211> LENGTH: 1067
<212> TYPE: PRT
<213> ORGANISM: Homo sapiens

<400> SEQUENCE: 13

Met Ala Ser Pro Thr Ser Thr Asn Pro Ala His Ala His Phe Glu Ser
1               5                   10                  15

Phe Leu Gln Ala Gln Leu Cys Gln Asp Val Leu Ser Ser Phe Gln Glu
                20                  25                  30

Leu Cys Gly Ala Leu Gly Leu Glu Pro Gly Gly Gly Leu Pro Gln Tyr
            35                  40                  45

His Lys Ile Lys Asp Gln Leu Asn Tyr Trp Ser Ala Lys Ser Leu Trp
        50                  55                  60

Thr Lys Leu Asp Lys Arg Ala Gly Gln Pro Val Tyr Gln Gln Gly Arg
65                  70                  75                  80

Ala Cys Thr Ser Thr Lys Cys Leu Val Val Gly Ala Gly Pro Cys Gly
                85                  90                  95

Leu Arg Val Ala Val Glu Leu Ala Leu Leu Gly Ala Arg Val Val Leu
            100                 105                 110

Val Glu Lys Arg Thr Lys Phe Ser Arg His Asn Val Leu His Leu Trp
        115                 120                 125
```

```
Pro Phe Thr Ile His Asp Leu Arg Ala Leu Gly Ala Lys Lys Phe Tyr
130                 135                 140

Gly Arg Phe Cys Thr Gly Thr Leu Asp His Ile Ser Ile Arg Gln Leu
145                 150                 155                 160

Gln Leu Leu Leu Lys Val Ala Leu Leu Leu Gly Val Glu Ile His
                165                 170                 175

Trp Gly Val Thr Phe Thr Gly Leu Gln Pro Pro Arg Lys Gly Ser
            180                 185                 190

Gly Trp Arg Ala Gln Leu Gln Pro Asn Pro Ala Gln Leu Ala Asn
        195                 200                 205

Tyr Glu Phe Asp Val Leu Ile Ser Ala Ala Gly Gly Lys Phe Val Pro
210                 215                 220

Glu Gly Phe Lys Val Arg Glu Met Arg Gly Lys Leu Ala Ile Gly Ile
225                 230                 235                 240

Thr Ala Asn Phe Val Asn Gly Arg Thr Val Glu Thr Gln Val Pro
                245                 250                 255

Glu Ile Ser Gly Val Ala Arg Ile Tyr Asn Gln Ser Phe Phe Gln Ser
                260                 265                 270

Leu Leu Lys Ala Thr Gly Ile Asp Leu Glu Asn Ile Val Tyr Tyr Lys
        275                 280                 285

Asp Asp Thr His Tyr Phe Val Met Thr Ala Lys Lys Gln Cys Leu Leu
290                 295                 300

Arg Leu Gly Val Leu Arg Gln Asp Trp Pro Asp Thr Asn Arg Leu Leu
305                 310                 315                 320

Gly Ser Ala Asn Val Val Pro Glu Ala Leu Gln Arg Phe Thr Arg Ala
                325                 330                 335

Ala Ala Asp Phe Ala Thr His Gly Lys Leu Gly Lys Leu Glu Phe Ala
                340                 345                 350

Gln Asp Ala His Gly Gln Pro Asp Val Ser Ala Phe Asp Phe Thr Ser
            355                 360                 365

Met Met Arg Ala Glu Ser Ser Ala Arg Val Gln Glu Lys His Gly Ala
370                 375                 380

Arg Leu Leu Leu Gly Leu Val Gly Asp Cys Leu Val Glu Pro Phe Trp
385                 390                 395                 400

Pro Leu Gly Thr Gly Val Ala Arg Gly Phe Leu Ala Ala Phe Asp Ala
                405                 410                 415

Ala Trp Met Val Lys Arg Trp Ala Glu Gly Ala Glu Ser Leu Glu Val
                420                 425                 430

Leu Ala Glu Arg Glu Ser Leu Tyr Gln Leu Leu Ser Gln Thr Ser Pro
            435                 440                 445

Glu Asn Met His Arg Asn Val Ala Gln Tyr Gly Leu Asp Pro Ala Thr
            450                 455                 460

Arg Tyr Pro Asn Leu Asn Leu Arg Ala Val Thr Pro Asn Gln Val Arg
465                 470                 475                 480

Asp Leu Tyr Asp Val Leu Ala Lys Glu Pro Val Gln Arg Asn Asn Asp
                485                 490                 495

Lys Thr Asp Thr Gly Met Pro Ala Thr Gly Ser Ala Gly Thr Gln Glu
            500                 505                 510

Glu Leu Leu Arg Trp Cys Gln Glu Gln Thr Ala Gly Tyr Pro Gly Val
            515                 520                 525

His Val Ser Asp Leu Ser Ser Ser Trp Ala Asp Gly Leu Ala Leu Cys
530                 535                 540
```

```
Ala Leu Val Tyr Arg Leu Gln Pro Gly Leu Leu Glu Pro Ser Glu Leu
545                 550                 555                 560

Gln Gly Leu Gly Ala Leu Glu Ala Thr Ala Trp Ala Leu Lys Val Ala
            565                 570                 575

Glu Asn Glu Leu Gly Ile Thr Pro Val Val Ser Ala Gln Ala Val Val
            580                 585                 590

Ala Gly Ser Asp Pro Leu Gly Leu Ile Ala Tyr Leu Ser His Phe His
        595                 600                 605

Ser Ala Phe Lys Ser Met Ala His Ser Pro Gly Pro Val Ser Gln Ala
        610                 615                 620

Ser Pro Gly Thr Ser Ser Ala Val Leu Phe Leu Ser Lys Leu Gln Arg
625                 630                 635                 640

Thr Leu Gln Arg Ser Arg Ala Lys Glu Asn Ala Glu Asp Ala Gly Gly
                645                 650                 655

Lys Lys Leu Arg Leu Glu Met Glu Ala Glu Thr Pro Ser Thr Glu Val
                660                 665                 670

Pro Pro Asp Pro Glu Pro Gly Val Pro Leu Thr Pro Ser Gln His
                675                 680                 685

Gln Glu Ala Gly Ala Gly Asp Leu Cys Ala Leu Cys Gly Glu His Leu
        690                 695                 700

Tyr Val Leu Glu Arg Leu Cys Val Asn Gly His Phe Phe His Arg Ser
705                 710                 715                 720

Cys Phe Arg Cys His Thr Cys Glu Ala Thr Leu Trp Pro Gly Gly Tyr
                725                 730                 735

Glu Gln His Pro Gly Asp Gly His Phe Tyr Cys Leu Gln His Leu Pro
                740                 745                 750

Gln Thr Asp His Lys Ala Glu Gly Ser Asp Arg Gly Pro Glu Ser Pro
        755                 760                 765

Glu Leu Pro Thr Pro Ser Glu Asn Ser Met Pro Pro Gly Leu Ser Thr
770                 775                 780

Pro Thr Ala Ser Gln Glu Gly Ala Gly Pro Val Pro Asp Pro Ser Gln
785                 790                 795                 800

Pro Thr Arg Arg Gln Ile Arg Leu Ser Ser Pro Glu Arg Gln Arg Leu
                805                 810                 815

Ser Ser Leu Asn Leu Thr Pro Asp Pro Glu Met Glu Pro Pro Pro Lys
                820                 825                 830

Pro Pro Arg Ser Cys Ser Ala Leu Ala Arg His Ala Leu Glu Ser Ser
        835                 840                 845

Phe Val Gly Trp Gly Leu Pro Val Gln Ser Pro Gln Ala Leu Val Ala
850                 855                 860

Met Glu Lys Glu Glu Lys Glu Ser Pro Phe Ser Ser Glu Glu Glu Glu
865                 870                 875                 880

Glu Asp Val Pro Leu Asp Ser Asp Val Glu Gln Ala Leu Gln Thr Phe
                885                 890                 895

Ala Lys Thr Ser Gly Thr Met Asn Asn Tyr Pro Thr Trp Arg Arg Thr
        900                 905                 910

Leu Leu Arg Arg Ala Lys Glu Glu Met Lys Arg Phe Cys Lys Ala
                915                 920                 925

Gln Thr Ile Gln Arg Arg Leu Asn Glu Ile Glu Ala Ala Leu Arg Glu
        930                 935                 940

Leu Glu Ala Glu Gly Val Lys Leu Glu Leu Ala Leu Arg Arg Gln Ser
945                 950                 955                 960
```

```
Ser Ser Pro Glu Gln Gln Lys Lys Leu Trp Val Gly Gln Leu Leu Gln
            965                 970                 975

Leu Val Asp Lys Lys Asn Ser Leu Val Ala Glu Glu Ala Glu Leu Met
        980                 985                 990

Ile Thr Val Gln Glu Leu Asn Leu  Glu Glu Lys Gln Trp  Gln Leu Asp
        995                 1000                1005

Gln Glu  Leu Arg Gly Tyr Met  Asn Arg Glu Glu Asn  Leu Lys Thr
         1010                1015                1020

Ala Ala  Asp Arg Gln Ala Glu  Asp Gln Val Leu Arg  Lys Leu Val
         1025                1030                1035

Asp Leu  Val Asn Gln Arg Asp  Ala Leu Ile Arg Phe  Gln Glu Glu
         1040                1045                1050

Arg Arg  Leu Ser Glu Leu Ala  Leu Gly Thr Gly Ala  Gln Gly
         1055                1060                1065

<210> SEQ ID NO 14
<211> LENGTH: 125
<212> TYPE: PRT
<213> ORGANISM: Homo sapiens

<400> SEQUENCE: 14

Met Pro His Ser Ser Asp Ser Ser Asp Ser Phe Ser Arg Ser Pro
1               5                   10                  15

Pro Pro Gly Lys Gln Asp Ser Ser Asp Val Arg Arg Val Gln Arg
            20                  25                  30

Arg Glu Lys Asn Arg Ile Ala Ala Gln Lys Ser Arg Gln Arg Gln Thr
        35                  40                  45

Gln Lys Ala Asp Thr Leu His Leu Glu Ser Glu Asp Leu Glu Lys Gln
    50                  55                  60

Asn Ala Ala Leu Arg Lys Glu Ile Lys Gln Leu Thr Glu Glu Leu Lys
65                  70                  75                  80

Tyr Phe Thr Ser Val Leu Asn Ser His Glu Pro Leu Cys Ser Val Leu
                85                  90                  95

Ala Ala Ser Thr Pro Ser Pro Pro Glu Val Val Tyr Ser Ala His Ala
            100                 105                 110

Phe His Gln Pro His Val Ser Ser Pro Arg Phe Gln Pro
        115                 120                 125

<210> SEQ ID NO 15
<211> LENGTH: 660
<212> TYPE: PRT
<213> ORGANISM: Homo sapiens

<400> SEQUENCE: 15

Met Leu Val Cys Tyr Ser Val Leu Ala Cys Glu Ile Leu Trp Asp Leu
1               5                   10                  15

Pro Cys Ser Ile Met Gly Ser Pro Leu Gly His Phe Thr Trp Asp Lys
            20                  25                  30

Tyr Leu Lys Glu Thr Cys Ser Val Pro Ala Pro Val His Cys Phe Lys
        35                  40                  45

Gln Ser Tyr Thr Pro Pro Ser Asn Glu Phe Lys Ile Ser Met Lys Leu
    50                  55                  60

Glu Ala Gln Asp Pro Arg Asn Thr Thr Ser Thr Cys Ile Ala Thr Val
65                  70                  75                  80

Val Gly Leu Thr Gly Ala Arg Leu Arg Leu Arg Leu Asp Gly Ser Asp
                85                  90                  95
```

```
Asn Lys Asn Asp Phe Trp Arg Leu Val Asp Ser Ala Glu Ile Gln Pro
            100                 105                 110

Ile Gly Asn Cys Glu Lys Asn Gly Gly Met Leu Gln Pro Pro Leu Gly
        115                 120                 125

Phe Arg Leu Asn Ala Ser Ser Trp Pro Met Phe Leu Leu Lys Thr Leu
    130                 135                 140

Asn Gly Ala Glu Met Ala Pro Ile Arg Ile Phe His Lys Glu Pro Pro
145                 150                 155                 160

Ser Pro Ser His Asn Phe Phe Lys Met Gly Met Lys Leu Glu Ala Val
                165                 170                 175

Asp Arg Lys Asn Pro His Phe Ile Cys Pro Ala Thr Ile Gly Glu Val
            180                 185                 190

Arg Gly Ser Glu Val Leu Val Thr Phe Asp Gly Trp Arg Gly Ala Phe
        195                 200                 205

Asp Tyr Trp Cys Arg Phe Asp Ser Arg Asp Ile Phe Pro Val Gly Trp
    210                 215                 220

Cys Ser Leu Thr Gly Asp Asn Leu Gln Pro Pro Gly Thr Lys Val Val
225                 230                 235                 240

Ile Pro Lys Asn Pro Tyr Pro Ala Ser Asp Val Asn Thr Glu Lys Pro
                245                 250                 255

Ser Ile His Ser Ser Thr Lys Thr Val Leu Glu His Gln Pro Gly Gln
            260                 265                 270

Arg Gly Arg Lys Pro Gly Lys Lys Arg Gly Arg Thr Pro Lys Thr Leu
        275                 280                 285

Ile Ser His Pro Ile Ser Ala Pro Ser Lys Thr Ala Glu Pro Leu Lys
    290                 295                 300

Phe Pro Lys Lys Arg Gly Pro Lys Pro Gly Ser Lys Arg Lys Pro Arg
305                 310                 315                 320

Thr Leu Leu Asn Pro Pro Ala Ser Pro Thr Thr Ser Thr Pro Glu
                325                 330                 335

Pro Asp Thr Ser Thr Val Pro Gln Asp Ala Ala Thr Ile Pro Ser Ser
        340                 345                 350

Ala Met Gln Ala Pro Thr Val Cys Ile Tyr Leu Asn Lys Asn Gly Ser
    355                 360                 365

Thr Gly Pro His Leu Asp Lys Lys Val Gln Gln Leu Pro Asp His
370                 375                 380

Phe Gly Pro Ala Arg Ala Ser Val Val Leu Gln Gln Ala Val Gln Ala
385                 390                 395                 400

Cys Ile Asp Cys Ala Tyr His Gln Lys Thr Val Phe Ser Phe Leu Lys
            405                 410                 415

Gln Gly His Gly Gly Glu Val Ile Ser Ala Val Phe Asp Arg Glu Gln
        420                 425                 430

His Thr Leu Asn Leu Pro Ala Val Asn Ser Ile Thr Tyr Val Leu Arg
    435                 440                 445

Phe Leu Glu Lys Leu Cys His Asn Leu Arg Ser Asp Asn Leu Phe Gly
450                 455                 460

Asn Gln Pro Phe Thr Gln Thr His Leu Ser Leu Thr Ala Ile Glu Tyr
465                 470                 475                 480

Ser His Ser His Asp Arg Tyr Leu Pro Gly Glu Thr Phe Val Leu Gly
            485                 490                 495

Asn Ser Leu Ala Arg Ser Leu Glu Pro His Ser Asp Ser Met Asp Ser
        500                 505                 510
```

```
Ala Ser Asn Pro Thr Asn Leu Val Ser Thr Ser Gln Arg His Arg Pro
            515                 520                 525

Leu Leu Ser Ser Cys Gly Leu Pro Pro Ser Thr Ala Ser Ala Val Arg
530                 535                 540

Arg Leu Cys Ser Arg Gly Val Leu Lys Gly Ser Asn Glu Arg Arg Asp
545                 550                 555                 560

Met Glu Ser Phe Trp Lys Leu Asn Arg Ser Pro Gly Ser Asp Arg Tyr
                565                 570                 575

Leu Glu Ser Arg Asp Ala Ser Arg Leu Ser Gly Arg Asp Pro Ser Ser
            580                 585                 590

Trp Thr Val Glu Asp Val Met Gln Phe Val Arg Glu Ala Asp Pro Gln
        595                 600                 605

Leu Gly Pro His Ala Asp Leu Phe Arg Lys His Glu Ile Asp Gly Lys
    610                 615                 620

Ala Leu Leu Leu Leu Arg Ser Asp Met Met Met Lys Tyr Met Gly Leu
625                 630                 635                 640

Lys Leu Gly Pro Ala Leu Lys Leu Ser Tyr His Ile Asp Arg Leu Lys
                645                 650                 655

Gln Gly Lys Phe
            660

<210> SEQ ID NO 16
<211> LENGTH: 197
<212> TYPE: PRT
<213> ORGANISM: Homo sapiens

<400> SEQUENCE: 16

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195
```

TRANSCRIPTION FACTOR MEDIATED PROGRAMMING TOWARDS MEGAKARYOCYTES

SEQUENCE LISTING

The instant application contains a Sequence Listing which has been submitted electronically in ASCII format and is hereby incorporated by reference in its entirety. Said ASCII copy, created on Sep. 12, 2018, is named 010600_Sequences_ST25.txt and is 70,865 bytes in size.

This invention relates to the generation of megakaryocyte (MK) lineages from pluripotent stem cells (PSCs).

Megakaryocytes (MK) are blood cells which are uniquely responsible for formation of platelets regulating haemostasis and thrombosis (Kaushansky K. Blood. 2008; 111:981-986). Low blood platelet count, or thrombocytopenia, can originate from different conditions (including viral and bacterial infections, hereditary syndromes, cancers, medication induced) and may result in severe haemorrhages in extreme cases. In the UK, the National Health Service is delivering about 240,000 platelet concentrate units per year from voluntary donors for therapeutic and prophylactic purposes. The total platelet cost for NHS is evaluated at £55 m per year (£230 per unit in 2009 October). In addition, platelet transfusion refractoriness due to alloimmune reactions is a serious issue in particular for patients with regular transfusion needs, which imposes additional biological characterization, i.e. HLA genotyping, of both donors and recipients. Eventually, as for other human biological products, donor platelet transfusion goes with a risk of transmission of contagious agents.

Human embryonic stem cells (hESC) can be maintained and expanded in culture indefinitely and are able to generate virtually all the different cell types of the organism (Keller G Genes Dev. 2005; 19:1129.1155). Indeed, they hold great promise for cell based therapies. Interestingly, it has been shown that the banking of a small number of carefully selected hESC lines to include the most common HLA haplotypes in the UK may be sufficient to offer practical benefits, i.e. matched or single mismatched tissues for a majority of the population (Taylor C J et al Lancet. 2005; 366:2019-2025). Moreover, the ability to derive pluripotent stem cells equivalent to hESCs—the so-called induced pluripotent stem cells (iPSCs)—from adult somatic cells like skin fibroblasts or circulating blood cells, opens new avenues for clinical applications with the opportunity of generating fully compatible tissues for virtually every single individual (Yamanaka S. Cell Stem Cell. 2010; 7:1-2; Takahashi K et al Cell. 2007; 131:861-872).

Human ESCs, iPSCs and other human stem cells (collectively human pluripotent stem cells, or hPSCs) may thus offer a valuable option for ex-vivo production of biocompatible platelets. Up to now, generation of clinically relevant cell types from hPSCs has been essentially achieved by mimicking in vivo embryonic development based on scientific knowledge gathered from model vertebrate organisms (Murry C E, Keller G. Cell. 2008; 132:661-680). Existing protocols for generation of platelet precursors, the megakaryocytes, use poorly defined culture medium containing fetal calf serum and bone marrow derived murine stromal cell lines (OP9, C3H10T1/2) to support megakaryocyte differentiation and platelet production (Gaur M, et al J Thromb Haemost. (2006) 4:436-442; Takayama N, et al. Blood (2008) 111:5298-5306; Takayama N, et al. J Exp Med. (2010) 207:2817-2830). More recently, protocols using serum free culture conditions to differentiate megakaryocytes from hPSC were described but platelet production was still dependent on a co-culture step with the OP9 cell line (Lu S J, et al. Cell Res. 2011; Pick et al PLoS One February 2013 10.1371/journal.pone.0055530). These methods involve long-term culture of up to 26 days with complicated cell handling—as single haemangioblast colony picking in semi-solid medium—to produce mature megakaryocytes, yet showing low platelet release capacity. Noteworthy, as previously reported in the context of differentiation of other cell lineages, high variability has been found regarding megakaryocyte generation among different hPSC lines.

This invention relates to the development of a process for the efficient forward programming of human pluripotent cells into megakaryocyte progenitor cells (MK-FoP). This may be useful, for example, in production of mature megakaryocytes and platelets; the modelling of thrombocytopenia and other platelet-associated conditions; and the development of therapeutics to these conditions.

An aspect of the invention provides a method of forward programming pluripotent cells into megakaryocyte progenitor cells; or producing megakaryocyte progenitor cells; the method comprising;
i) providing a population of isolated pluripotent stem cells (PSCs),
ii) introducing a combination of transcription factors (TFs) into the population of PSCs, said combination comprising GATA1, FLI1 and TAL1, and;
iii) culturing said population of cells.

The combination of transcription factors introduced into the cell population imposes a megakaryocyte progenitor phenotype i.e. one or more cells in the population are forward programmed by the transcription factor combination into megakaryocyte progenitor cells.

A method of producing mammalian cells with a megakaryocyte progenitor phenotype as described herein may comprise;
i) providing a population of isolated pluripotent stem cells (PSCs),
ii) introducing a combination of transcription factors into the population of PSCs, said combination comprising GATA1, FLI1 and TAL1, and;
iii) culturing said population of cells, such that one or more cells in the population displays a megakaryocyte progenitor phenotype.

The population may be cultured under suitable conditions and for a sufficient period of time, following introduction of the transcription factors, to allow one or more cells in the population to display a megakaryocyte progenitor phenotype, for example the stable expression of CD61, CD34 and CD41a; and/or the stable expression of CD61, CD235a and CD41a in said cells.

After programming, the megakaryocyte progenitor cells may be maintained in culture, expanded, stored, for example frozen using conventional techniques, or used in therapeutic or other applications as described herein.

Transcription factors are DNA binding proteins which regulate the expression of genes in cells. Preferably, the transcription factors introduced into the PSCs are human transcription factors.

The combination of transcription factors for programming PSCs to become megakaryocyte progenitors as described herein comprises GATA1 (SEQ ID NO: 1), FLI1 (SEQ ID NO: 2)and TAL1 (SEQ ID NO: 3). The amino acid sequences of GATA1, FLI1 and TAL1 are readily available on public databases. For example, the reference amino acid sequence of human GATA1 (GATA binding protein 1; also known as ERYF1: Gene ID 2623) has the NCBI database entry NP_002040.1 GI: 4503925 (SEQ ID NO: 1); the reference amino acid sequence of human FLI1 (Friend leukemia virus integration 1, also known as EWSR1, SIC-1 or ERGB; Gene ID 2313) has the NCBI database entry NP 002008.2 GI: 7110593 (SEQ ID NO: 2)and the reference amino acid sequence of human TAL1 (T cell acute lymphocytic leukemia protein 1; Gene No: 6886) has the NCBI database entry NP_003180.1 GI: 4507363 (SEQ ID NO: 3).

In some embodiments, the combination of transcription factors may lack TAL1. For example, a method of producing mammalian cells with a megakaryocyte progenitor phenotype as described herein may comprise;
 i) providing a population of isolated pluripotent stem cells (PSCs),
 ii) introducing a combination of transcription factors into the population of PSCs, said combination comprising GATA1 and FLI1, and;
 iii) culturing said population of cells, such that one or more cells in the population displays a megakaryocyte progenitor phenotype.

GATA1, FLI1 and TAL1 may be produced using routine recombinant techniques or may be obtained from commercial suppliers (e.g. R&D Systems, Minneapolis, Minn., USA).

In some embodiments, the combination of transcription factors may consist of GATA1, FLI1 and TAL1 i.e. the only transcription factors in introduced into the PSCs are GATA1, FLI1 and TAL1.

In other embodiments, the combination of transcription factors may consist of GATA1, FLI1 and TAL1, with optionally, one, two, three or more, additional transcription factors. For example, additional transcription factors may include one or more of the transcription factors shown in Table 1 or one or more of IKZF1, HOXA5, RUNX1, ZFPM2, ZFPM1 and GATA2.

In some preferred embodiments, additional transcription factors may include one or more of ABLIM1, FHL1, RUNX3, NFIC, NFIL3, VDR, MESP1, BTBD11, APPL2, MICAL1, BATF, SCMH1 and MBP, as shown in table 2.

The amino acid sequences of IKZF1, HOXA5, RUNX1, ZFPM2, ZFPM1 and GATA2 and ABLIM1, FHL1, RUNX3, NFIC, NFIL3, VDR, MESP1, BTBD11, APPL2, MICAL1, BATF, SCMH1 and MBP are readily available on public databases.

Suitable transcription factor nucleic acids and proteins may be produced using routine recombinant techniques or obtained from commercial suppliers (e.g. R&D Systems, Minneapolis, Minn., USA; Cellgenix, DE; Life Technologies, USA).

Suitable transcription factors for use as described herein may comprise the reference database amino sequence or a variant thereof.

A suitable variant may have at least 50%, at least 60%, at least 70%, at least 80%, at least 90%, at least 95%, or at least 98% sequence identity to the reference sequence.

Amino acid sequence identity is generally defined with reference to the algorithm GAP (GCG Wisconsin Package™, Accelrys, San Diego Calif.). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN (which use the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), generally employing default parameters.

Particular sequence variants may differ from a reference sequence by insertion, addition, substitution or deletion of 1 amino acid, 2, 3, 4, 5-10, 10-20 or 20-30 amino acids.

PSCs are unspecialized, undifferentiated cells that are capable of replicating or self-renewing themselves and developing into specialized cells of all three primary germ layers i.e. ectoderm, mesoderm and endoderm but are not able to develop into all embryonic and extra-embryonic tissues, including trophectoderm (i.e. not totipotent). Preferably, the PSCs are not committed to a haematopoietic lineage.

In preferred embodiments, the PSCs are human pluripotent stem cells.

PSCs include embryonic stem (ES) cells and non-embryonic stem cells, including foetal and adult somatic stem cells and stem cells derived from non-pluripotent cells, for example induced pluripotent (iPS) cells which are derived from non-pluripotent cells. iPS cells are described in more detail below.

PSCs may express one or more of the following pluripotency associated markers: Oct4, Sox2, Alkaline Phosphatase, SSEA-3, Nanog, SSEA-4 and Tra-1-60. Preferably, pluripotent stem cells express Oct4.

Human PSCs do not express haematopoietic cell or megakaryocyte markers, such as CD61, CD34, CD41, CD42a, CD42b and GPVI. For example, the pluripotent stem cells may have the phenotype CD61-, CD34-, CD41a, CD42a-, CD42b-, GPVI-.

Markers expressed by a cell, including pluripotency associated markers and haematopoietic cell markers, may be identified using standard techniques, such as flow cytometry, PCR, western blotting, immunocytochemistry and in situ hybridisation.

In some embodiments, the PSCs are ES cells, for example human ES cells and non-human ES cells. Suitable ES cells may be obtained from a cultured hES cell line, such as Edi2, H9 or hSF-6. Further examples of suitable human embryonic stem cells are described in (Thomson J A et al Science 282: 1145-1147 (1998); Reubinoff et al. Nat Biotechnol 18:399-404 (2000); Cowan, C. A. et al. N. Engl. J. Med. 350, 1353-1356(2004), Gage, F. H., et al. Ann. Rev. Neurosci. 18 159-192 (1995); and Gotlieb (2002) Annu. Rev. Neurosci 25 381-407); Carpenter et al. Stem Cells. 5(1): 79-88 (2003); see also: the NIH stem cell registry which is accessible online. Potentially clinical grade hESCs are described in Klimanskaya, I. et al. Lancet 365, 1636-1641 (2005); and Ludwig, T. E. et al. Nat. Biotechnol. 24, 185-187 (2006).

In some embodiments, the PSCs are not hES cells.

In some embodiments, the ES cells may be obtained by methods which do not involve the destruction of a human embryo or the use of a human embryo for an industrial or commercial purpose. For example, hES cells may be obtained by blastomere biopsy techniques (Klimanskaya (2013) Semin Reprod Med. 31(1):49-55; Klimanskaya et al Nature (2006), 444(7118)481-5; Chung et al Cell Stem Cell 2008, 2(2), 113-117; U.S. Pat. No. 7,893,315).

In other embodiments, the pluripotent stem cells are iPS cells, for example human iPS cells.

iPS cells are pluripotent cells which are derived from non-pluripotent ancestor cells, for example somatic cells, such as fibroblasts. Ancestor cells are typically reprogrammed into iPS cells through the introduction of reprogramming factors Oct4, Sox2, Klf4 and c-Myc into the cell.

Other suitable reprogramming factors and combinations of reprogramming factors for inducing pluripotency are known in the art. (see, for example, Yu et al Science 318 2007 1917-1920, Tesar, P. J. et al. Nature 448, 196-199 (2007); Nichols, J. & Smith, A. Cell Stem Cell 4, 487-492 (2009); Ying, Q. L. et al. Nature 453, 519-523 (2008), Hanna J, et al Proc Natl Acad Sci USA. 2010 May 18; 107(20):9222-7; Han D W, et al Nat Cell Biol. 2011 January; 13(1):66-71; Silva J et al Cell. 2009 Aug. 21; 138(4):722-37).

Reprogramming factors and techniques for the production of iPS cells are well-known in the art and include introducing reprogramming factors by plasmid or viral transfection, direct protein delivery or direct delivery of nucleic acid, such as mRNA. (Yamanaka et al Nature (2007); 448:313-7; Yamanaka 6 (2007) Jun. 7; 1(1):39-49. Kim et al. Nature. (2008) Jul. 31; 454(7204):646-50; Takahashi Cell. (2007) Nov. 30; 131(5):861-72. Park et al Nature. (2008) Jan. 10; 451(7175):141-6; Kim et al Cell Stem Cell. (2009) Jun. 5; 4(6):472-6; Vallier, L., et al. (2009) Stem Cells 27, 2655-66.).

The non-pluripotent ancestor cells for use in the production of iPS cells may be obtained from an individual. The individual may be healthy (i.e. without any disease condition) or may have a disease condition. For example, iPS cells may be derived from a sample of cells obtained from an individual with a haematological condition, for example a thrombocytopenic or other platelet-related condition, including essential thrombocytosis and congenital amegakaryocytic thrombocytopenia (CAMT), Thrombocytopenia-absent radius syndrome (TAR), Bernard Soulier syndrome (BSS), Gray platelet syndrome (GPS), and Glanzmann thrombasthenia. IPS cells obtained from an individual with a haematological condition may be used to generate megakaryocyte progenitor cells or mature megakaryocytes using the methods described herein for modelling a haematological condition; for the treatment of an individual with a haematological condition or for the generation of platelets for the treatment of an individual with a haematological condition (Cell Mol Life Sci. 2012 Apr. 24).

A population of pluripotent stem cells for use in the present methods, for example human pluripotent stem cells, may be obtained by culturing cells from a pluripotent cell line, using conventional techniques (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)). For example, human pluripotent cells suitable for use in the present methods may be conventionally cultured in a culture dish on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Human pluripotent cells for use in the present methods may be passaged by enzymatic or mechanical means. Suitable culture media for human pluripotent cells include SC medium (Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human bFGF) and ES medium (DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml Penicillin and 50 mg/ml Streptomycin).

A population of pluripotent stem cells for use in the present methods, for example human pluripotent stem cells, is preferably substantially free from one or more other cell types.

Before introduction of feeder cells, the population of isolated pluripotent stem cells may be expanded. For example, the human pluripotent stem cells may be cultured in a monolayer under conditions that simulate FGF2 signalling. In some embodiments, the cells may be cultured in a culture medium supplemented with FGF2 (e.g. 5 to 20 ng/ml FGF2, preferably 10 ng/ml). Suitable culture media include the SC and ES media described above, which may be MEF-conditioned and supplemented with FGF2.

Any mammalian FGF2 may be employed, preferably human fibroblast growth factor 2(FGF2) (NCBI Gene ID: 2247, nucleic acid sequence NM_002006.3 GI: 41352694, amino acid sequence NP_001997.4 GI: 41352695). FGF2 may be produced using routine recombinant techniques or obtained from commercial suppliers (e.g. R&D, Minneapolis, Minn., USA).

As described above, pluripotent cells are typically cultured and maintained on MEF feeder cells and may be separated from the feeder cells by any suitable technique. For example, the cells may be briefly (e.g. one hour) cultured on gelatin, and then the human pluripotent cells, which do not adhere to the gelatin separated from the MEFs which do adhere to the gelatin. In most experimental settings, human pluripotent stem cells have been cultivated in CDM on gelatin coated dishes (Vallier et al Curr Protoc Stem Cell Biol. 2008 March; Chapter 1:Unit 1D.4.1-1D.4.7) in presence of FGF2 and Activin-A.

In some embodiments, the PSCs may have a defined genotype, such as a defined HLA haplotype. For example, the PSCs may be or have been subjected to biological characterisation, such as HLA genotyping. A method described herein may comprise providing a population of PSCs having a defined genotype, such as a defined HLA haplotype. For example, a population of individuals may be HLA/ABO typed and skin biopsy or peripheral blood from selected individuals in the population with particular HLA/ABO genotypes may be used to generate iPSC lines for forward programming as described herein. Suitable methods of HLA/ABO typing are well-known in the art.

Forward programming is the direct imposition of a more differentiated phenotype on a pluripotent stem cell or other precursor cell which bypasses normal differentiation pathway; i.e. the cell does not pass through intermediate stages of differentiation. For example, a PSC which is forward programmed into a megakaryocyte progenitor does not differentiate through all of the mesoderm progenitor, haemogenic endothelium progenitor and hematopoietic progenitor stages before displaying the megakaryocyte progenitor phenotype. In other words, during step (iii), the cells said population may not progressively display each of the mesoderm progenitor, haemogenic endothelium progenitor and hematopoietic progenitor phenotypes. In some embodiments, a PSC may be differentiated into a mesoderm progenitor cell as described herein and the mesoderm progenitor cell may be forward programmed into a megakaryocyte progenitor.

Mature megakaryocytes are non-proliferative bone marrow cells which are responsible for the production of platelets. Mature megakaryocytes may have the phenotype CD34+/−, CD61+, CD41a+, CD42a+, CD42b+, GPVI+ or CD61+, CD41a+, CD42a+, CD42b+, GPVI+, CD235a+/−. Mature megakaryocytes are large (20-100 um) polyploid cells (4-128N) which eventually produce platelets through pro-platelet formation. They include megakaryoblast, pro-megakaryocyte and megakaryocyte stages as described in Journal of Thrombosis and Haemostasis, 5 (Suppl. 1): 318-327.

Megakaryocyte progenitor cells are proliferative precursors of mature megakaryocytes which undergo a final differentiation step to form mature megakaryocytes. Megakaryocyte progenitors may have the phenotype CD235a+/−, CD34+/−, CD61+, CD41a+, CD42a−, CD42b−, GPVI−. They include BFU-MKs (burst forming units-megakaryocytic), CFU-MKs (colony forming units-megakaryocytic) and PMKBs (promegakaryoblasts) as described in Journal of Thrombosis and Haemostasis, 5 (Suppl. 1): 318-327.

A megakaryocyte progenitor phenotype may include surface expression of CD235a, CD34, CD61 and CD41a or CD34, CD61 and CD41a and may not include expression of CD42a, CD42b and GPVI.

PSCs are forward programmed to become megakaryocyte progenitors in the methods described herein through the introduction of a specific combination of transcription factors, which causes the intracellular levels of the transcription factors in the PSCs to be increased.

The combination of transcription factors may be introduced into the PSCs in the form of nucleic acids (Warren L et al. *Cell Stem Cell.* 2010 Nov. 5; 7(5):618-30) or proteins (Zhou H, et al Cell Stem Cell. 2009 May 8; 4(5):381-4) by any suitable technique, including plasmid or more preferably, viral transfection, direct protein delivery or direct delivery of nucleic acid, such as mRNA. Following introduction of the reprogramming nucleic acids or proteins, the population of treated cells may be cultured.

The combination of transcription factors, for example GATA1, FLI1 and TAL1 and optionally one or more additional transcription factors, may be introduced into the PSCs by expressing nucleic acid encoding the combination of transcription factors in the PSCs. For example, the nucleic acid may be operably linked to inducible or non-inducible regulatory elements within a suitable vector, for example a retroviral or lentiviral vector, for expression within the cells. Vectors containing the nucleic acid are then transfected into the PSCs. Any convenient technique for the transfection may be employed. Following transfection, the combination of transcription factors is expressed in the PSCs and programs the PSCs to become megakaryocyte progenitors.

In some embodiments, transposon-mediated or other random integration transgenesis techniques may be employed. Reprogramming cells through expression of nucleic acid encoding one or more transcription factors is well-known in the art (Takahashi et al 2007; Takahashi et al 2007; Seki et al 2010; Loh et al 2010; Staerk et al 2010).

In some preferred embodiments, the PSCs may be programmed to become megakaryocyte progenitors with minimal or no genetic modification to the cells. Suitable techniques are known in the art and include the use of excisable lentiviral and transposon vectors; repeated application of transient plasmid, episomal and adenovirus or adeno-associated vectors or; the use of small molecules, synthetic mRNA and/or microRNAs (Sidhu K S. Expert Opin Biol Ther. (2011) May; 11(5):569-79; Woltjen K et al (2009) Nature 458 (7239):766-70; Chou B K et al. Cell Res. 2011 21(3):518-29).

In other embodiments, the combination of transcription factors, for example GATA1, FLI1 and TAL1 and optionally one or more additional transcription factors, for example one or more transcription factors from Table 1 and/or Table 2, may be introduced into the PSCs by contacting transcription factor proteins or transcription factor nucleic acids, such as mRNAs encoding transcription factors, with the population of PSCs. Programming cells though contact with transcription factor nucleic acids (Warren L et al. *Cell Stem Cell.* 2010 Nov. 5; 7(5):618-30) or proteins (Zhou H, et al Cell Stem Cell. 2009 May 8; 4(5):381-4) is well-known in the art and any suitable technique may be employed. For example, the combination of transcription factor proteins or nucleic acids may be cultured in the presence of the PSCs under conditions which allow for entry of the proteins or nucleic acid into the cell. In some embodiments, entry of transcription factor proteins into the cell may be facilitated by a membrane penetrating peptide, which may be linked or attached to the transcription factor proteins. The combination of transcription factor proteins or nucleic acids may be introduced into the PSCs by traditional methods such as lipofection, electroporation, calcium phosphate precipitation, particle bombardment and/or microinjection, or may be delivered into cells by a protein delivery agent. For example, the combination of transcription factor proteins or nucleic acids can be introduced into cells by covalently or non-covalently attached lipids, e.g. a myristoyl group.

Transcription factor nucleic acids for direct delivery into PSCs may be translatable by endogenous translation factors within the cell. Suitable synthetic mRNAs may be modified. For example, 5-methylcytidine may be substituted for cytidine, and pseudouridine for uridine, followed by phosphatase treatment to produce the transcription factor nucleic acids (Zhou H, et al 2009).

In other embodiments, the combination of transcription factors, for example GATA1, FLI1 and TAL1 and optionally one or more additional transcription factors, for example one or more transcription factors from Table 1 and/or Table 2, may be introduced into the PSCs by activating expression of endogenous nucleic acid sequences encoding the transcription factors in the population of PSCs. Suitable techniques for endogenous gene activation include Zinc Finger or Transcription like Activator (TAL) techniques and are well established in the art (see for example Hum Gene Ther. 2012 May 15; Zhang P et al. Hum Gene Ther. 2012 November; 23(11):1186-99).

In preferred embodiments, the PSCs are forward programmed in a chemically defined medium (CDM). A CDM is a nutritive solution for culturing cells which contains only specified components, preferably components of known chemical structure. A CDM is devoid of components which are not fully defined, for example serum or proteins isolated therefrom, such as Foetal Bovine Serum (FBS), Bovine Serum Albumin (BSA), and feeder or other cells. In some embodiments, a CDM may be humanised and may be devoid of components from non-human animals. Proteins in the CDM may be recombinant human proteins Suitable CDMs are well known in the art and described in more detail below.

Media and ingredients thereof may be obtained from commercial sources (e.g. Gibco, Roche, Sigma, Europabio-products, Cellgenix, Life Sciences). In a humanised CDM, for example BSA may be replaced in CDM by Polyvinyl alcohol (PVA), human serum albumin, Plasmanate™ (human albumin, alpha-globulin and beta globulin: Talecris Biotherapeutics NC USA) or Buminate™ (human albumin: Baxter Healthcare), all of which are available from commercial sources.

Suitable CDMs include Knockout (KS) medium supplemented with 4 ng/ml $FGF_2$; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human FGF2; and DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin and TeSR (Ludwig et al Nat Biotech 2006 24 185).

Other suitable CDM which may be used in accordance with the present methods are known in the art (e.g. N12 medium, Johansson and Wiles CDM; Johansson and Wiles (1995) Mol Cell Biol 15, 141-151).

Suitable humanised CDMs may comprise a basal culture medium, such as IMDM and/or F12 supplemented with insulin, for example at 0.5 μg/ml to 70 μg/ml, transferin, for example at a concentration of 1.5 μg/ml to 150 μg/ml, an antioxidant, such as 1-thiolglycerol, for example at a concentration of 45 μM to 4.5 mM, lipids, and one or more of human serum albumin, polyvinyl alcohol (PVA), Plasmanate™ (human albumin, alpha-globulin and beta globulin: Talecris Biotherapeutics NC USA) or Buminate™ (human albumin: Baxter Healthcare), for example at a concentration of 0.5 mg/ml to 50 mg/ml. For example, humanised CDM include humanised Johansson and Wiles CDM, which consists of: 50% IMDM (Gibco) plus 50% F12 NUT-MIX (Gibco); 7 μg/ml insulin; 15 μg/ml transferrin; 5 mg/ml human serum albumin, polyvinyl alcohol (PVA), Plasmanate™ or Buminate™; 1% chemically defined lipid concentrate (Invitrogen); and 450 μM 1-thiolglycerol. Another suitable chemically defined medium may comprise 50% IMDM, 50% F12 NUT-MIX, 7 μg/ml insulin, 15 μg/ml transferrin, 1% chemically defined lipid concentrate, 5 mg/ml human serum albumin or Polyvinyl Alcohol (PVA) and 450 μM 1-thiolglycerol. Another suitable chemically defined medium is CellGRO SCGM™ which is commercially available (Cellgenix, DE).

Following the introduction of the combination of reprogramming factors into the PSCs, the cells may be cultured in a pluripotency cell culture medium, for example CDM with Activin-A and FGF2, or mesodermal cell culture medium, for example CDM supplemented with BMP4 (e.g. rh-BMP4 at 10 ng/ml) and/or FGF2 and/or LY294002 for 1 or more, 2 or more, 3 or more, 4 or more, or 5 or more days, preferably about 2 days.

The cells may then be cultured in an appropriate megakaryocyte (MK) programming medium. For example, population of cells may be cultured in a chemically defined medium (CDM) supplemented with TPO (Thrombopoietin) and/or SCF (Stem Cell Factor) and/or IL1B, (all preferably recombinant human proteins).

The amino acid sequences of TPO, SCF and IL1B are readily available on public databases. For example, the reference amino acid sequence of human TPO (Thrombopoietin: also known as THPO: Gene ID 7066) has the NCBI database entry NP_000451.1 GI:4507493; the reference amino acid sequence of human SCF (Stem Cell Factor: also known as KITLG: Gene ID 4254) has the NCBI database entry NP_000890.1 GI:4505175 and the reference amino acid sequence of human IL1B (Interleukin 1 beta: Gene ID 3553) has the NCBI database entry NP_000567.1 GI:10835145.

TPO, SCF and IL1B may be produced by synthetic or recombinant means or obtained available from commercial suppliers (e.g. R&D Systems, Minneapolis, Minn., USA; Sigma-Aldrich Co. LLC USA, EMD Millipore MA USA). For example, the pluripotent cells may be cultured by a method comprising;
(i) culturing said pluripotent cells in mesoderm medium comprising FGF2 and BMP4; and,
(ii) further culturing said cells in MK programming medium comprising TPO and/or SCF, preferably TPO and SCF.

Suitable media are known in the art (Cell Stem Cell. 2011 Aug. 5; 9(2):144-55; Dev Cell. 2011 May 17; 20(5):597-609; Blood. 2008 Jun. 1; 111(11):5298-306) and are described in more detail below.

Suitable cell culture conditions are well known in the art (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)).

Methods for culturing mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430). Media and ingredients thereof may be obtained from commercial sources (e.g. Gibco, Roche, Sigma, Europa bioproducts, R&D Systems). Standard mammalian cell culture conditions may be employed, for example 37° C., 21% Oxygen, 5% Carbon Dioxide. Culture medium is preferably changed every two days and cells allowed to settle by gravity.

The population of pluripotent stem cells may be cultured for at least 7 days after introduction of the combination of transcription factors.

Megakaryocyte progenitors may be identified in the cell culture after at least 4, 5, 6, or 7 or more days.

In some embodiments, a method may comprise identifying or confirming the identity of the megakaryocyte progenitor cells or mature megakaryocytes in the culture.

In some embodiments, cells may be tested for presence of cell markers associated with the megakaryocyte progenitor cells, for example to identify or confirm their identity. Cells which express the markers may be identified as megakaryocyte progenitor cells. For example, megakaryocyte progenitor cells may identified by expression of CD34 and CD41a as described above but no expression of CD42a and CD42b.

Megakaryocyte progenitor cells do not express the pluripotency associated markers, such as Oct4, Sox2, Alkaline Phosphatase, SSEA-3, Nanog, SSEA-4 and Tra-1-60, which are expressed by PSCs or display reduced expression relative to PSCs.

A method may further comprise isolating and/or purifying the forward programmed megakaryocyte progenitor cells. Megakaryocyte progenitors may be separated from other cell types in the population using any technique known to those skilled in the art, including those based on the recognition of extracellular epitopes by antibodies and/or magnetic beads or fluorescence activated cell sorting (FACS), including the use of antibodies against extracellular regions of characteristic markers.

The megakaryocyte progenitor cells may be cultured and/or expanded to generate a homogenous or substantially homogenous population of cells. Suitable techniques for mammalian cell culture are well known in the art and described elsewhere herein.

A method may comprise monitoring or detecting the expression of one or more megakaryocyte progenitor cell markers and/or one or more pluripotent cell markers in cells in the population. This allows the extent of forward programming in the population to be determined as it is cultured.

At least 5%, at least 10%, at least 20%, at least 30%, at least 40%, at least 50% or at least 60% of the population of PSCs may become megakaryocyte progenitor cells following forward programming as described herein.

Megakaryocyte progenitor cells produced by the present methods may be substantially free from other cell types. For example, a population of megakaryocyte progenitors produced by a method described herein may contain 80% or more, 85% or more, 90% or more, or 95% or more megakaryocyte progenitor cells, following culture.

The population of megakaryocyte progenitor cells may be cultured and/or expanded and optionally stored.

Following the production of a population of megakaryocyte progenitor cells by forward programming, the methods described herein may further comprise allowing the population of megakaryocyte progenitor cells to differentiate into mature megakaryocyte cells, for example by culture in a megakaryocyte maturation medium.

For example, megakaryocyte progenitor cells may be passaged, for example from day 7 or day 10, into suspension culture plastic dishes in a megakaryocyte maturation medium comprising CDM (e.g. CellGRO SCGM™) supplemented by TPO and/or IL1-beta and/or SCF; and then cultured for an additional 5-7 days or 5-15 days, up to 10-15 days.

In some embodiments, the megakaryocyte progenitor cells may be cultured in a megakaryocyte maturation medium comprising CDM (e.g. CellGRO SCGM™) supplemented by TPO and/or IL1-beta and/or SCF, preferably TPO and IL1-beta, from day 10 onwards for an additional 5-7 days or 8-12 days, preferably 10 days.

Typically, the cells are cultured for 18 to 22 days from TF transduction, preferably about 20 days, to produce mature megakaryocyte cells.

The mature megakaryocyte cells may be isolated, purified and/or stored according to standard techniques.

In preferred embodiments, a population of mature megakaryocyte cells produced by a method described above may be pure or substantially pure and may not require further sorting or purification. For example, at least 80%, at least 90% or at least 95% of cells in the population of mature megakaryocyte cells may express CD41a (i.e. CD41a+ cells). At least 30%, at least 40% or at least 50% of cells in the population may express CD42a (i.e. CD42a+ cells). In some preferred embodiments, at least 95% of cells in the population express CD41a and at least 50% of cells in the population may express CD42a.

In some embodiments, mature megakaryocyte cells produced as described herein may be used in the production of platelets. For example, a method described herein may comprise allowing one or more of the mature megakaryocyte cells to produce platelets.

Another aspect of the invention provides a population of megakaryocyte progenitor cells or mature megakaryocytes produced as described herein.

Populations of megakaryocyte progenitor cells and mature megakaryocytes produced by forward programming as described herein are described in more detail above.

Megakaryocyte progenitor cells produced by forward programming as described herein may be highly proliferative (for example over 28 days or more).

Mature megakaryocyte cells produced by forward programming and differentiation as described herein may generate and/or release functional platelet like particles (PLPs) in vitro.

Another aspect of the invention provides the use of a population of megakaryocyte progenitor cells or mature megakaryocytes produced as described herein in the production of platelets.

Another aspect of the invention provides megakaryocyte progenitor cells or mature megakaryocytes produced as described herein for use in methods of treatment of haematological conditions as described herein and methods of treatment of haematological conditions which comprise administering megakaryocyte progenitor cells or mature megakaryocytes produced as described herein to an individual in need thereof.

Megakaryocyte progenitor cells or mature megakaryocytes produced as described herein may also be useful in screening. Screening may include drug or small molecule screening. For example, the isolated programmed cells may be contacted with a test compound and the effect of the test compound on the cells is determined. Screening may also include functional genomic screening. For example, a gene may be suppressed, knocked out or otherwise inactivated in the isolated reprogrammed cells and the effect of the inactivation on the cells determined.

In some embodiments, megakaryocyte progenitor or mature megakaryocytes cells may be produced from iPS cells as described herein. The iPS cells may be derived from normal differentiated cells or from differentiated cells having a disease phenotype or genotype, for example from an individual with a disease condition. After programming, the megakaryocyte progenitor cells or mature megakaryocytes may express a detectable reporter or display an observable cellular phenotype which differs between disease-affected cells and normal cells. The megakaryocyte progenitor cells or mature megakaryocytes may be exposed to test compounds and the effect of the test compound on the reporter expression or observable cellular phenotype determined. Compounds which cause the megakaryocyte progenitor cells or mature megakaryocytes to revert from disease cell state to the normal state may be identified. Alternatively, the one or more genes in the megakaryocyte progenitor cells or mature megakaryocytes may be inactivated, for example by targeted mutation or RNAi suppression, and the effect of the inactivation on the reporter expression or observable cellular phenotype determined. Genes whose inactivation causes the cells to revert from disease cell state to the normal state may be identified.

Screening may include toxicology screening. For example, the isolated megakaryocyte progenitor cells may be contacted with a test compound at various concentrations that mimic abnormal/normal concentrations in vivo. The effect of the test compound on the cells may be determined and toxic effects identified. Toxicology screening is well known in the art (see for example Barbaric I et al. Biochem Soc Trans. 2010 August; 38(4):1046-50).

Forward programmed megakaryocyte progenitor cells (and cells derived from the programmed cells, such as mature megakaryocytes and platelets) may also be used for the treatment of an individual, for example for the treatment of a platelet or megakaryocyte related condition. The individual may be the same individual from whom the original IPS cells were obtained.

In some embodiments, the forward programmed megakaryocyte progenitor cells or mature megakaryocytes may, for example, be admixed with a pharmaceutical acceptable carrier in a pharmaceutical composition. The composition may be administered to the individual ((Leukemia. 2008 January; 22(1):203-8).

Forward programmed megakaryocyte progenitor cells and cells derived from the programmed cells, such as mature megakaryocytes, may also be used for disease modelling. For example, cells may be programmed into megakaryocyte progenitors which are affected in a disease condition, either directly or by differentiating into the affected megakaryocytes or platelets. The effect of the mutation on the cellular phenotype may be studied and the genetic and/or biochemical interactors that contribute to the cellular pathology of the disease may be identified and/or characterised.

Another aspect of the invention provides a method of screening for a compound useful in the treatment of a disease condition, in particular a haematological condition, for example a thrombocytopenic or other platelet-related condition, including essential thrombocytosis, congenital amegakaryocytic thrombocytopenia (CAMT), Thrombocytopenia-absent radius syndrome (TAR), Bernard Soulier syndrome (BSS), Gray platelet syndrome (GPS) and Glanzmann thrombasthenia, comprising;

contacting a population of megakaryocyte progenitor cells produced by a method described above with a test compound, and;

determining the effect of the test compound on said cells and/or the effect of said reprogrammed cells on the test compound.

Suitable forward programmed megakaryocyte progenitor cells are described above.

The megakaryocyte progenitor cells may display a disease phenotype and the effect of the test compound on one or more disease pathologies in the reprogrammed cells may be determined. A decrease or amelioration of one or more disease pathologies in the reprogrammed cells in the presence, relative to the absence of test compound is indicative that the test compound may be useful in the treatment of the disease in the individual.

Suitable disease conditions and phenotypes are described above.

The forward programmed megakaryocyte progenitor cells may display a normal phenotype and the effect of the test compound on the growth, differentiation or viability of the reprogrammed cells or the ability of the reprogrammed cells to perform one or more cell functions may be determined. In some embodiments, cells may be modified to express reporters that can be used to measure particular cell functions or attributes. A decrease in growth, viability or ability to perform one or more cellular functions may be indicative that the compound has a cytotoxic effect (see for example, Barbaric I et al Biochem Soc Trans. 2010 August; 38(4): 1046-50).

The data set out herein shows that GATA1 and FLI1 are also able to drive forward programming in the absence of TAL1. Other aspects and embodiments of the invention provide all of the aspects and embodiments described above with the transcription factor TAL1 omitted from the combination of transcription factors.

Other aspects and embodiments of the invention provide the aspects and embodiments described above with the term "comprising" replaced by the term "consisting of" and the aspects and embodiments described above with the term "comprising" replaced by the term "consisting essentially of".

Various further aspects and embodiments of the present invention will be apparent to those skilled in the art in view of the present disclosure.

All documents and database entries which are mentioned in this specification are incorporated herein by reference in their entirety for all purposes.

The transcription factor symbols and names set out herein are the unique official HUGO Gene Nomenclature Committee (HGNC) symbols and names that have been assigned to that transcription factor (see Gray K A et al Nucleic Acids Res. 2013 Jan. 1; 41(D1):D545-52; and the HGNC Database, HUGO Gene Nomenclature Committee (HGNC), EMBL Outstation—Hinxton, European Bioinformatics Institute, Wellcome Trust Genome Campus, Hinxton, Cambridgeshire, CB10 1SD, UK).

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments of the invention which are described. Thus, the features set out above are disclosed for use in the invention in all combinations and permutations.

Certain aspects and embodiments of the invention will now be illustrated by way of example and with reference to the figures and tables described herein.

Figure 3:
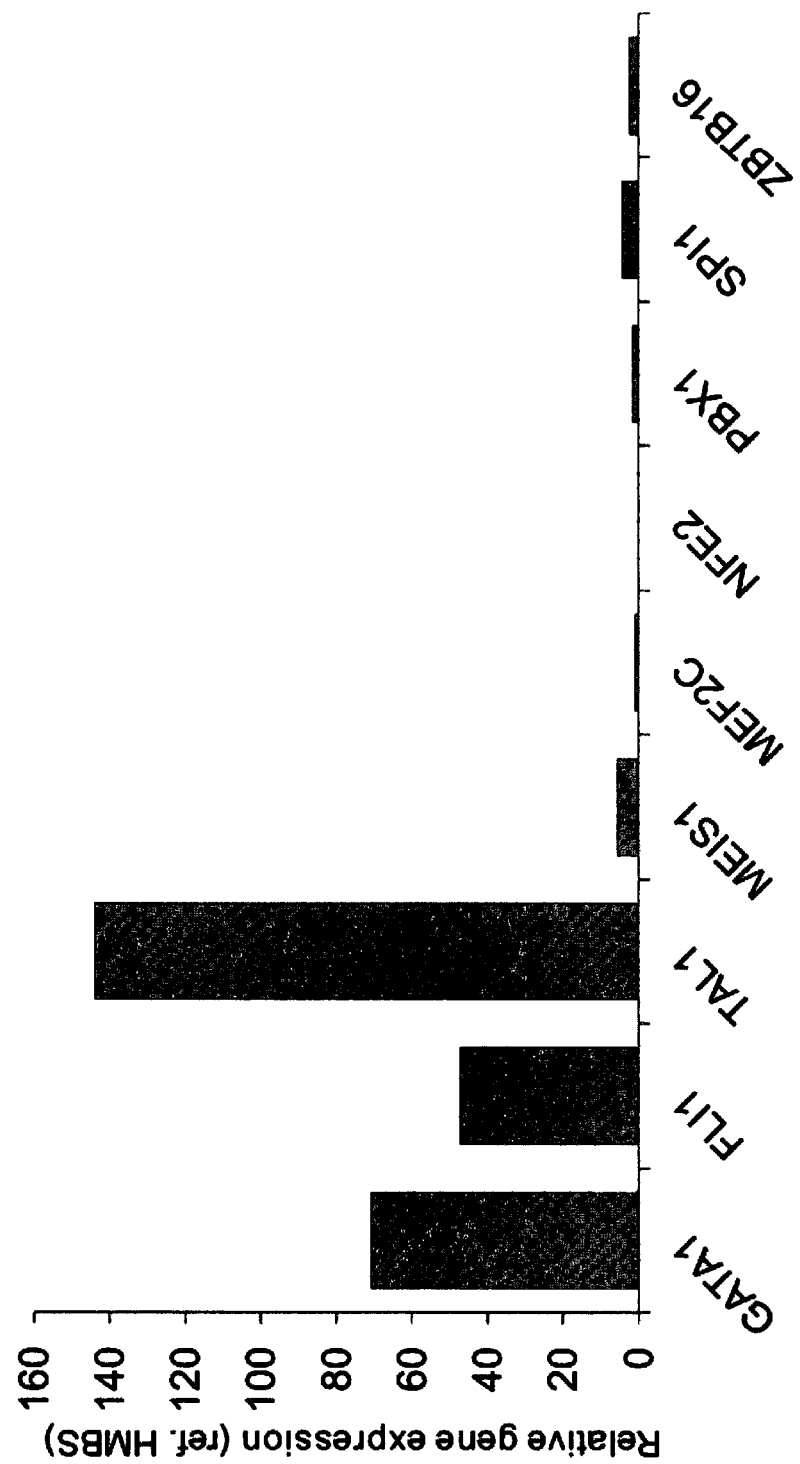

FIG. 3 shows transgene expression levels quantified by RT-QPCR in flow cytometry sorted CD41a+ cells generated 7 days after lentiviral transduction of the hESC#1 line with the 9 TFs on fibronectin coated plates and maintained in pluripotent medium (FGF2+Activin-A) for 2 days followed by MK medium (TPO+SCF) for 5 days.

Figure 4:
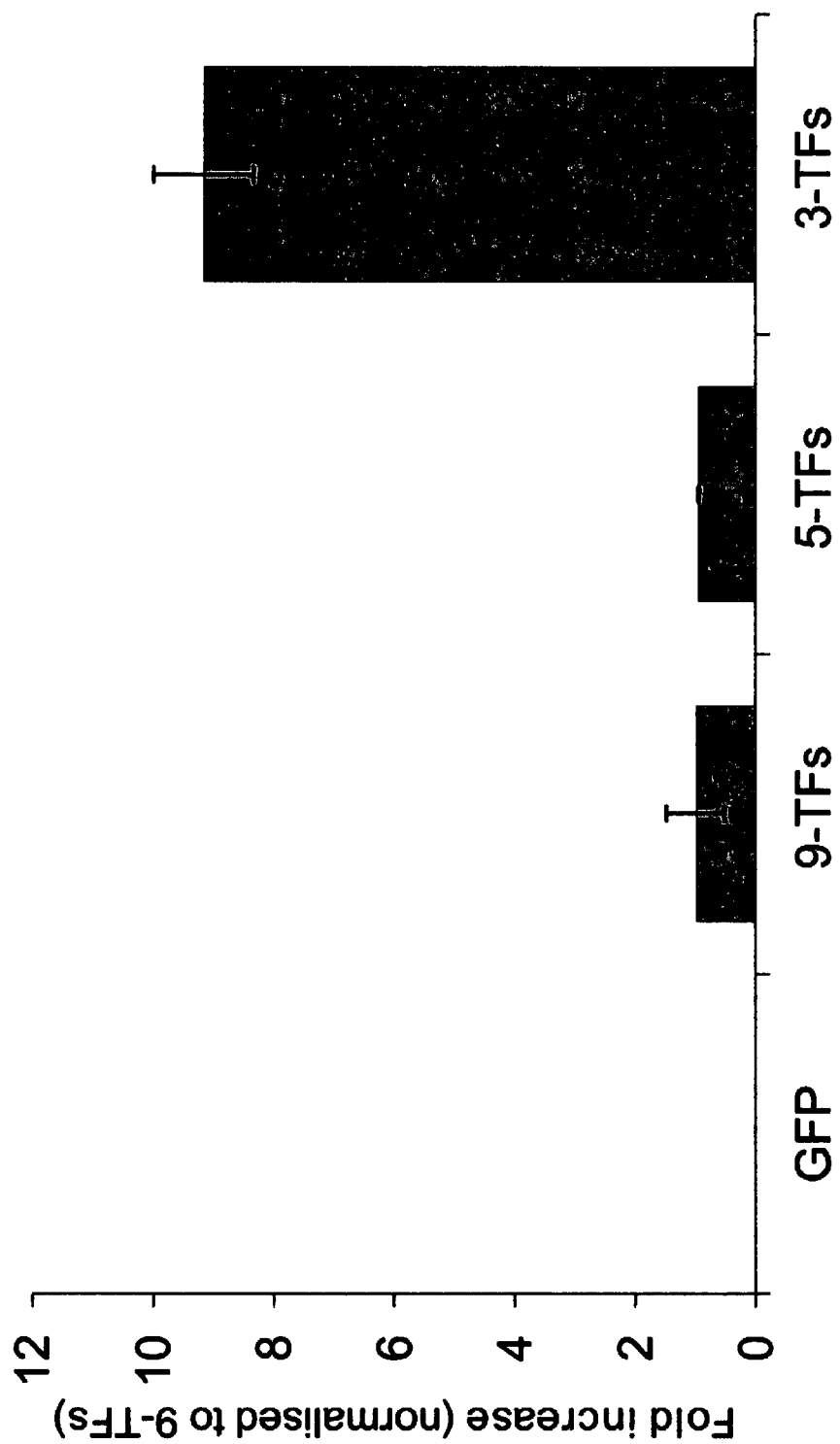

FIG. 4 shows the fold increase of CD41a+ cells relative to the 9-TFs combination (mean±sem, n=3/3/1/2 respectively) in hESC#1 cells transduced with different combinations of TFs using a 2 day mesoderm induction and measured by flow cytometry at day 7. 3TFs combination is shown as the most effective for MK-FoP.

Figure 5:
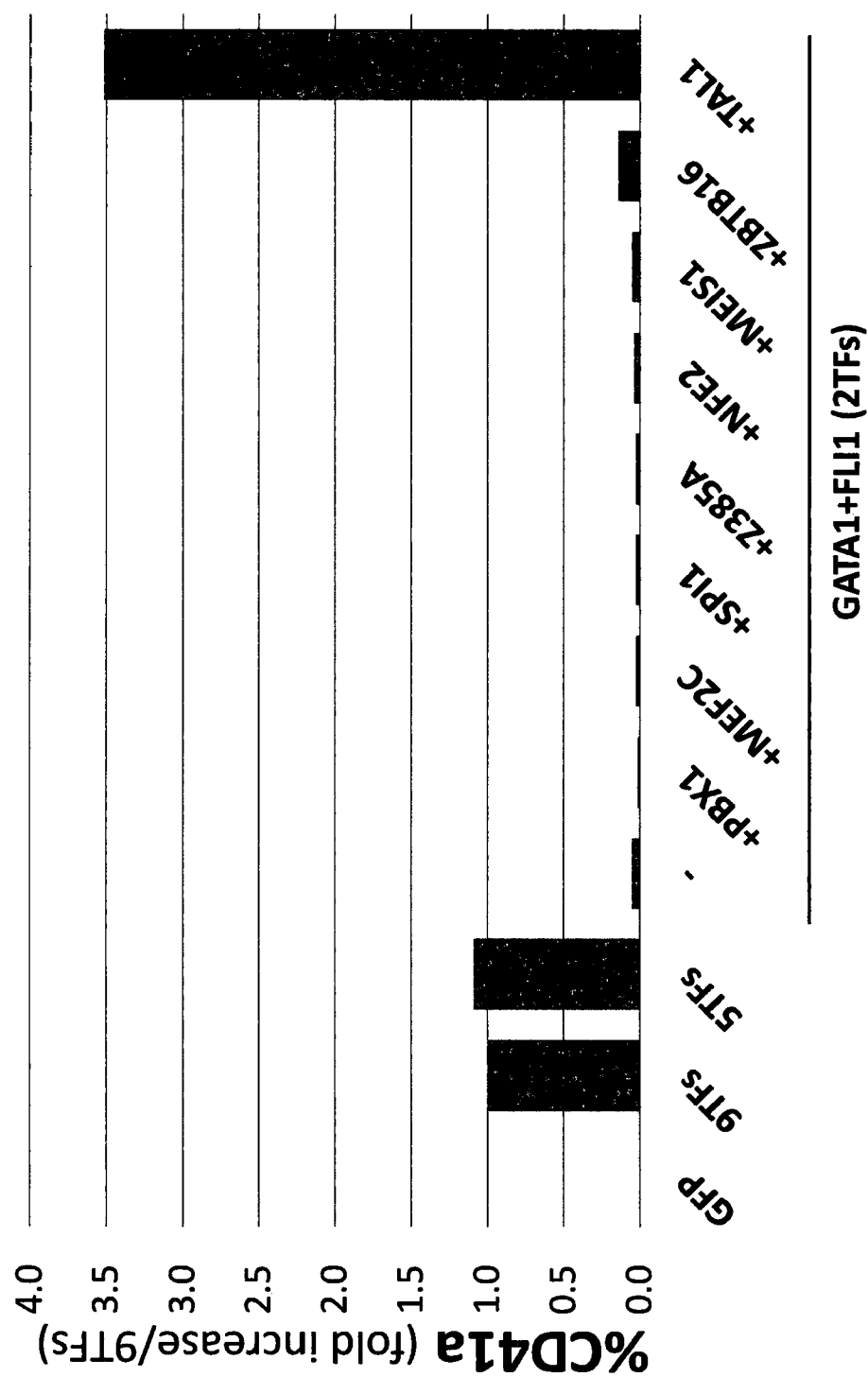

FIG. 5 shows the fold increase of CD41a+ cells relative to the 9-TFs in hESC#1 cells transduced with different combinations of TFs under pluripotent conditions without mesoderm induction and measured by flow cytometry at day 7. 3TFs combination is shown as the most effective for MK-FoP.

Figure 6:
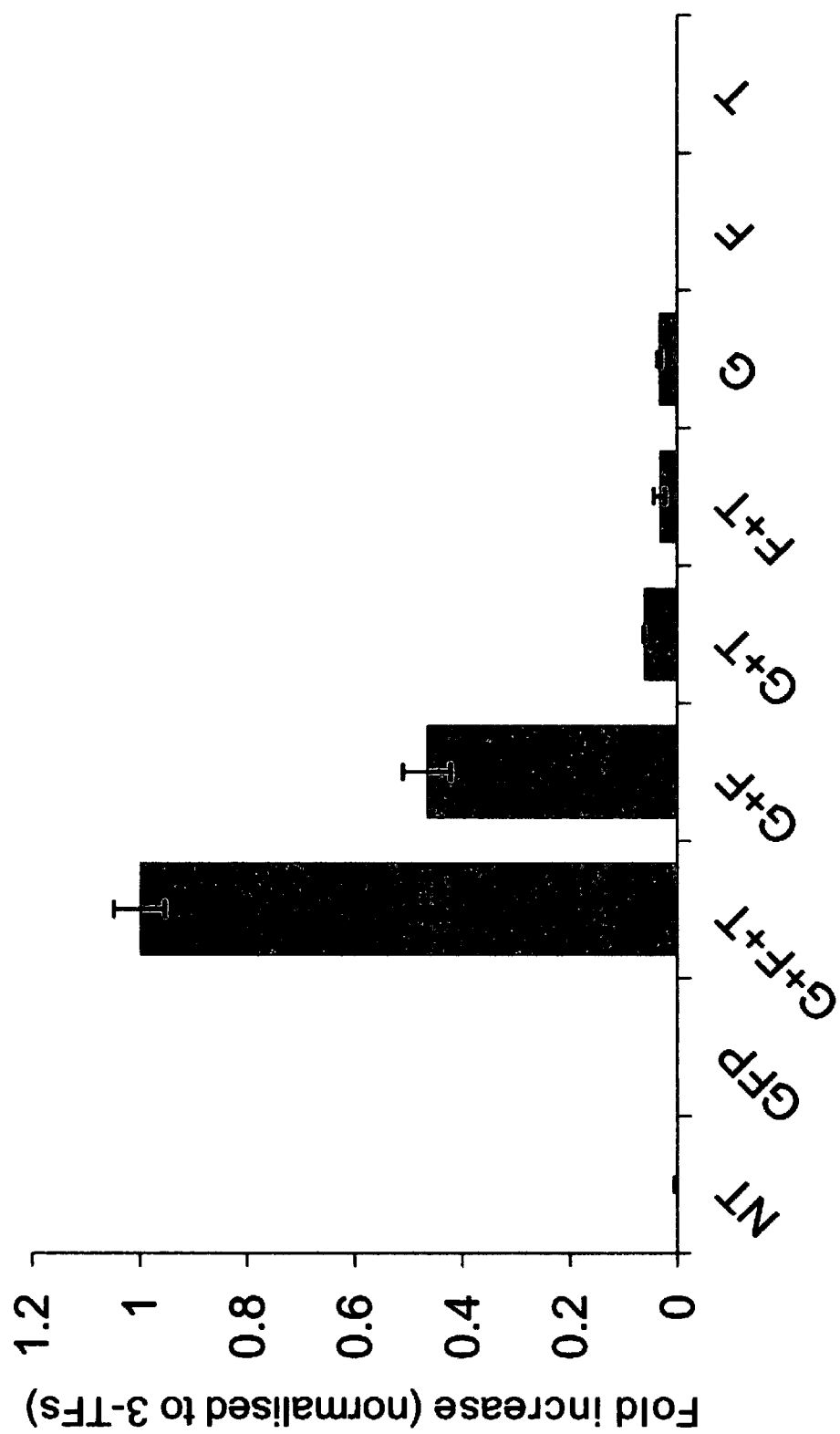

FIG. 6 shows the fold increase of CD41a+ cells relative to the 3-TFs combination (mean±sem, n=2) in hiPSC#1 cells transduced with all permutations of the 3-TFs combination using 2 days mesoderm induction and measured by flow cytometry at day 7.

Figure 7:
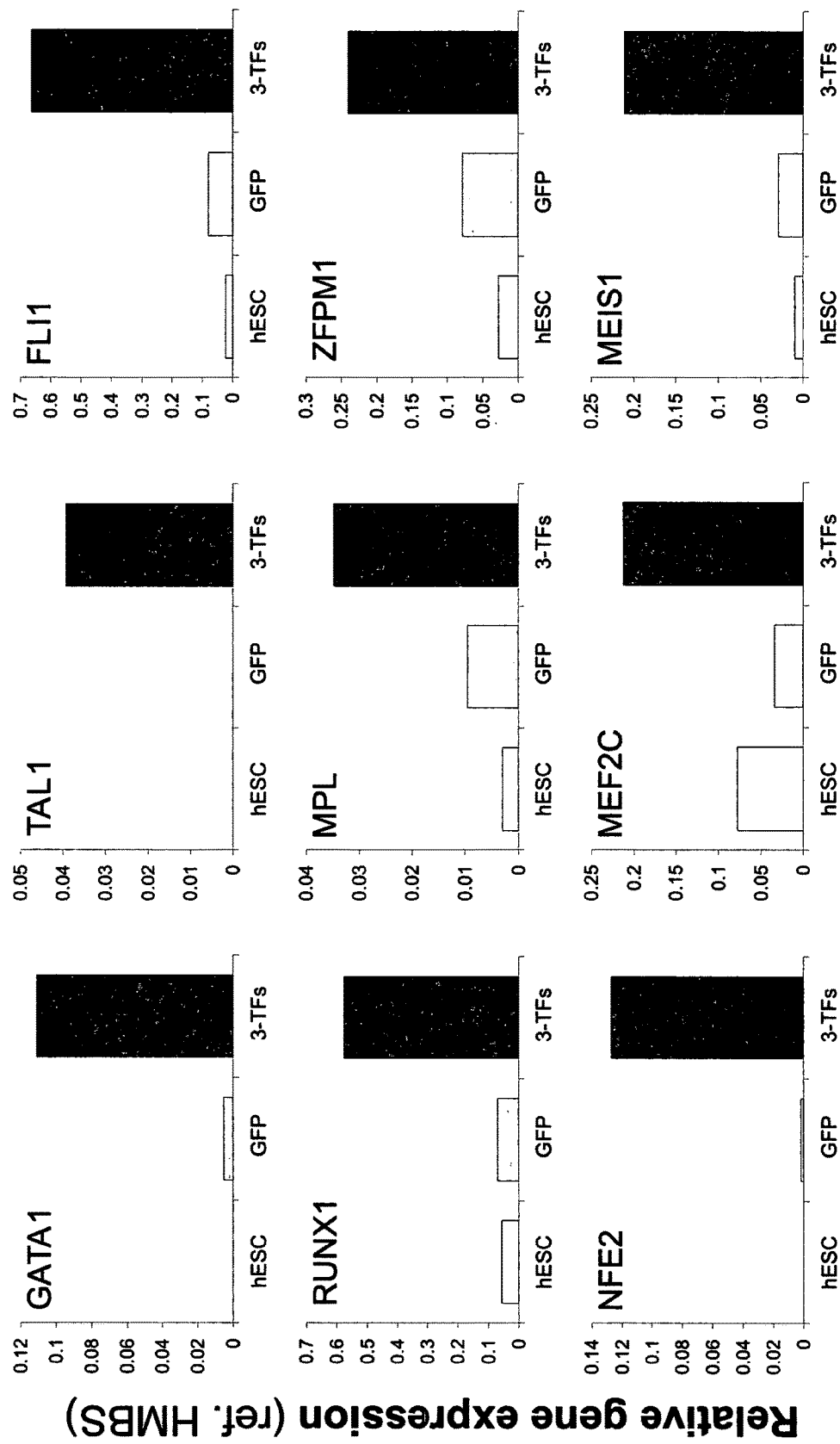

FIG. 7 shows real time quantitative PCR analysis of MK gene expression at day 7 in an unsorted population: HES3 (hESC#2) ESC line before and after forward programming protocol (21% CD41a+ at day 7). ES: pluripotent ESC line; GFP: GFP transduced cells were cultivated in the same conditions as for 3TFs transduced cells.

Figure 8:
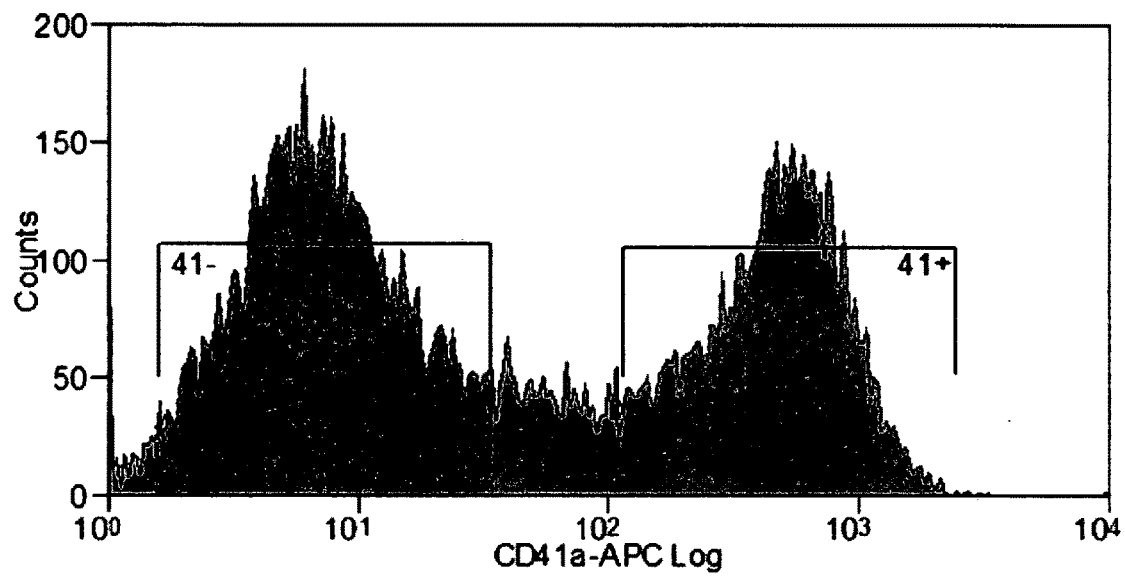
Figure 8:

FIG. 8 shows the megakaryocytic potential of cells sorted by flow cytometry based on CD41a expression at day 7 following transduction of hiPSC#2 line with the 3-TFs combination. The megakaryocytic potential of sorted cells was tested using the Megacult clonogenic assay (1,000 cells in duplicate). A representative megakaryocyte colony obtained from a CD41a+ cell and co-expressing CD41a and CD42b as detected by immunofluorescence is shown.

Figure 9:
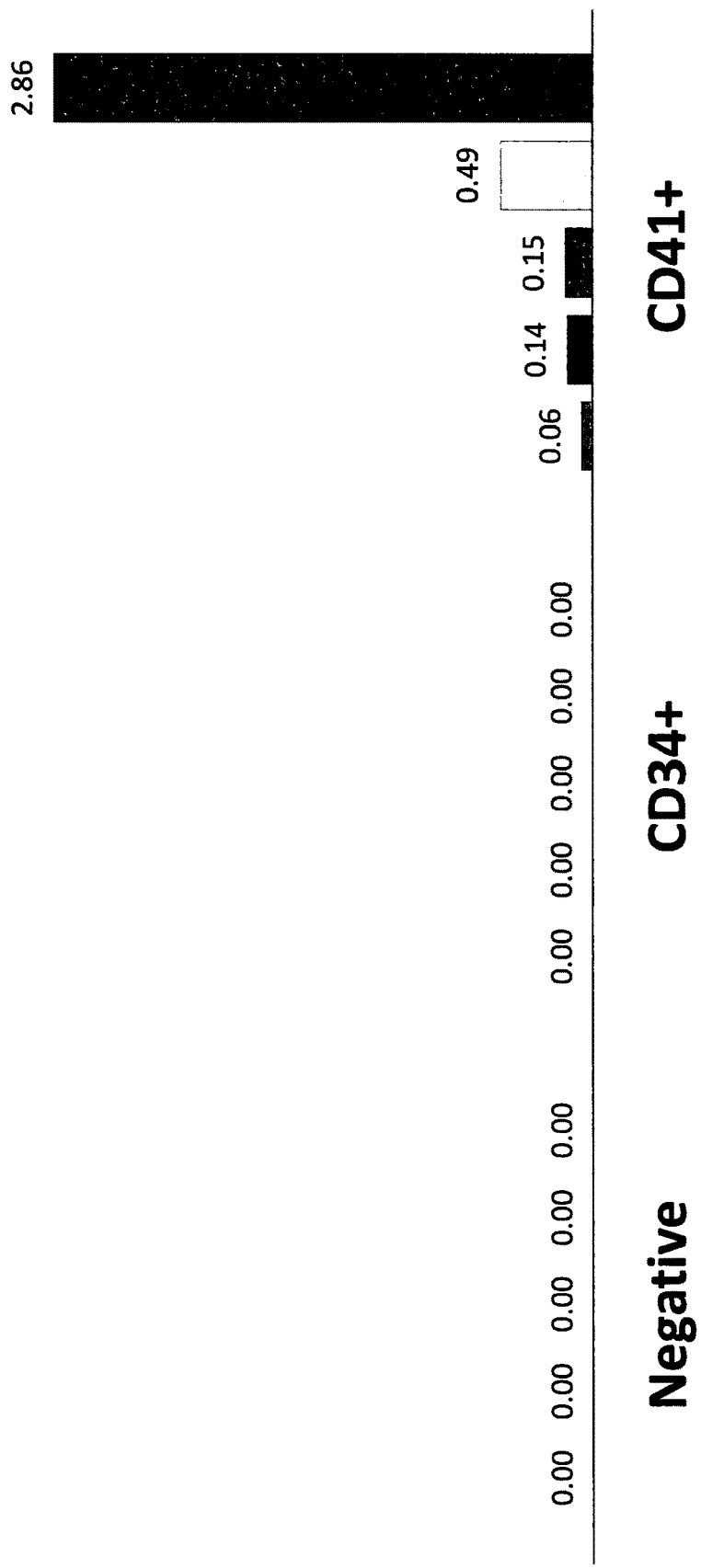

FIG. 9 shows real-time quantitative PCR analysis of MK gene expression at day 7 in sorted populations following forward programming of the hESC#1 line.

Figure 10:
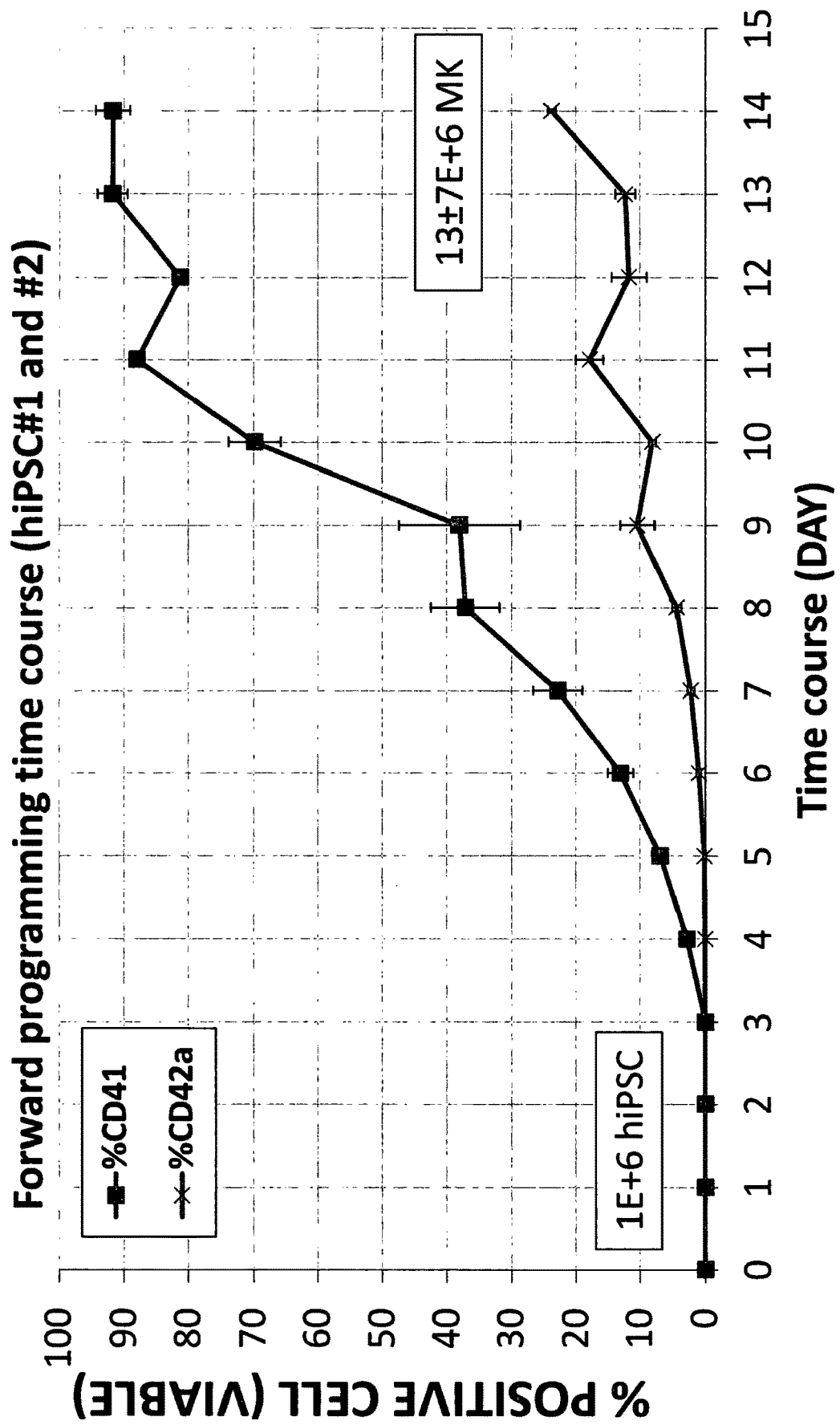

FIG. 10 shows a time course flow analysis of the mean values+/−SD of surface marker expression using forward programming protocol on the hiPSC#1 and #2 lines.

Figure 11:
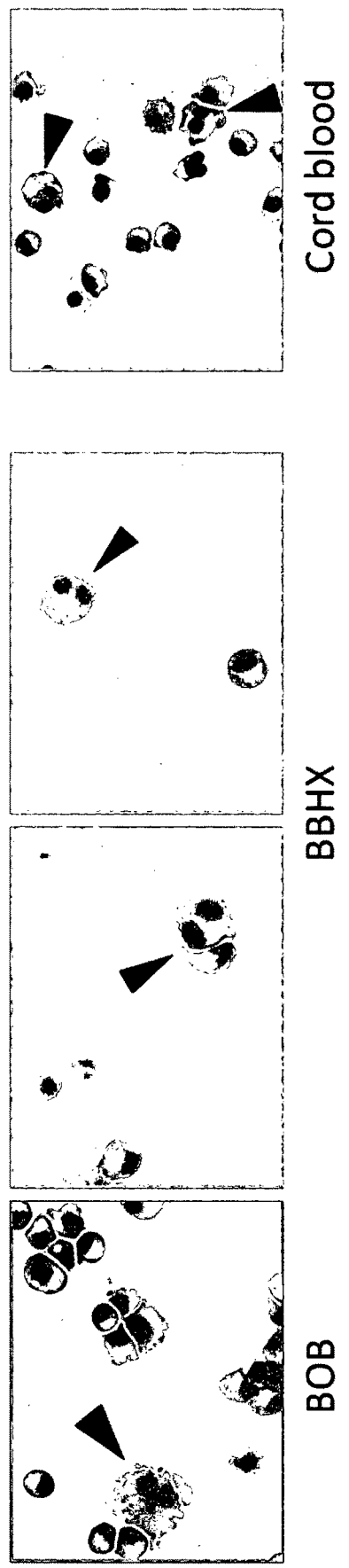

FIG. 11 shows the results of cytospin and Romanowsky staining: polyploid MK are produced from forward programmed hiPSC#1 and #2 lines (BOB and BBHX) and are similar to cord blood derived MKs.

Figure 12:
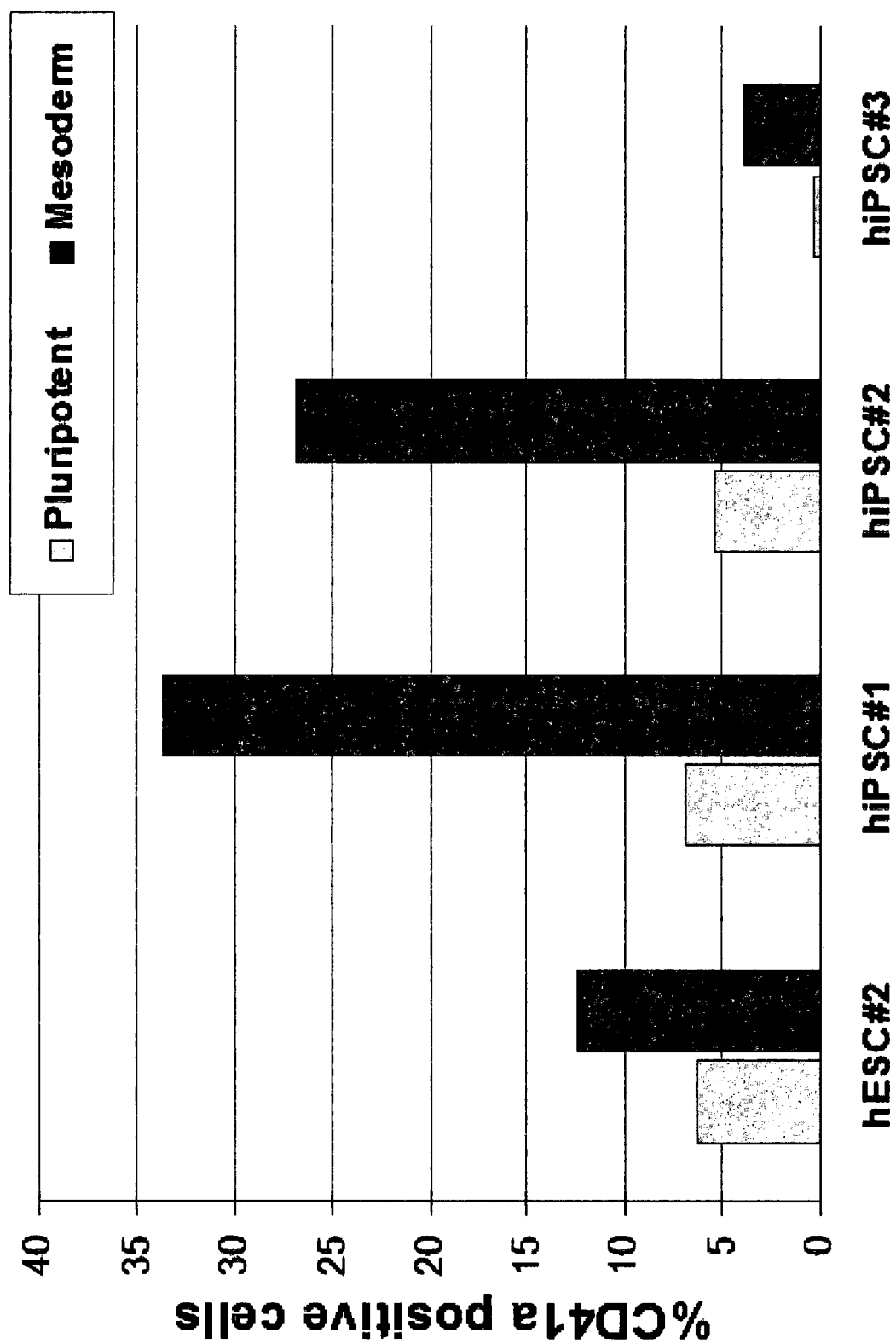

FIG. 12 shows the percentages of CD41a expressing cells produced when human pluripotent stem cells sown on fibronectin coated plates were transduced in parallel with the 3-TFs and kept for 2 days in pluripotent (FGF2+Activin-A) or mesoderm (FGF2+BMP4+LY294002) medium followed by MK medium (TPO+SCF) for 6 days.

Figure 13:
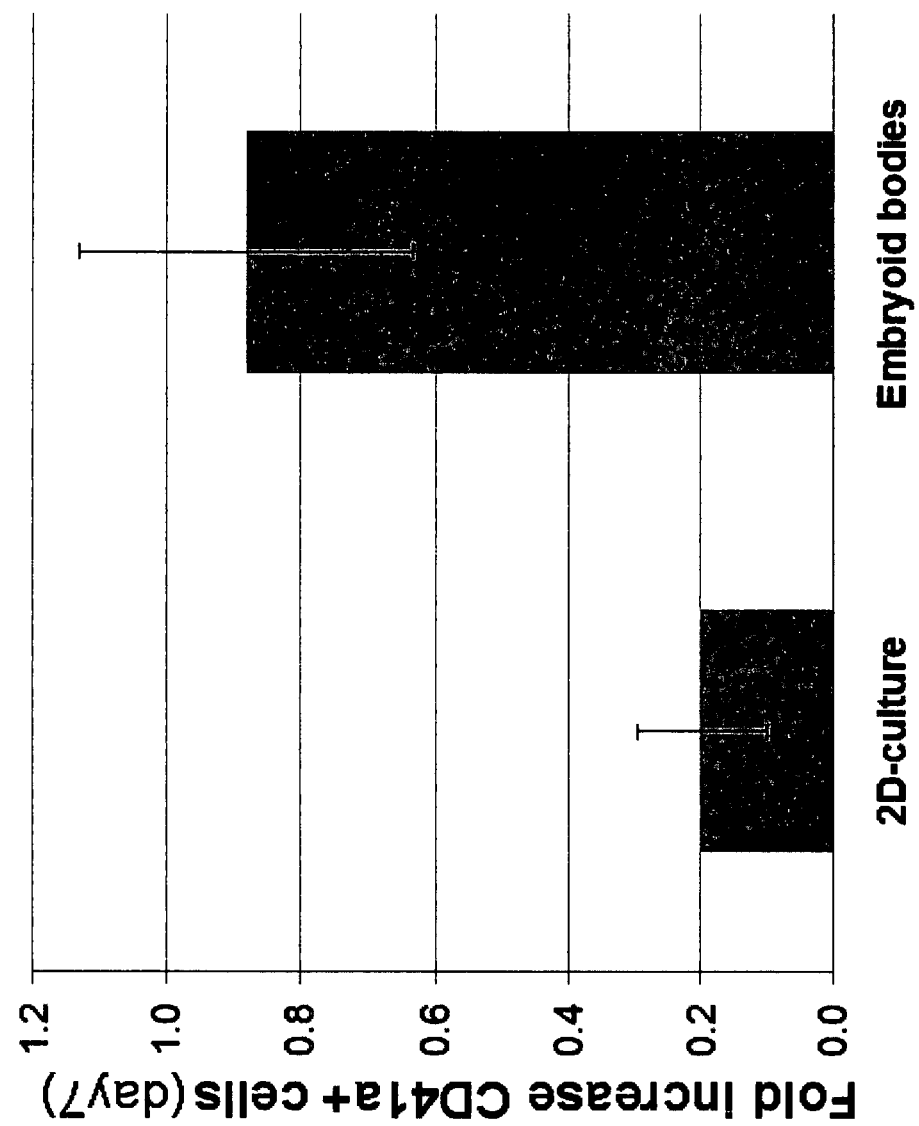

FIG. 13 shows histograms representing the CD41a+ cells fold increase relative to the hiPSC input (mean±sem, n=4/3 respectively) when the hiPSC#2 line was sown in fibronectin coated plates (2-D culture) or induced to form embryoid bodies by forced aggregation of single cells and subsequently transduced with the 3-TFs. Cells were kept 2 days in mesoderm medium and 5 days in MK medium.

Figure 14:
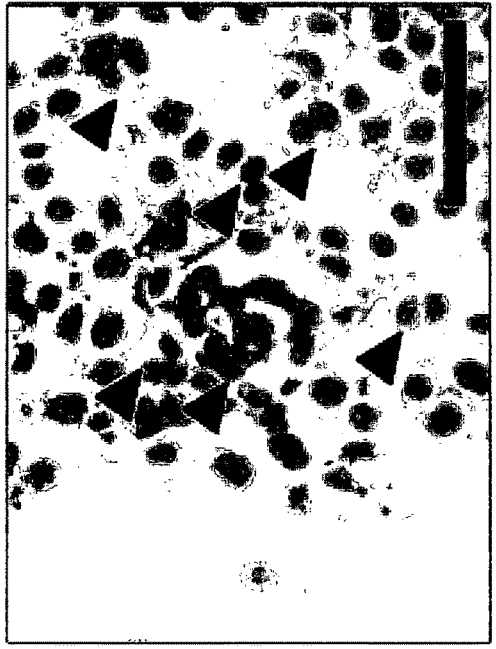
Figure 14:
Figure 14:
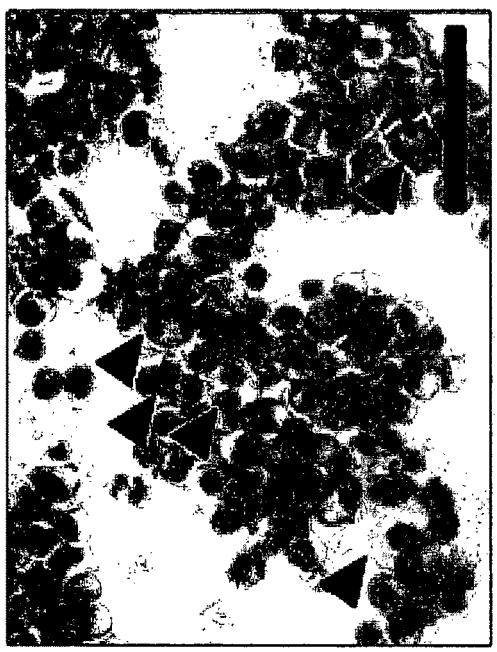
Figure 14:

FIG. 14 shows the morphology of day 20 hiPSC-MKs and CB-MKs analysed after Romanowsky staining. Arrowheads point to cells showing several nuclei. Scale bars, 100 um.

Figure 15:
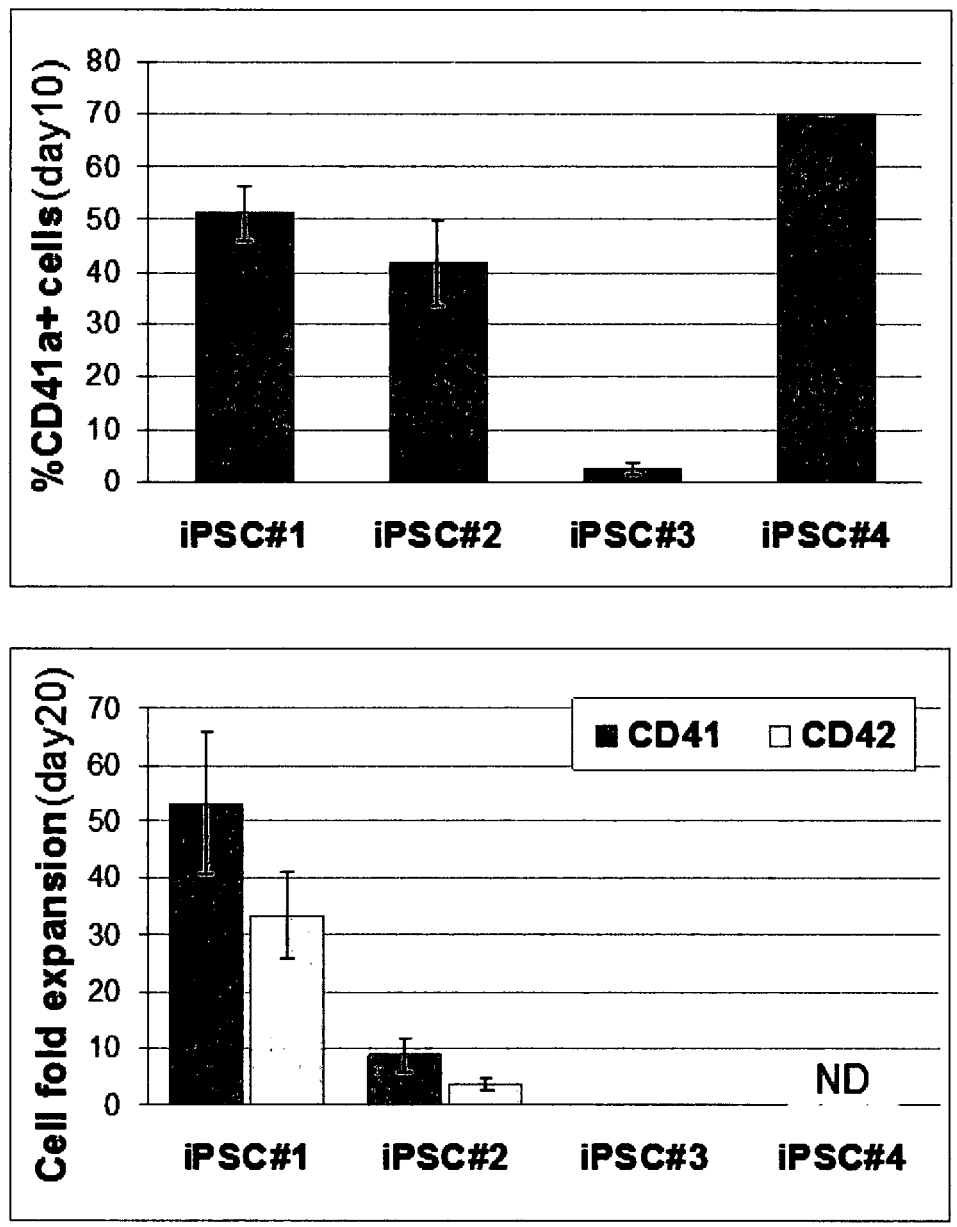

FIG. 15 upper panel shows histograms representing the percentages of CD41a+ cells generated at day 10 (mean±sem, n=11/6/2/1 respectively) from a variety of hiPSC lines using the optimised 3-TFs forward programming protocol. Lower panel shows cell fold expansion at day 20 for total and mature megakaryocytes (CD41a and CD42b positive cells respectively) relative to the hiPSC input (mean±sem, n=6/6/2 respectively). ND not done.

Figure 16:
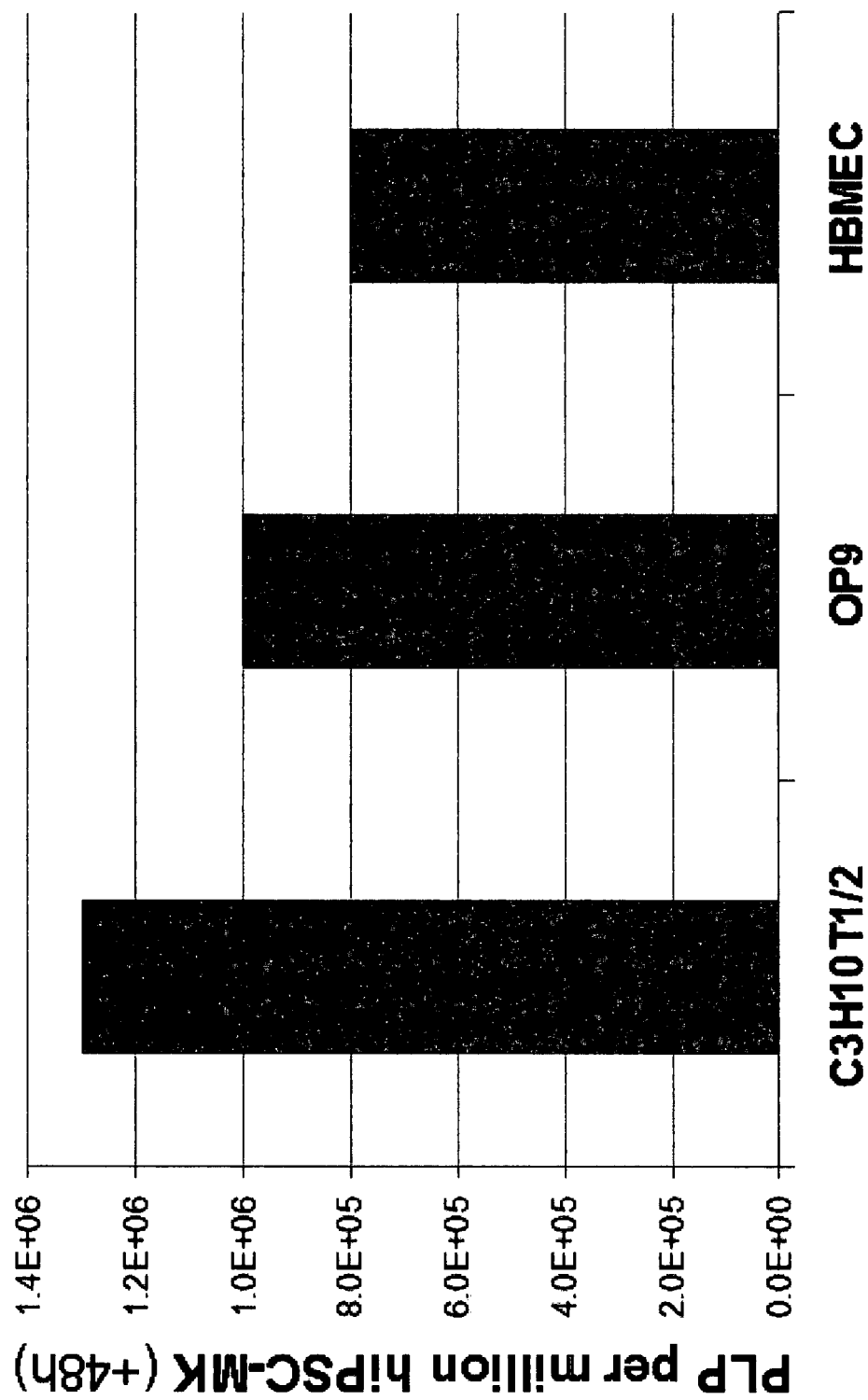

FIG. 16 shows histograms representing the amount of PLPs generated per hiPSC-MK input after hiPSC#1 day 20 MKs were sowed in parallel on different stromal cell lines.

FIG. 17 presents Table 1, which shows 46 candidate TFs selected upon analysis of protein-protein interaction network using VisANT software, integrating interactions with chromatin remodelling factors and level of gene expression. 14 transcription factor candidates cloned into lentiviral vector backbones are highlighted.

Table 2 shows 13 TFs identified from differential expression between cord blood or peripheral blood derived megakaryocytes and hiPSC-MKs Table 3 shows an enrichment analysis for biological processes using the DAVID bioinformatics resource which indicates significant enrichment for megakaryocyte/platelet function genes in hiPSC-MKs compared to the starting hiPSCs. Input gene expression dataset from CD42b sorted hiPSC-MKs (line #1 and #2) and hISPC pluripotnet culture analysed on an Illumina Human HT-12 v4 BeadArray (hiPSC#1-MK, n=4; hiPSC#2-MK, n=2; hiPSC#1, n=2).

1. Materials and Methods
1.1 Cell Lines

The human embryonic stem cell lines HES3 and H9 (from ES Cell International, Singapore and Wicell, Madison respectively) and the human iPSC lines #1-4 (A1ATD1, BBHX8, iPS40 and S4-SF5 respectively, obtained from the Cambridge Biomedical Research Centre iPSC Core Facility) are cultivated at 37 C/5% CO2 in chemically defined culture conditions as described previously (*Curr Protoc Stem Cell Biol.* 2008 March; Chapter 1:Unit 1D.4.1-1D.4.7). Briefly, cells are maintained in a chemically defined basal medium (CDM) supplemented with recombinant human FGF2 (12 ng/ml, University of Cambridge) and Activin-A (15 ng/ml, University of Cambridge) on feeder free gelatin coated wells as previously described (*Curr Protoc Stem Cell Biol.* 2008 March; Chapter 1:Unit 1D.4.1-1D.4.7) with medium changes daily.

Subculture is performed every 5-7 days by detaching pluripotent colonies by incubation in a dispase/collagenase-IV mix (1 mg/ml, Sigma Aldrich) for 45 minutes at 37° C., collecting detached colonies, breaking them down into small clumps carefully pipetting up and down with a P1000 tip and plating them onto new gelatin coated plastic dishes.

Human iPSC line derivation has been performed under appropriate ethical approval and volunteer consent were obtained (Ethics reference no. 08/H0311/201; R&D no. A091485). The iPSC lines have been derived from adult dermal fibroblasts using murine oncoretroviral vectors (hiPSC #1-3) or Sendai vectors (hiPSC #4) expressing the human OCT4, SOX2, KLF4 and MYC reprogramming factors and following subculture steps on irradiated mouse embryonic feeder cells in 20% KSR medium supplemented by rh-FGF2 as previously described.

1.2 Transcription Factor Candidate Selection

We performed a differential expression analysis focused on DNA binding protein coding genes (PANTHER) from whole genome expression data generated in the H9 hESC line (internal data, Illumina HumanWG-6 v3) and human cord blood derived MKs (*HaermAtlas, Blood.* 2009; 113: e1-9, Illumina HumanWG-6 v2). The list of 116 MK specific genes generated was further refined by removal of 21 histone coding genes and addition of 6 genes with known or potential roles in megakaryopoiesis. Using the V isANT web-based software (*Nucleic Acids Res.* 2005; 33:W352-357) for analysing networks of biological interactions, the resulting 101 candidate genes were subsequently ranked based on number of 1) internal protein interactions, 2) interaction with epigenome modifiers (HAC, HDAC, DNMT) and 3) differential expression levels. Weakly differentially expressed genes (log 2(MK-ESC)<1) were excluded from the candidate list. The final gene candidate list is eventually made of 46 factors ranked (from highest to lowest value) on 1) number of internal interactions 2) number of nodes with chromatin remodelling factors 3) differential expression value. Exceptions in the final list are the MLL and MLL3 genes which were removed since they have coding sequences of over 10 kb and are incompatible with lentiviral vectors. MCM7 was also removed since it is not known to act as a transcription factor (mini-chromosome maintenance complex). CLOCK has been added despite a low expression value (0.89) because it has reported Histone Acetyl Transferase activity.

A heatmap of differentially expressed transcription factors between cord blood or peripheral blood derived megakaryocytes and hiPSC-MKs was generated using Heatmap Builder v1.1 and a row normalised sorting algorithm (cut-off>2-fold increase, FDR1%). Each line of the heatmap represented a gene specific probe on the Illumina Human HT-12 v4 Beadarrays. Mean values of CB-MK (n=4), PB-MK (n=2), hiPSC#1 (n=4) and hiPSC#2 (n=2). The candidate list was then reduced to the 13 TF genes showing very low/null expression in hiPSC-MKs (log 2<8). These factors may play an important role in further maturation of hiPSC-MKs 1.3 Transcription Factor Cloning into Lentiviral Backbone The full human coding sequences of the 9 candidate genes (CDS of transcript variants 1, NCBI Refseq) including the 5'

Kozak concensus sequence were generated by PCR using cDNA from cord blood derived MKs as template. PCR fragments were subsequently individually cloned into the pWPT lentiviral vector backbone (Trono laboratory, Addgene 12255) in place of the eGFP coding sequence in-between the MluI and SalI restriction sites, downstream of the human EF1-alpha ubiquitous promoter. Final constructs has been checked for sequence integrity against the NCBI Refseq library before use for lentiviral vector production. Replication deficient lentiviral vector particles (LVPs) were produced by transient co-transfection of HEK 293T/17 cells (ATCC CRL-11268) with the generated pWPT constructs along with the psPAX2 and pMD2.G helper plasmids (Trono laboratory, Addgene 12260 and 12259) using TransIT-LT1 transfection reagent (MirusBIO). Crude supernatants containing LVPs were collected 48 hours after transfection, filtered through a 0.45 um membrane and DNaseI treated before concentration by ultracentrifugation or PEG-based precipitation (LentiX-concentrator, Clontech). Functional LVPs titres were determined by QPCR measurement of provirus copy number in genomic DNA of transduced HCT116 cells (ATCC CCL-247) and were in the range of 1-10E+8 TU/ml for all vectors. Human PSC lines were routinely transduced using multiplicity of infection of 20 in presence of 10 micrograms Protamine Sulfate (Sigma, P4505) per millilitre of culture medium leading to 60-80% transduction efficiencies through experiments.

1.4 MK Forward Programming

Optimised embryoid body based protocol: on transduction day (day 0), sub confluent (50-80%) human pluripotent stem cells were dissociated to single cells using TrypLE (Life Technologies) for 5 min at 37 C and viable cells counted on a haemocytometer. Embryoid body (EB) formation was initiated with $5 \times 10^5$ to $1 \times 10^6$ viable cells per well of an Aggrewell™400 plate (Stemcell Technologies, France) in order to obtain embryoid bodies (EB) of 400 to 800 cells per EB following spin aggregation (detailed protocol in Aggrewell™ Technical manual).

Importantly, lentiviral transduction was performed concomitantly to the aggregation phase. Briefly, cells were added to the well in CDM supplemented by Y-27632 (10 microM, Sigma Aldrich), rh-BMP4 (10 ng/ml, R&D) and protamine sulfate (10 μg/ml, Sigma). Concentrated lentiviral vectors individually coding for each forward programming factor were added to the well to MOI20 (multiplicity of infection). Subsequently, Aggrewell™ plates were centrifuged at 100 g for 3 minutes and put into the incubator (37 C/5% CO2) for 24 hours.

After 24 h (day 1), transduced EBs were collected and sowed in ultralow adherent cell culture plates (Corning) at a density of 600 EB per 10 cm2 dish in CDM supplemented with s rh-BMP4 (10 ng/ml, R&D) and rh-FGF2 (5 ng/ml, University of Cambridge).

EBs were collected 24 hours later (day 2) and further cultivated in ultralow adherent plates in Cellgro SCGM medium (Cellgenix, Germany) supplemented with rh-TPO (100 ng/ml, Cellgenix) and rh-SCF (25 ng/ml, Life Technologies).

At day 10, EBs were dissociated to single cells using CollagenaseIV and DispaseII (1 mg/ml, Gibco) followed by enzyme free cell dissociation buffer treatment (Gibco). Collected cells were cultivated on suspension culture plates (Grenier) for an additional 10 days in Cellgro SCGM supplemented with TPO (100 ng/ml) and IL1-beta (10 ng/ml, Miltenyi Biotec) for further MK maturation.

Culture medium is changed every three days by aspirating half of the volume and adding 2 times cytokine concentrated fresh medium on top. *Adherent cell protocol*: Small cell clumps were generated from sub-confluent hPSC cultures using a CollagenaseIV/DispaseII mix (1 mg/ml) and sowed on human fibronectin coated (50 ug/ml, Millipore) tissue culture plates in CDM with FGF (12 ng/ml) and Activin-A (15 ng/ml) at an approximated density of 2-5E+5 cells/10 cm2. Cells were transduced the day after with MOI20. The culture media used for the first two days were devised for pluripotency maintenance (as above) or mesoderm induction (FLyB; Bernardo et al. *Cell Stem Cell*. 2011 Aug. 5; 9(2): 144-55) depending on experiments. The following days, cells were maintained in Cellgro SCGM supplemented with TPO (100 ng/ml) and SCF (25 ng/ml) until analysis.

1.5 Cord Blood Derived Megakaryocytes

Cord blood was obtained after informed consent under a protocol approved by the National Research Ethics Service. CD34-positive cells (≥98%) isolated by magnetic cell sorting (Miltenyi Biotec) were seeded at 1E+5 cells/ml in Cellgro SCGM with TPO (100 ng/ml) and IL1-beta (10 ng/ml) and incubated for 10 days. We routinely obtained 70-90% CD41a+ and 20-60% CD42a+ cells by the end of the culture.

1.6 Flow Cytometry Analysis

Flow cytometry experiments were performed on a CyAn ADP (Beckman Coulter). Single cell suspensions were generated using CollagenaseIV/DispaseII and/or enzyme free dissociation buffer when needed. Cells were stained for 20-30' at room temperature in PBS 0.5% BSA 2 mM EDTA using combinations of FITC, PE and APC conjugated antibodies (all from BD Pharmingen except anti-GP6 antibody from NHSBT-Bristol). Background fluorescence was set against matched isotype control antibodies and compensation matrix defined using single-colour stained cells. Flow count beads (Flow count fluorospheres, Beckman Coulter) and DAPI were used to determine viable cell count in samples.

1.7 Immunofluorescence Analysis

MKs were cultivated on human fibrinogen coated (50 ug/ml, Millipore) tissue culture plates for 48 hours to monitor proplatelet formation. Cells were fixed with 2% PFA and permeabilised/blocked with 0.1% Saponin/0.2% Gelatin. Cells were incubated with primary antibodies (anti alpha-Tubulin, Sigma; anti vwf, Dako; anti P-selectin, NHSBT-Bristol) at room temperature for 2 hours and secondary antibodies conjugated with Cy3 or Alexa-488 fluorochromes (Invitrogen Molecular Probes) for 45 minutes. Cell nuclei were stained with DAPI before image acquisition on a confocal Zeiss Axiovert 200M microscope.

1.8 Cell Morphology Analysis

Cells were spun on a glass slide using cytofunnels at 400 g for 5', methanol fixed and Romanowsky stained (eosin and methylene blue). Cells were observed on a phase contrast Axiovert Zeiss microscope (630× magnification).

1.9 Transmission Electron Microscopy

MKs were fixed in 2% glutaraldehyde 0.1M phosphate buffer for 60' at room temperature. After washing with phosphate buffer, the samples were post-fixed with 1% osmium tetroxide in phosphate buffer for 60' on ice, ethanol dehydrated and infiltrated with and embedded in Epoxy resin. Ultrathin sections (50 nm) were cut and stained with 2% uranyl acetate in methanol and Reynolds' lead citrate. Samples were read using a FEI Tecnai 12 (Philips) transmission electron microscope.

1.10 Gene Expression Analysis by RT-QPCR

Total RNA was extracted with RNeasy kits according to the manufacturer's instructions (Qiagen) including DNase treatment. cDNA was prepared from 250-500 ng RNA using Maxima First Strand cDNA Synthesis Kit and random hexamers (Fermentas). QPCR reactions were performed in duplicates using recommended SYBR green based PCR mixes on ABI 7500HT or Mx3000P real time thermal cyclers using 2-step amplification protocols (Applied Biosystems, Agilent Technologies). Relative gene expression was calculated with the $2^{-deltaCt}$ method using HMBS for normalisation. Primer pairs were designed to amplify cDNA only, have no reported off targets after blasting against human Refseq and showed 80-120% PCR efficiencies. Endogene specific primers were designed to amplify UTR regions absent from transgene sequences while transgene specific primer pairs have 3' primers binding to viral sequences.

1.11 Whole Genome Expression Study

DNA free total RNA (RNeasy, Qiagen) was extracted from sorted CD42b+ cells (EasySEP, *Stem cell Technologies*; >95% purity) and 500 ng were hybridized to Illumina Human HT-12 v4 BeadArrays. Data import. Raw Illumina bead-level output was imported to the R statistical programming environment using functions of the beadarray package for the Bioconductor software suite. Data processing. Signal intensities were background corrected, summarized and converted to log 2 expression units using functionality of the beadarray package. Probe-sets without signal deemed significantly above background level in all profiles of at least one sample group (Illumina signal detection statistic p<0.01) were removed. Quantile normalization, implemented in the limma package for Bioconductor, was employed to equalize summarized expression intensity distributions across all sample profiles. Probe sets were annotated to gene targets using information available from the manufacturer. Data analysis. The statistical overrepresentation of gene categories among genes deemed differentially expressed between sample group profiles was assessed using the DAVID bioinformatics resource. Gene set enrichment analyses were performed using web tools from the Broad Institute using HaemAtlas data as input gene set. Differential gene expression between two sample groups was assessed through the output of a moderated t-test and significance P-values obtained converted to corrected q-values using the FDR method.

1.12 In Vitro Platelet Study.

Co-Culture on Feeder Cells. In order to promote platelet like particle (PLP) production, day 10 CB and day 20 hiPSC derived MKs were further cultivated for 48 h in Cellgro SCGM on gamma-irradiated stromal cells (OP9, ATCC CRL2749; C3H10T1/2, Riken Institute; HBMEC, courtesy of Dr. Weksler) sowed on gelatine coated tissue culture plates at 1E+4 cells/cm$^2$.

PLP Flow Analysis. Crude supernatant containing the PLPs were analysed by flow cytometry after addition of ⅕ volume of acid citrate dextrose (ACD, Sigma Aldrich) and cell removal by centrifugation at 150 g for 10'. Antibodies against human CD41a and CD42a were added directly to the medium (BD Pharmingen, APC/PE conjugated respectively, used at 1:50 dilution) and flow count fluorospheres used for quantification. Human platelets were analysed from fresh whole blood collected in citrate buffer.

Washed Platelet Preparation. Human platelet rich plasma (PRP) and hiPSC PLPs collected as above were washed twice in pH7.4 modified Tyrode-HEPES buffer (10 mM HEPES, 12 mM NaHCO3, 138 mM NaCl, 5.5 mM glucose, 2.9 mM KCl, and 1 mM MgCl2) using 800 g/10' centrifugation steps after an initial addition of prostaglandin E1 (1 M) and apyrase (1 U/ml) to prevent activation. Washed platelet counts were subsequently determined by flow cytometry.

Thrombus Formation in Laminar Flow. A defined amount of washed platelets or PLPs are mixed with 1 ml of mouse blood collected in ACD and the participation of human platelets to collagen induced mouse thrombi subsequently monitored by immunofluorescence. The procedure was modified from Auger J M, *ATVB*, 2008. Briefly, glass slides were locally coated with Horm collagen spots (100 ug/ml) and mounted into a flow chamber placed under a fluorescent microscope (EVOS system, *Advanced Microscopy Group*). The blood was then perfused through the chamber at 1600s-1 (7.2 ml/hr) for 3 minutes allowing thrombi formation on collagen spots. A perfusion of 1:100 diluted anti CD41a-FITC (BD Pharmingen) and anti P-selectin-PE (internal NHSBT-Bristol) was then run on the clots for 2 minutes and then washed before pictures were taken.

1.13 Gene Expression Analysis by Quantitative PCR

For gene expression analysis, cultivated cells are treated by TRIzol and RNA extracted from the aqueous phase following published protocol (Life Technologies). Alternatively, RNA is extracted and purified using Qiaprep RNeasy mini columns (Qiagen) including an on column DNA digestion step. Subsequently, cDNA is synthesized from 250-500 ng of purified RNA using the Maxima Reverse Transcriptase kit and random hexamers (Fermentas). The PCR reaction is performed using a SYBR green based PCR mix (Applied Biosystems, FastSYBR green) on a real time thermal cycler analyser (ABI 7500HT) following a fast 2-step amplification protocol. Relative gene expression quantification is calculated using the $2^{-ct}$ method using HMBS endogene expression as a reference. Primer pairs specific for any given gene has been carefully design using the NCBI primer design website in order to be separated by at least one intron on the corresponding gDNA and with no identified potential off target after a BLAST on the human RefSeq repository. Furthermore, all primer pairs have been tested for PCR efficiency between 80-120%. Primer pair specific for endogene expression has been designed in the 5' or 3' UTR of corresponding transcript. Primer pair specific for transgene expression are made of a reverse primer specific for the lentiviral backbone and a forward primer specific for a given transgene.

1.14 Cell Morphology Analysis

Cell morphology is observed after sedimentation on a glass slide by cytospin (400 g/5 min, 2,000-20,000 cells per slide) and Romanowsky staining (Eosin/Methylene blue) after Methanol fixation.

2. Results 2.1 A Combination of GATA1, FLI1 and TAL1 Induces Megakaryocyte Differentiation from Human Pluripotent Stem Cells We used a rational whole genome expression data driven process to select a list of candidate genes to test in the context of megakaryocyte forward programming (MK-FoP).

Figure 1:
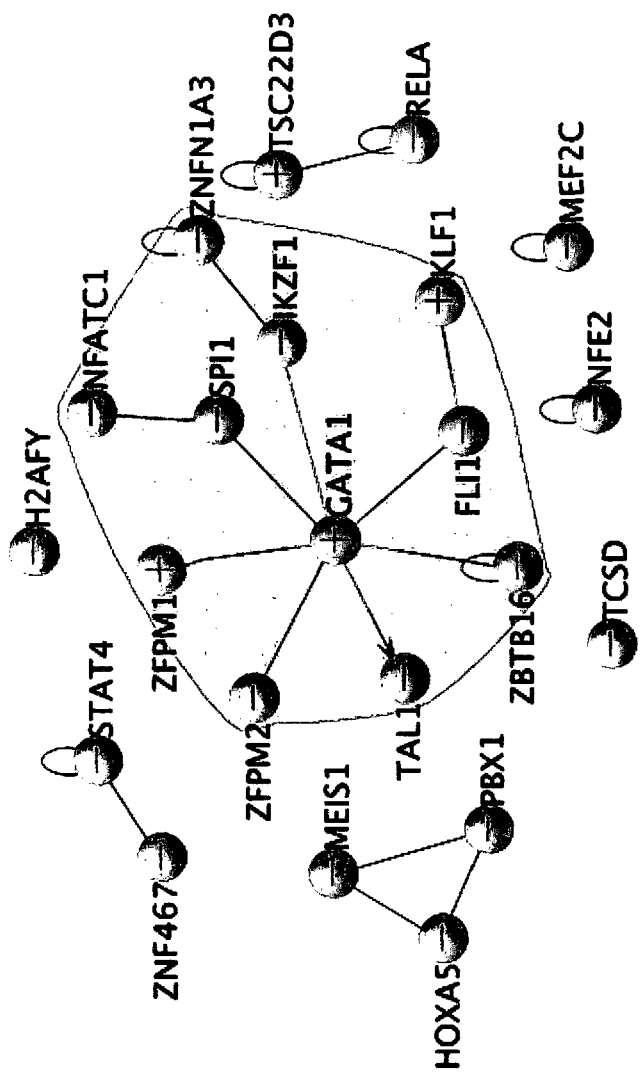
FIG. 1 shows the internal biological interactions of the top 20 TF candidates identified using VisANT, highlighting the 9 tested genes in this study (in dark) and the GATA1 centred network (grey shade). Tested combinations are indicated in the adjacent table.

Briefly, from the initial set of 116 genes coding for DNA binding proteins specifically expressed in cord-blood derived megakaryocytes (CB-MKs) compared to the H9 hESC line (hESC #1), 101 genes were retained after histone gene removal. 46 candidates were then selected upon analysis of protein-protein interaction network using VisANT software, integrating interactions with chromatin remodelling factors and level of gene expression. The visualization notably showed GATA1 as a core factor for 11 interacting partners (FIG. 1).

Figure 2:
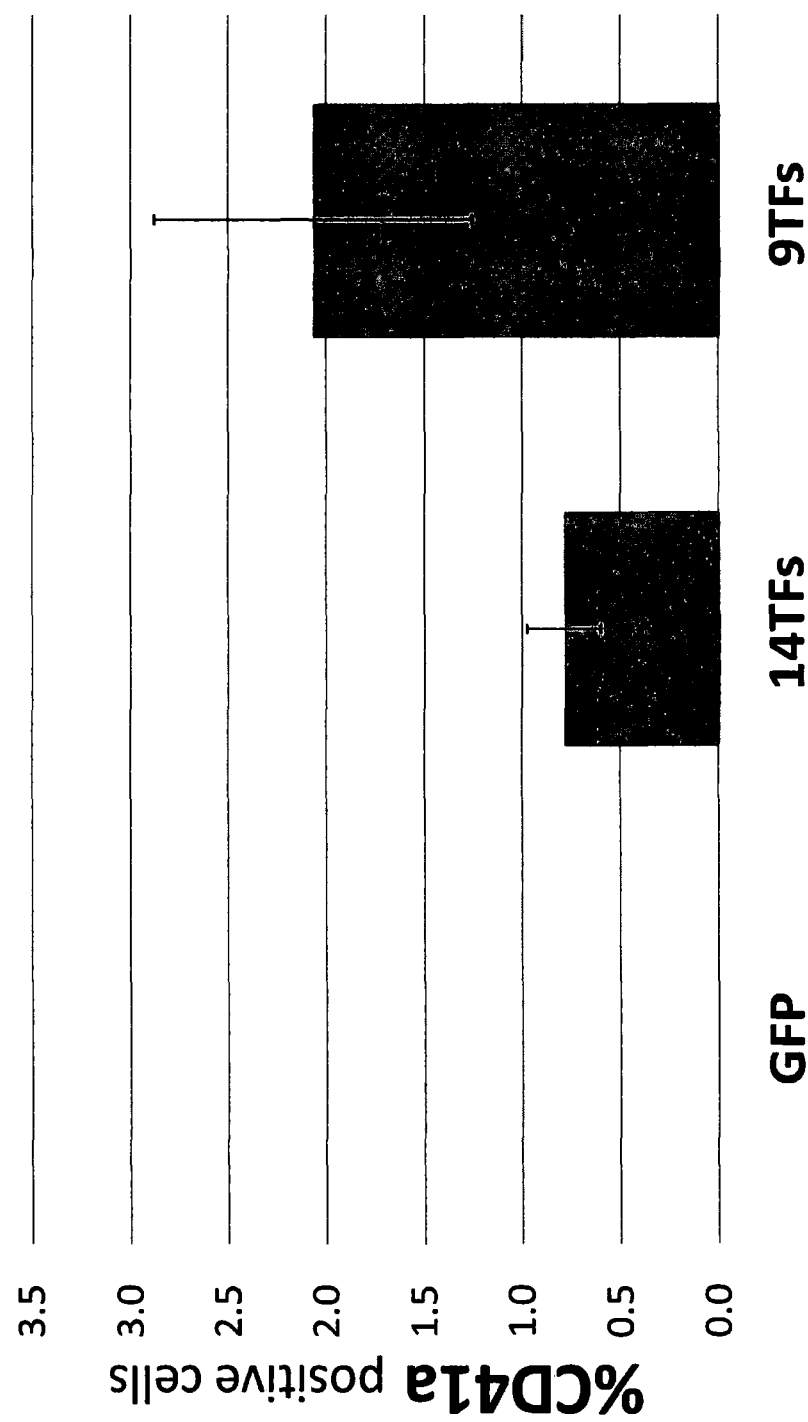
FIG. 2 shows a comparison between 14TF and 9TF combinations for MK-FoP of the H9 ES line (hESC#1).

14 transcription factor candidates were then cloned into lentiviral vectors for experimental assessment of their MK-FoP potential (Table 1 of FIG. 17). All 14 factors together were tested in parallel to a combination of 9 factors (higher rank factors) (FIG. 1). The 9TFs combination was found to be better than the 14TFs combination (FIG. 2).

The transduction of the hESC #1 line with the 9 TFs concurrently generated a well-defined population of CD41a positive cells (integrin alpha-IIb, megakaryocyte marker) identified by flow cytometry at day 7 (1.7±0.8%).

The CD41a+ population (9TFs forward-programmed cells) was then flow sorted at day 7 and individual transgene expression measured by RT-QPCR. Expression of all 9 TFs was detected in the CD41a negative cell population.

CD41a expressing cells showed a clear dominance in GATA1, FLI1 and TAL1 transgene expression providing indication that the combined expression of these 3 TFs was instrumental in the differentiation process (FIG. 3). Indeed, the 3-TFs combination showed a better CD41a+ cells outcome when compared with the 9-TFs or a reduced 5-TFs combination including GATA1 interactors (FIG. 4).

The potential of the GATA1+FLI1 combination was further explored by systematic addition of one of the remaining 7 factors (from 9TFs combination). The 14TFs, 9TFs and 5TFs (top ranked core network factors: GATA1+FLI1+TAL1+SPI1+ZBTB16 were tested in parallel in hESCs cells under pluripotent conditions without mesoderm induction (FIG. 5). The 3TFs combination was identified as the best one to drive forward programming. However, the GATA1+TAL1 combination was tested in a separate experiment and was not able to drive forward programming.

We validated further the requirement for a concurrent expression of the 3 TFs by testing all permutations of the latter (FIG. 6). Interestingly, the combination of GATA1 and FLI1 also generated a significant amount of CD41a+ cells under some conditions, although with a reduced efficiency providing indication that TAL1 might act more as a promoter than a primary inducer of forward programming.

In an initial MK-FoP protocol, hPSCs were dissociated with Collagenase IV in order to generate small cell clumps subsequently seeded on human fibronectin coated plates (around 5E+5 cells per 10 cm2). The day after (day 0), cell clumps were transduced by lentiviral vectors expressing t GATA1, TAL1 and FLI1, using MOI20 in presence of protamine sulfate. Cells were kept in pluripotency medium (chemically defined with Activin-A and FGF2) for two days, then in MK medium (chemically defined with TPO and SCF) for five days.

In a modified MK-FoP protocol, hPSCs were seeded as single cells after dissociation by TrypLE and allowed to attach on fibronectin coated plates in pluripotency medium supplemented with rock inhibitor Y-27632 (inhibition apoptosis) for 24 hours before transduction. In addition, cells were cultivated in mesoderm inducing conditions (FGF2, BMP4 and LY294002) for the first two days, then in MK medium (chemically defined with TPO and SCF) for five days.

Another modified MK-FoP protocol, which achieved the best cell yield, used an embryoid body culture approach in chemically defined conditions (FIG. 9). On transduction day (day 0), sub-confluent (50-80%) human pluripotent stem cells in pluripotency medium are dissociated to single cells using TrypLE (Life Technologies) for 5 min at 37° C. and viable cells counted on a haemocytometer. Desired amount of cells (e.g. 1E+6 cells) is added to Aggrewell™400 plates (Stemcell Technologies, France) in order to obtain embryoid bodies (EB) of 300 cells each following spin aggregation (detailed protocol in Aggrewell™ Technical manual). Importantly, lentiviral transduction is performed concomitantly to the aggregation phase. Briefly, cells are added to the well in CDM supplemented by Y-27632 (10 uM, Sigma Aldrich), rh-BMP4 (10 ng/ml, R&D) and protamine sulfate (8 ug/ml, Sigma). Concentrated lentiviral vectors individually coding for each forward programming factor are added to the well to MOI20 (multiplicity of infection) (2E+7 TU). Subsequently, Aggrewell™ plates are centrifuged at 100 g for 3 minutes and put into the incubator (37 C/5% CO2) for 24 hours. Transduced EB are collected the day after and rinse twice with PBS before being seeded in ultralow adherent cell culture plates (Corning) at a density of 600 EB per 10 cm2 dish in CDM plus rh-BMP4 (10 ng/ml, R&D) and rh-FGF2 (5 ng/ml, University of Cambridge) (i.e. mesoderm induction medium). Twenty four hours later, EB are collected, rinse with PBS and further cultivated in ultralow adherent plates in Cellgro SCGM medium (Cellgenix, Germany) supplemented with rh-TPO (100 ng/ml, Cellgenix) and rh-SCF (25 ng/ml, Life Technologies) (MK programming medium) until collection for analysis. Culture medium was changed every three days by aspirating half of the volume and adding 2 times cytokine concentrated fresh medium on top.

We performed additional analyses to confirm the megakaryocyte identity of the emerging CD41a+ population. The expression of key megakaryocyte genes was measured by QPCR at day 7. Forward programming of the hESC#2 line using the 3TF combination (FLI1, GATA1 and TAL1) was shown to induce expression of the megakaryocyte genes MPL (coding for the thrombopoietin (TPO) receptor), ZFPM1, RUNX1 and late differentiation markers like NFE2, MEIS1 and MEF2 C, as well as endogenous expression of GATA1, TAL1 and FLI1 (FIG. 7). Moreover, functional megakaryocyte progenitors were limited to the CD41a+ population at day 7 as demonstrated by clonogenic colony forming assays (FIG. 8). Indeed, these cells were found to be able to form mature MK colonies expressing CD41a and CD42b in semi-solid collagen cultures; interestingly, CD41a− cells did not show such potential. Importantly, key MK gene expression was shown to be restricted to the CD41+ cell population at day 7 (FIG. 9).

Altogether, we identified GATA1, FLI1 and TAL1 as a minimal combination of TFs inducing efficient megakaryocyte forward programming from hPSCs, TAL1 acting as an enhancer while GATA1 and FLI1 were instrumental to the programming process Time course analysis of surface marker expression by flow cytometry showed that human iPSC lines forward programmed using the 3TFs started to express CD41a from day 4 and CD42a from day 7 (FIG. 10). By day 14, cells kept in the MK culture medium TPO+SCF have reached near homogeneity for CD41a expression (91%) and a clear CD42a+ population has developed (22%), generating on average 13+/−7 millions mature MK per million iPSC input. The morphology of day 14 cells obtained by 3TF forward programming as observed by Romanowsky staining is very similar to in vitro cord blood derived MK regarding cell size, cytoplasm and nuclei content (FIG. 11). Mature MKs co-expressed CD41a, CD42b, GPVI, CD61 and CD42a.

To improve forward programming efficiency, we tested different chemically defined in vitro culture condition settings following 3-TF transduction of various hPSC lines. We measured the effect of commitment to mesoderm—the embryonic germ lineage from which the haematopoietic system originates—when induced simultaneously to 3-TF expression. We observed that mesoderm induction by exposition of hPSCs to BMP4, FGF2 and LY294002 for two days after viral transduction significantly increased the number of CD41a+ cells at day 7 in a variety of cell lines (FIG. 12). Importantly, the transduction efficiencies were similar for hPSCs maintained in pluripotent or mesoderm conditions indicating that mesoderm cells are indeed more responsive to the 3-TF driven forward programming. Additionally, we tested different hPSCs sowing techniques for their impact on forward programming at day 7. When comparing hPSCs sowed and transduced as clumps or single cells in tissue culture plates with those induced to form embryoid bodies (EB) by forced aggregation, we observed a significant improvement of the CD41a+ cell number with the latter (FIG. 13). Overall, we showed that the 3-TF driven MK-FoP efficiency was significantly improved by mesoderm commitment and cultivation as spin aggregated EB. The latter also offered the advantage of a standardised compact suspension culture and had been consequently used for the remaining experiments of this study.

2.2 A Chemically Defined Optimised Protocol Generates High Number of Mature Megakaryocytes Using the optimised chemically defined protocol comprising viral transduction of spin aggregated EBs at day 0, culture in mesoderm medium comprising FGF2 and BMP4 and LY294002 for two days after viral transduction; culture in MK medium comprising TPO and SCF until day 10 and dissociation of embryoid bodies showing cystic structures and actively growing cell aggregates to single cells at day 10 and further cultivated in MK maturation medium (TPO+ IL1b) for an additional 10 days, we analysed megakaryocyte maturation of 3-TF forward programmed hiPSCs compared to cord blood derived megakaryocytes. We observed a gradual increase of CD41a+ megakaryocyte progenitor cells followed by the progressive acquisition of the maturation marker CD42b (glycoprotein Ib, part of the MK specific GPIb/V/IX receptor complex) over cultivation time mimicking normal megakaryocyte differentiation.

Interestingly, the culture reached megakaryocyte purity (95±2% CD41a+, n=12) with more than half mature cells (56±4% CD42b+, n=12) by day 20 post-transduction without additional sorting procedure.

Further maturation could be obtained by maintaining cells in culture for longer periods (>80% CD42b+) but the cell yield is reduced by higher cell death as observed in prolonged cord blood cultures. In addition to CD41a and CD42b, we also observed expression of additional key surface proteins involved in megakaryocyte and platelet functions (itgb3 (CD61), gp6 and gp9 (CD42a)) by flow cytometry on hiPSC forward programmed day 20 cells and cord blood derived megakaryocytes. Similar expression profiles between cord blood and hiPSC derived megakaryocytes were observed.

Moreover, forward programmed cells showed typical size, morphological and ultrastructural features of megakaryocytes. We observed numerous polyploid cells with sizes ranging from 15 to 30 um and large cytoplasms (FIG. 14) and using transmission electron microscopy, cells displaying characteristic structures of maturing megakaryocytes as multi vesicular bodies—precursors of platelet granules—and developing demarcation membrane systems. Importantly, we showed that the 3-TF forward programming protocol efficiently generated mature megakaryocytes from different hiPSC lines with up to 33 fold increase in mature CD42b+ cell number compared to the hiPSCs input (FIG. 15).

We further characterised the megakaryocyte identity of the forward programmed cells by whole genome expression analysis. The tissue enrichment analysis between the parental hiPSCs and derived 3-TF forward programmed cells showed most significance for platelets (P=1.03E-62) while the top 5 enriched biological processes are related to haemostasis and platelet activity confirming on a genome wide level the megakaryocyte phenotype (Table 3). A gene set enrichment analysis ((GSEA web tools, Broad Institute) on the genes differentially expressed between hiPSC-MKs and the parental pluripotent stem cells showed a significant enrichment for megakaryocyte specific genes (dataset generated from HaemAtlas, MK compared to other blood lineages) and confirmed further the MK identity of forward programmed cells amongst other blood cell types (NES=1.47, data not shown). Intriguingly, we observed that MK-FoP applied to two different hiPSC lines, although showing variability in cell number outcome (FIG. 15), generated highly similar expression profiles in the differentiated mature MKs (R2=0.99).

We identified 13 TFs whose expression is missing in hiPSC-MKs compared to CB or peripheral blood differentiated MKs (Table 2).

These genes may be determinants for post-natal phenotype acquisition and may further improve the maturation of hiPSC derived MKs.

In summary, we demonstrated that the 3-TF forward programming approach was able to efficiently generate genuine megakaryocytes sharing key features with their cord blood derived counterpart.

2.3 Forward Programmed Megakaryocytes Produce Functional Platelet-like Particles In Vitro We tested the ability of forward programmed megakaryocytes to generate functional platelet like particles (PLPs) in vitro. Platelet production happens by a process of proplatelet formation by mature MKs. Immunofluorescence analysis of hiPSC forward programmed day 20 megakaryocytes cultivated for an additional 48 hours on fibrinogen coated plates showed pro-platelet like cytoplasmic protrusions in vitro showing bulbous structures expressing von Willebrand factor (vwf) and P-selectin along alpha-tubulin positive cytoplasmic filaments. von Willebrand factor (vwf) and P-selectin which are key proteins embedded in platelet granules.

The release of platelet-like particles (PLPs) in the culture supernatant was highly improved by co-culture of hiPSC derived MKs on the OP9 stromal cell line for 48 hours. In such conditions, we detected significant amount of PLPs by flow cytometry identified as human platelet size particles co-expressing CD41a and CD42a. They were produced at an average of 1±0.3 million per million hiPSC-MK input after 48 hours of co-culture on various feeder cells (FIG. 16).

We explored further the functionality of the generated PLPs by monitoring their contribution to in vitro collagen induced mouse thrombi under flow. Human particles were detected by immunostaining after clot formation on collagen fibres following mixing of PLPs or human platelets with mouse blood (3E+6 and 5E+6 per ml respectively). Activated platelets co-expressing CD41a and P-selectin on their surface were also identified. This shows that the hiPSC derived PLPs in formed mouse platelet clots displayed granule content on their surface, demonstrating functional activation.

We describe above a method for generating megakaryocytes from hPSCs using a forward programming strategy based on combined forced expression of the three transcription factors GATA1, FLI1 and TAL1. The generated cells were genuine megakaryocytes able to release functional platelet like particles in vitro.

Indeed, this method offers several advantages compared to previously described methods. First, the differentiation and maturation of megakaryocytes is achieved in chemically defined conditions without supporting stromal cells. This improves reproducibility and will greatly help the transition to clinically compatible procedures. By acting directly at the level of the gene regulatory network, the forward programming strategy allows an efficient megakaryocyte differentiation using a reduced cytokine combination and minimal cell handling. The cell yield of forward programming matches the best described approaches so far; leading in 20 days to up to 50 megakaryocytes per hiPSC input and provides a pure megakaryocyte population without the need for sorting (>95% CD41a+ and >50% CD42a+). An additional benefit of the protocol described above is the use of suspension culture only (embryoid bodies followed by single cells) which greatly reduces the footprint of the experiment and should facilitate its transfer to large scale production systems.

A mesoderm inducing treatment concomitant to transgene expression was found to be beneficial to forward programming, providing indication that the epigenome and/or transcriptional profile of mesoderm cells were more amenable to respond to the programming factors. The forward programming happens very rapidly since markers of MK commitment are detected as early as four days after 3 TFs transduction, the MK potential is restricted from day 7 to the CD41a+ population and cells show an early dependency to haematopoietic cytokines.

In conclusion, our study demonstrates forward programming to generate MKs from hiPSCs. The generated hiPSC-megakaryocytes shared key features with their cord blood derived counterpart at the genetic and ultrastructural levels, and are able to release functional platelet like particles in vitro. This novel differentiation approach will have broad applications in both basic research and clinical development of hiPSC derived transfusion products.

TABLE 2

| | Factor | Name | Gene ID | Reference Sequence |
|---|---|---|---|---|
| 1 | ABLIM1 | Actin binding LIM protein 1 | 3983 | NP_001003407.1 GI:51173713 (SEQ ID NO: 4) |
| 2 | FHL1 | Four and a half LIM domains 1 | 2272 | NP_001153174.1 GI:228480211 (SEQ ID NO: 5) |
| 3 | RUNX3 | Runt-related transcription factor 3 | 864 | NP_001026850.1 GI:72534652 (SEQ ID NO: 6) |
| 4 | NFIC | Nuclear factor I/C (CCAAT-binding transcription factor) | 4782 | NP_001231931.1 GI:350529396 (SEQ ID NO: 7) |
| 5 | NFIL3 | Nuclear factor, interleukin 3 regulated | 4783 | NP_005375.2 GI:52630429 (SEQ ID NO: 8) |
| 6 | VDR | Vitamin D (1, 25-dihydroxyvitamin D3) receptor | 7421 | NP_000367.1 GI:4507883 (SEQ ID NO: 9) |
| 7 | MESP1 | Mesoderm posterior 1 | 55897 | NP_061140.1 GI:14149724 (SEQ ID NO: 10) |
| 8 | BTBD11 | TB (POZ) domain containing 11 | 121551 | NP_001018082.1 GI:65786661 (SEQ ID NO: 11) |
| 9 | APPL2 | Adaptor protein, phosphotyrosine interaction, PH domain and leucine zipper containing 2 | 55198 | NP_060641.2 GI:24586663 (SEQ ID NO: 12) |
| 10 | MICAL1 | Microtubule associated monooxygenase, calponin and LIM domain containing 1 | 64780 | NP_073602.3 GI:205360947 (SEQ ID NO: 13) |
| 11 | BATF | Basic leucine zipper transcription factor, ATF-like | 10538 | NP_006390.1 GI:5453563 (SEQ ID NO: 14) |
| 12 | SCMH1 | Sex comb on midleg homolog 1 | 22955 | NP_001026864.1 GI:72534680 (SEQ ID NO: 15) |
| 13 | MBP | Myelin basic protein | 4155 | NP_001020252.1 GI:68509930 (SEQ ID NO: 16) |

TABLE 3

Top 5 enriched Biological Processes (hiPSC-MK vs. hiPSC)

| Term | p-value | Significant Genes No. | Total Genes No. |
|---|---|---|---|
| hemostasis | 1.48E−25 | 191 | 501 |
| coagulation | 3.15E−25 | 190 | 500 |
| platelet activation | 3.33E−25 | 107 | 216 |
| blood coagulation | 1.08E−24 | 188 | 497 |
| vesicle-medicated transport | 5.19E−22 | 284 | 903 |

The invention claimed is:
1. A method of producing megakaryocyte progenitor cells comprising;
  (i) transducing isolated human pluripotent stem cells (hPSCs) concurrently with a nucleic acid encoding GATA binding protein 1 (GATA1), Friend leukemia virus integration 1 (FLI1) and T cell acute lymphocytic leukemia protein 1 (TAL1) transcription factors into a population of isolated human pluripotent stem cells (hPSCs);
  (ii) culturing the transduced hPSCs of step (i) without feeder cells in a mesoderm chemically defined medium (CDM) comprising one or more of Activin-A, FGF2 of BMP4 for 1 or more days, thereby inducing mesoderm progenitor cells; and
  (iii) culturing the mesoderm progenitor cells of step (ii) in megakaryocyte (MK) programing culture medium without feeder cells and comprising one or more of recombinant proteins (Thrombopoietin) TPO, Stem Cell Factor (SCF) or IL-beta (ILB), wherein the combination of GATA1, FLI1 and TAL1 transcription factors is expressed, such that one or more cells in the population are programmed into megakaryocyte progenitor cells that express at least CD41a.

2. The method according to claim 1 wherein the transcription factors are human transcription factors.

3. The method according to claim 1, wherein the megakaryocyte progenitor cells express CD34 and CD41a.

4. The method according to claim 1 wherein the nucleic acid further encodes two, three or more of IKZF1, HOXA5, RUNX1, ZFPM2, ZFPM1 and GATA2 transcription factors; or two, three or more of ABLIM1, FHL1, RUNX3, NFIC, NFIL3, VDR, MESP1, BTBD11, APPL2, MICAL1, BATF, SCMH1 and MBP transcription factors.

5. The method according to claim 1 wherein the nucleic acid encodes a combination of transcription factors, wherein the combination of transcription factors consists of GATA 1, FLI1 and TAL1.

6. The method according to claim 1 comprising isolating and/or purifying said megakaryocyte progenitor cells.

7. The method according to claim 6 comprising expanding the population of megakaryocyte progenitor cells.

8. The method according to claim 6 comprising storing the population of megakaryocyte progenitor cells.

9. The method according to claim 1, further comprising culturing the megakaryocyte progenitor cells in a megakaryocyte maturation medium comprising TPO and/or SCF and/or IL1-beta (ILB) to produce mature megakaryocyte cells.

10. The method according to claim 9 wherein the megakaryocyte progenitor cells are cultured in MK maturation medium comprising TPO and/or SCF and/or IL1-beta to produce said mature megakaryocyte cells.

11. The method according to claim 9 wherein the mature megakaryocyte cells are CD61+, CD34+ or CD34−, CD41a+, CD42a+, CD42b+.

12. The method according to claim 9 comprising isolating and/or purifying said mature megakaryocyte cells.

13. The method according to claim 9 further comprising causing or allowing one or more of said mature megakaryocyte cells to produce platelets and/or platelet size particles co-expressing CD41a and CD42a.

14. The method according to claim 1 wherein the human pluripotent stem cells are ES cells, iPS cells, fetal or adult somatic stem cells, or haematopoietic stem cells and progenitors.

15. The method according to claim 1 wherein the pluripotent stem cells are hiPS cells derived from a sample of normal cells obtained from an individual or a sample of cells having a disease associated phenotype or genotype obtained from an individual.

* * * * *

UNITED STATES PATENT AND TRADEMARK OFFICE
CERTIFICATE OF CORRECTION

PATENT NO. : 10,604,738 B2
APPLICATION NO. : 14/407044
DATED : March 31, 2020
INVENTOR(S) : Pedersen et al.

Page 1 of 1

It is certified that error appears in the above-identified patent and that said Letters Patent is hereby corrected as shown below:

On the Title Page

Below the abstract, delete "15 Claims, 17 Drawing Sheets" and insert -- 13 Claims, 17 Drawing Sheets --

In the Claims

Claim 1, Column 69, Line 3, after the word "comprising", the ";" should be a -- : --
Claim 1, Column 69, Line 13, the text "FGF2 of BMP4" should read -- FGF2, or BMP4 --
Claim 1, Column 69, Line 18, the text "(Thrombopoietin) TPO" should read -- Thrombopoietin (TPO) --

Claim 5 and Claim 10 are deleted

Signed and Sealed this
Eighteenth Day of August, 2020

Andrei Iancu
*Director of the United States Patent and Trademark Office*